US011339376B2

(12) United States Patent
Koike et al.

(10) Patent No.: US 11,339,376 B2
(45) Date of Patent: May 24, 2022

(54) STABLE PRODUCTION OF VIRULENT ENTEROVIRUS 71 AND USE THEREOF

(71) Applicant: TOKYO METROPOLITAN INSTITUTE OF MEDICAL SCIENCE, Tokyo (JP)

(72) Inventors: Satoshi Koike, Tokyo (JP); Kyousuke Kobayashi, Tokyo (JP); Yui Sudaka, Tokyo (JP); Ayumi Imura, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 167 days.

(21) Appl. No.: 16/496,326

(22) PCT Filed: Mar. 27, 2018

(86) PCT No.: PCT/JP2018/012410
§ 371 (c)(1),
(2) Date: Sep. 20, 2019

(87) PCT Pub. No.: WO2018/181298
PCT Pub. Date: Oct. 4, 2018

(65) Prior Publication Data
US 2020/0032222 A1 Jan. 30, 2020

(30) Foreign Application Priority Data
Mar. 31, 2017 (JP) ............................ JP2017-072562

(51) Int. Cl.
*C12N 7/00* (2006.01)
*C12N 5/071* (2010.01)
*C12Q 1/70* (2006.01)
*G01N 33/15* (2006.01)

(52) U.S. Cl.
CPC ............ *C12N 7/00* (2013.01); *C12N 5/0602* (2013.01); *C12Q 1/70* (2013.01); *G01N 33/15* (2013.01); *C12N 2511/00* (2013.01); *C12N 2770/32021* (2013.01); *C12N 2770/32321* (2013.01)

(58) Field of Classification Search
None
See application file for complete search history.

(56) References Cited

FOREIGN PATENT DOCUMENTS

| | | |
|---|---|---|
| CN | 103081868 | 5/2013 |
| JP | 2010268688 | 12/2010 |

OTHER PUBLICATIONS

Yamayoshi et al. (Emerging Microbes and Infections, 3:e53 (Year: 2014).*
Lim et al. (Therapeutic Advances in Vaccines and Immunotherapy 2019, vol. 7: 1-10) (Year: 2019).*
"Extended European Search Report corresponding to European Application No. 18777990.5 dated Dec. 8, 2020".
Imura, Ayumi , et al., "Development of an Enterovirus 71 Vaccine Efficacy Test Using Human Scavenger Receptor B2 Transgenic Mice", Journal of Virology 94(6):e01921-19 (Mar. 2020) (14 pages).
Kobayashi, Kyousuke , et al., "Heparan sulfate attachment receptor is a major selection factor for attenuated enterovirus 71 mutants during cell culture adaptation", PLOS Pathogens 16(3) published Mar. 18, 2020 (25 pages).
Caggana et al. "Identification of a Single Amino Acid Residue in the Capsid Protein VP1 of Coxsackievirus B4 That Determines the Virulent Phenotype", Journal of Virology 67(8):4797-4803 (1993).
Chee et al. "Enterovirus 71 Uses Cell Surface Heparan Sulfate Glycosaminoglycan as an Attachment Receptor", Journal of Virology 87(1):611-620 (2013).
Chee et al. "VP1 residues around the five-fold axis of enterovirus A71 mediate heparan sulfate interaction", Virology 501:79-87 (2016).
Fujii et al. "Transgenic mouse model for the study of enterovirus 71 neuropathogenesis", PNAS 110(36):14753-14758 (2013).
International Search Report corresponding to International Application No. PCT/JP2018/012410 dated Jun. 19, 2018.
Li et al. "Establishment of cell lines with increased susceptibility of EV71/CA16 by stable overexpression of SCARB2", Virology Journal 10:250 11 pages (2013).
Liou et al. "A new animal model containing human SCARB2 and lacking stat-1 is highly susceptible to EV71", Scientific Reports 6:31151 10 pages (2016).
Nishimura et al. "The Suramin Derivative NF449 Interacts with the 5-fold Vertex of the Enterovirus A71 Capsid to Prevent Virus Attachment to PSGL-1 and Heparan Sulfate", PLOS Pathogens 11:e1005184 19 pages (2015).
Sudaka et al. "Change in EV71 virulence by substitution of amino acid 145 of capsid protein VP1", Abstracts of the Annual Meeting of the Japanese Society for Virology (non-official translation) p. 323, p. 2-045 (2016).
Yamayoshi et al. "Receptors for enterovirus 71", Emerging Microbes and Infections 3:e53 7 pages (2014).
Zhou et al. "A safe and sensitive enterovirus A71 infection model based on human SCARB2 knock-in mice", Vaccine 34:2729-2736 (2016).
Chen, Yen-Hsi , et al., "The GAGOme: a cell-based library of displayed glycosaminoglycans", Nature Methods 15:881-888 (Nov. 2018).

(Continued)

*Primary Examiner* — Shanon A. Foley
*Assistant Examiner* — Myron G Hill
(74) *Attorney, Agent, or Firm* — Myers Bigel, P.A.

(57) ABSTRACT

Provided is a host cell for stably propagating a virulent hand, foot and mouth disease virus, the host cell expressing no heparan sulfate and overexpressing primate scavenger receptor class B member 2 (SCARB2). Also provided is a method for screening for an anti-hand, foot and mouth disease virus vaccine or an anti-hand, foot and mouth disease virus drug using a stably cultured virulent hand, foot and mouth disease virus.

8 Claims, 4 Drawing Sheets

Specification includes a Sequence Listing.

(56) References Cited

OTHER PUBLICATIONS

Lin, Yi-Wen , et al., "Human SCARB2-Mediated Entry and Endocytosis of EV71", PLOS ONE 7(1): e30507 (13 pages) (Jan. 17, 2012).

Thamamongood, Thiprampai , et al., "A Genome-Wide CRISPR-Cas9 Screen Reveals the Requirement of Host Cell Sulfation for Schmallenberg Virus Infection", Journal of Virology 94(17):e00752-20 (10 pages) (Sep. 2020).

Yamayoshi, Seiya , et al., "Scavenger receptor B2 is a cellular receptor for enterovirus 71", Nature Medicine 15(7):798-802 (Jul. 2009).

"Abstracts of The 64th Annual Meeting of the Japanese Society for Virology, Sep. 30, 2016, P2-045, P2-046".

"Office Action corresponding to Japanese Application No. 2019-509880 dated Mar. 7, 2022".

* cited by examiner

SEQUENCE LISTING

```
<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: EXT1-sgRNA sense

<400> SEQUENCE: 1

caccacccac aacacatc                                                    18


<210> SEQ ID NO 2
<211> LENGTH: 17
<212> TYPE: DNA
<213> ORGANISM: Artificial Sequence
<220> FEATURE:
<223> OTHER INFORMATION: EXT1-sgRNA antisense

<400> SEQUENCE: 2

aaaccatttc ctccttc                                                     17


<210> SEQ ID NO 3
<211> LENGTH: 22
<212> TYPE: DNA
<213> ORGANISM: Artificial Sequence
<220> FEATURE:
<223> OTHER INFORMATION: EXT2-sgRNA sense

<400> SEQUENCE: 3

cacccttcaa ttcaccaatc ca                                               22


<210> SEQ ID NO 4
<211> LENGTH: 18
<212> TYPE: DNA
<213> ORGANISM: Artificial Sequence
<220> FEATURE:
<223> OTHER INFORMATION: EXT2-sgRNA antisense

<400> SEQUENCE: 4

aaacctattt acattaac                                                    18


<210> SEQ ID NO 5
<211> LENGTH: 48
<212> TYPE: DNA
<213> ORGANISM: Artificial Sequence
<220> FEATURE:
<223> OTHER INFORMATION: EV71 Isehara 5'-primer

<400> SEQUENCE: 5

cggcggccgc gtaatacgac tcactatagg ttaaaacagc ctgggttg                   48


<210> SEQ ID NO 6
<211> LENGTH: 39
<212> TYPE: DNA
<213> ORGANISM: Artificial Sequence
<220> FEATURE:
```

-continued

<223> OTHER INFORMATION: EV71 Isehara 3'-primer

<400> SEQUENCE: 6
tactcacttt ttttttttt ttttttttt ttctattct 39

<210> SEQ ID NO 7
<211> LENGTH: 7434
<212> TYPE: DNA
<213> ORGANISM: Enterovirus 71 Isehara strain

<400> SEQUENCE: 7

```
ttaaaacagc ctgtgggttg cacccaccca cagggcccac tgggcgccag cactctggta     60
ctgaggtacc tttgtgcgcc tgtttttact tcccctcccc gaagtaactt agaagctgta    120
aatcaacgat caatagtagg tgtgacacac cagtcacact tggtcaagc acttctgttt    180
ccccggactg agtatcaata ggctgctcgc gcggctgaag gagaaaacgt tcgttacccg    240
accaactact tcgagaagct tagtaccacc atgaacgagg cagagtgttt cgttcagcac    300
aaccccagtg tagatcaggc tgatgagtca ctgcaacccc catgggcgac catggcagtg    360
gctgcgttgg cggcctgccc atggagaaat ccatgggacg ctctaattct gacatggtgc    420
gaagagccta ttgagctagt tggtagtcct ccggcccctg aatgcggcta atcctaactg    480
cggagcacat gctcacaaac cagtgggtgg tgtgtcgtaa cgggcaactc tgcagcggaa    540
ccgactactt tgggtgtccg tgtttccttt tattcttata ttggctgctt atggtgacaa    600
tcaaagaatt gttaccatat agctattgga ttggccatcc agtgtgcaac agagcaattg    660
tttatctatt cattggtttc gtacctttat cactgaagtc tgtgatcact cttaaattca    720
ttttgaccct caatacaatt aaacatgggc tcacaggtgt ccacacagcg ctccggttcg    780
catgaaaatt ctaactcagc caccgagggt tccaccataa attatactac cattaattac    840
tataaagact cctatgccgc cacagcaggt aaacagagcc ttaagcagga cccagacaag    900
tttgcaaatc ctgtcaaaga catcttcact gaaatggcag cgccattaaa atctccatct    960
gctgaggcat gtggttacag cgatcgggta gcacagttaa ctattggcaa ctctaccatc   1020
actacgcaag aagcagcaaa catgatagtt ggctatggtg agtggccatc ctactgctcg   1080
gattctgacg ccacagcagt ggacaaacca acgcgcccag atgtttcagt gaataggttt   1140
tatacattgg acactaaatt gtgggagaaa tcatccaagg ggtggtactg gaaattcccg   1200
gatgtgttga ctgaaaccgg ggtcttcggt caaaatgcac aattccacta cctctatcgg   1260
tcgggattct gcattcacgt gcagtgcaat gctagtaagt tccaccaagg agcactccta   1320
gtcgctgtcc tcccagaata tgtcattggg acagtagcag gtggcacagg gacggaggat   1380
agtcaccccc cttacaagca gactcaaccc ggtgctgatg gctttgaatt gcaacacccg   1440
tacgtgcttg atgctggcat tccaatatca caattaacag tgtgcccaca ccagtggatt   1500
aatttgagga ctaacaattg tgccacaata atagtaccgt acataaacgc actacccttt   1560
gattctgcct tgaaccattg caactttggt ctgctggttg tgcctattag cccgttagat   1620
tatgaccaag gtgcgacgcc agtgatcccc attactatca cattggcccc aatgtgctct   1680
gaatttgcag gccttaggca agcagttacg caagggtttc ctactgagct gaaacccggc   1740
acaaaccaat ttttaaccac tgacgatggc gtctcagcac ccattctgcc aaactttcac   1800
cccaccccgt gtatccatat acccggtgaa gttagaaact tgctagagct atgccaggtg   1860
gagaccatct tagaggttaa caatgtaccc acgaatgcca ctagcttaat ggagaggctg   1920
cgcttcccgg tctcagccca agccgggaaa ggtgaactat gtgcagtgtt cagagctgac   1980
```

cctgggcgaa atggaccatg gcagtccacc ctgttgggtc agttgtgtgg gtattacacc 2040
caatggtcag gatcactgga agtcaccttc atgtttactg ggtcctttat ggctactggc 2100
aagatgctca tagcatacac accaccagga ggccccttac ccaaggaccg ggcgaccgcc 2160
atgttgggta cacacgtcat ctgggacttt gggttgcaat cgtctgtcac ccttgtaata 2220
ccatggatca gcaacactca ctacagagcg cacgctcgag atggtgtgtt cgattactac 2280
actacaggtt tggttagcat atggtaccag acgaattacg tggttccaat tggggcacct 2340
aatacagcct acataatagc attggcggca gcccagaaga atttcaccat gaagttgtgt 2400
aaggatgcta gtgatatcct acagacaggc actatccagg gagacagggt ggcagatgtg 2460
attgagagtt ctatagggga tagtgtgagc agagccctca cccaagcttt accggcacct 2520
acaggccaaa acacgcaggt aagcagccac cgattagaca ctggtaaagt tccagcactc 2580
caagccgctg aaattggagc atcatcaaat gccagcgatg agagtatgat tgagacacga 2640
tgtgttctta attcacacag cacagctgag accactcttg atagcttctt cagtagagcg 2700
ggattagttg gagagataga cctccctctt gaaggcacaa ccaacccgaa tgggtatgca 2760
aattgggaca tagacataac aggttacgcg caaatgcgta gaaaggtgga gctgtttacc 2820
tacatgcgtt ttgacgcaga gttcaccttc gtagcgtgca cgcctaccgg ggaagttgtc 2880
ccgcaattgc tccaatatat gtttgtacca cctggagccc ccaagccaga ctctagagaa 2940
tctcttgcat ggcaaactgc cactaatccc tcagtctttg tgaagctgtc agacccccca 3000
gcacaggttt cagttccatt catgtcacct gcaagcgcct accaatggtt ttatgacggg 3060
tatcccacat tcggtgaaca caagcaggaa aaagaccttg aatatggggc atgcccaaac 3120
aacatgatgg gtacgttctc ggtgcggact gtaggaacct cgaagtccaa gtacccattg 3180
gtgatcagga tttacatgag gatgaagcac gtcagggcgt ggatacctcg cccaatgcgt 3240
aaccaaaact acttatttaa agccaaccca aattatgctg gtaactccat taaaccaact 3300
ggtaccagtc gcacagcgat caccactctc gggaaatttg gacagcaatc cggggctatc 3360
tacgtgggca actttagagt ggttaaccgc caccttgcta ctcataatga ctgggcaaac 3420
cttgtttggg aagacagctc ccgcgacttg ctcgtatcat ctacctctgc ccaaggttgt 3480
gacacgattg ctcgttgcaa ctgtcagaca ggagtgtatt actgtaactc aatgagaaaa 3540
cactatccgg tcagtttctc gaagcccagt ttgatcttcg tagaggccag cgagtattac 3600
cctgctagat accagtcaca ccttatgctt gcagtgggtc actcggagcc aggggattgc 3660
ggtggcattc ttagatgcca acacggtgtc gtagggatag tttccaccgg gggaaacggc 3720
ctagtggggt tcgccgatgt gagggatctt ctgtggttgg atgatgaggc catggagcag 3780
ggcgtgactg attacattaa agggcttgga gatgcttttg gcatggggtt tacagacgca 3840
gtgtcaagag aagttgaagc attgaaaaat cacttgatcg gctcagaggg tgccgtggag 3900
aggatcctta agaacttagt taaactcatc tctgcgctcg tcattgtcat caggagtgat 3960
tatgacatgg tcacattgac ggcaacactt gccctgatcg ggtgtcacgg cagcccttgg 4020
gcctggatta agtcgaaaac agcgtcgatt ttgggcatac cgatggctca aaagcagagt 4080
gcctcttggt taaagaagtt caacgatgcg gcgagtgccg ccaaggggct tgagtggatc 4140
tccaacaaaa tcagcaaatt tatcgattgg ctcaaggaga aaattatccc ggctgctaaa 4200
gagaaagtcg agtttctaaa caatctaaag caactcccct tattggagaa ccaaatttct 4260
aatctcgaac agtcagcagc ttcccaggag gacctcgaag cgatgtttgg caacgtgtct 4320

-continued

```
tatctggccc acttctgccg caaattccaa cccctctatg ccacggaagc aaagagggtg   4380
tatgccctag aaaagagaat gaataattac atgcagttca agagcaaaca ccgtattgaa   4440
cctgtatgcc tgattatcag aggctcgcct ggcactggga agtccttggc aacagggatt   4500
attgctagag ctatagctga caagtaccac tccagtgtgt attccttacc tccggaccca   4560
gatcactttg atggatacaa gcaacagatc gttactgtta tggatgatct atgccaaaac   4620
ccggacggga aagacatgtc actattttgt cagatggtct ccacagtgga ttttataccg   4680
cctatggcat ctctggagga gaagggagtc tcattcacct ccaagtttgt gattgcctcc   4740
actaacgcca gtaacatcat agtgccaaca gtctcggatt cagatgccat ccgtcgtcgg   4800
ttcttcatgg actgcgatat tgaggtgacc gattcctata agacagagct gggtaggctt   4860
gatgcaggga gagcagctag gctgtgctct gagaacaaca ctgcaaactt taaacggtgc   4920
agcccattag tctgtgggaa agcaatccag cttagggata ggaagtctaa ggtgagatac   4980
agtgtggaca cggtggtgag tgagcttatc agggagtata acaacagatc agctattggg   5040
aataccatcg aagctctttt ccaaggaccc cctaaattta gaccgataag gattagccta   5100
gaggagaagc ccgcacctga tgctattagt gacctattag ctagtgtcga tagtgaagag   5160
gttcgccaat actgtagaga tcagggatgg attgtacctg attctcccac caacgttgag   5220
cgccacttga atagagctgt cttgatcatg caatctatag ccaccgtggt agcggttgtg   5280
tcccttgttt atgtcatcta caagttgttc gccggttttc aaggagcata ttccggcgcc   5340
cctaagcaag cactcaagaa accagtgttg cgtacggcaa ctgtgcaggg gccaagcttg   5400
gacttcgccc tatctctact taggaggaac atcaggcagg tccaaaccga ccagggccac   5460
tttacaatgt taggagtgcg agaccacttg gctgtgctcc ccagacactc ccaaccagga   5520
aagaccatct gggttgaaca caaattagtg aagatcgtgg atgctgtgga gctagtagat   5580
gagcaaggag ttaacctaga gctcacactg gtgacgcttg acaccaacga aaaatttaga   5640
gacatcacaa gattcatacc agaaacaatt agtcctgcta gtgatgccac tttagttata   5700
aatactgaac atatgcccaa tatgtttgtg ccagttggag atgtagtcca gtatggattt   5760
ttgaacctta gtggtaagcc cactcacagg actatgatgt acaatttccc aacaaaagca   5820
ggacagtgtg gtggtgtcgt gactgctgtg ggtaaagtga ttgggatcca cattggtggc   5880
aacggtaggc agggtttctg cgctgccctg aagagaggat acttttgcag cgaacaaggt   5940
gagatccaat ggatgaagcc caacaaagaa actggcaggt taaacatcaa cggacctact   6000
cgcactaaac ttgaaccaag tgtctttcat gatgtgttcg agggcactaa agagccagca   6060
gtgctgacta gtaaagaccc aaggctggag gttgactttg aacaggctct tttttcaaaa   6120
tacgtgggaa acacgcttca tgaacctgac gagtttgtca aggaggcggc cttacattat   6180
gccaaccaac tcaagcagtt agatattaag accaccaaga tgagcatgga ggatgcttgt   6240
tacggtacag agaacctgga agctatagac cttcacacaa gtgcaggata tccatacagt   6300
gcactgggca tcaagaaaag ggatattttg gacccaacaa ctcgcgatgt cagcaagatg   6360
aaattttaca tggacaagta tgggttagat ctaccgtact ccacttatgt taaagatgaa   6420
ctcagggcca tcgacaaggt caagaaaggg aagtctcgtc tcatagaagc gagcagtcta   6480
aatgactcag tgtacttgag aatgacattt gggcaccttt atgaaacttt tcatgccaat   6540
ccaggtacag tcactggttc agctgttgga tgcaatccag atgtgttctg gagtaagttg   6600
ccaattctac ttccaggatc gctttttgca tttgactact cggggtatga cgctagtctc   6660
agcccagtgt ggttcagggc gctggagata gtcctacggg aaattgggta ctccgaggac   6720
```

```
gcagtgtctc tcatagaagg gatcaatcac actcaccatg tgtaccgcaa taaaacttat   6780

tgtgttcttg ggggaatgcc ctcaggttgc tcaggcacct ccattttcaa ctcgatgatc   6840

aataacatca ttattaggac actcctgatt aaaacattca aagggataga tctagatgaa   6900

ttgaatatgg tggcctacgg ggatgatgtg ttggctagtt accccttccc aattgactgt   6960

ctggaattgg caagaacagg caaggagtat ggtttaacta tgacccctgc cgacaagtca   7020

ccttgcttta atgaagttac atgggagaat gccactttct tgaagagagg attcttgcct   7080

gatcatcaat tcccgttcct catccacccc acgatgccaa tgagggagat tcacgaatct   7140

attcgttgga ctaaagatgc acgaagtact caagatcacg tgcgctctct ctgcttatta   7200

gcatggcaca acgggaaaga ggagtatgaa aaatttgtga gtacaatcag atcagttcca   7260

attggaaagg cattggctat accgaatttt gagaatctga gaagaaattg gctcgaattg   7320

ttttaaattt acagtttgta actgaaccct accagtaatc tggtcgtgtt aatgactggt   7380

gggggtaaat ttgttataac cagaatagca aaaaaaaaaa aaaaaaaaaa aaaa         7434
```

<210> SEQ ID NO 8
<211> LENGTH: 15
<212> TYPE: DNA
<213> ORGANISM: Artificial Sequence
<220> FEATURE:
<223> OTHER INFORMATION: Sequencing primer (F)
<220> FEATURE:
<221> NAME/KEY: misc_feature
<222> LOCATION: (2)..(2)
<223> OTHER INFORMATION: n is a, c, g, or t

<400> SEQUENCE: 8

```
cnayayaata tatta                                                       15
```

<210> SEQ ID NO 9
<211> LENGTH: 18
<212> TYPE: DNA
<213> ORGANISM: Artificial Sequence
<220> FEATURE:
<223> OTHER INFORMATION: Sequencing primer (R)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 9

```
anacnarrtt ncccatca                                                    18
```

<210> SEQ ID NO 10
<211> LENGTH: 7430
<212> TYPE: DNA
<213> ORGANISM: Enterovirus 71 Y90-3896 strain

<400> SEQUENCE: 10

```
ttaaaacagc ctgtgggttg cacccaccca cagggcccac tgggcgccag cactctggta     60

cttaggtacc tttgtgcgcc tgttttatct ccccttcccc gaagtaactt agaagctgtg    120

agctaacgat caacagtagg tgtgacatac cagtcatatc ttgatcaagc acttctgttt    180
```

-continued

```
ccccggactg agtatcaata ggctgctcgc gcggctgaaa gagaaaacgt tcgtcacccg    240
gccaactact tcgagaagct tagtaccacc atgaacgagg cagagtgttt cgctcggcac    300
aaccccagtg tagatcaggc tgatgagtca ctgcaatccc catgggcgac catggcagtg    360
gctgcgttgg cggcctgccc atggagaaat ccatgggacg ctctaattct gacatggtgc    420
gaagagccta ttgagctagc tggtagtcct ccggcccctg aatgcggcta atcctaactg    480
cggagcacac acccacaagc cagtgggcag tgtgtcgtaa cgggcaactc tgcagcggaa    540
ccgactactt tgggtgtccg tgtttccttt tattcttgta ttggctgctt atggtgacaa    600
tcaaagagtt gttaccatat agctattgga ttggccatcc ggtgtgcaac agagcaatta    660
tttacctatt tattggtttt gtaccattga cactgaagtc tgtgattacc cttaatttta    720
ttttgaccct caacacagtc aaacatgggc tcacaggtgt ccacacaacg ctccggctca    780
catgaaaact ctaactcagc tactgagggc tccaccataa actacactac tattaattac    840
tacaaggact cctatgccgc tacagcaggc aaacagagcc tcaagcagga tccagataag    900
tttgcaaatc ctgtcaaaga tattttcact gaaatggcag cgccactaaa gtccccatcc    960
gctgaagcat gtggatacag cgaccgagta gcgcagttaa ctattggcaa ctctaccatc   1020
actacacaag aagcagcaaa cattatagtt ggctatggtg aatggccctc ctactgctcg   1080
gattctgacg ctacagcagt ggacaaacca acgcgcccag atgtttcggt gaacaggttt   1140
tacacattgg acaccaaatt atgggagaaa tcgtccaagg gatggtactg gaaattcccg   1200
gatgtgttaa cagaaaccgg ggtttttggc cagaatgcac aattccatta cctctatcgg   1260
tcagggttct gcattcacgt gcaatgcaat gctagcaaat tccatcaggg agcgctccta   1320
gtcgctgttc tcccggagta tgtcattggg acagtggcgg gtggcacagg gacggaggat   1380
agccaccccc cttacaagca gactcaaccc ggcgctgatg gttttgagtt acaacatccg   1440
tacgtgcttg acgctggcat tccaatatca caattaacag tgtgcccaca tcagtggatt   1500
aacttgagga ccaacaattg tgccacaata atagtgccat acattaatgc actgcccttt   1560
gattctgcct taaaccattg taactttggc ctactggttg tgcccattag cccgttggac   1620
ttcgaccaag gagcgacgcc agtgatcccc attactatca cattggcccc aatgtgttct   1680
gaatttgcag gtcttaggca agcggtcacg caaggatttc ctactgagct gaaacctggc   1740
acaaaccaat ttttaaccac tgacgatggc gtttcagcgc ccattctgcc aaactttcac   1800
cccaccccat gcatccatat acctggtgag gttagaaatt tgctagagct atgccaggtg   1860
gagactatct tagaggtcaa caatgtaccc acgaatgcca ctagtttaat ggagagactg   1920
cgctttccgg tctcagccca agcaggaaaa ggcgagttgt gtgcagtgtt cagagccgat   1980
cctgggcgaa atgggccttg gcaatctacc ttgttgggcc agttgtgcgg gtactacact   2040
caatggtcag gatcactgga agtcacgttc atgttcactg ggtcctttat ggccaccggc   2100
aagatgctta tagcttacac gccaccagga ggccctttgc ccaaggaccg ggcgaccgcc   2160
atgttgggta cgcatgtcat ctgggatttt gggctgcaat cgtctgtcac ccttgtaata   2220
ccatggatca gcaacactca ttacagagcg catgctcgag atggggtgtt cgactattac   2280
actacaggcc tggttagtat atggtatcag acgaactatg tggttcccat tggagcaccc   2340
aatacagcct atataatagc gttagcggca gcccagaaga attttaccat gaaattgtgt   2400
aaggatgcca gtgatatctt acagacaggc actattcagg gggatagggt ggcagatgtg   2460
attgagagtt ctatagggga tagtgtgagc agagctctca ctcaagctct accggcaccc   2520
acaggccagg acacgcaggt aagcagccat cgattggata ctggcaaagt tccagcactc   2580
```

-continued

```
caagccgctg agattggagc atcatcaaat gctagtgatg agagtatgat tgagacacga   2640
tgtgttctta attcgcacag cacagctgag accactctcg atagtttctt cagcagagcg   2700
ggattagttg ggagatagga ccttcctctt gaaggcacaa ccaacccaaa tggttatgca   2760
aattgggaca tagatataac aggttatgcg cagatgcgta gaaaggtgga gctgttcacc   2820
tacatgcgtt ttgacgcaga attcaccttc gtcgcgtgca cgcccaccgg ggaggttgtc   2880
ccacaattac tccaatatat gtttgtgcca cctggggccc ccaagccaga atccagagaa   2940
tccctcgcat ggcaaactgc caccaatccc tcggtttttg ttaagctatc agacccccca   3000
gcgcaggttt cagttccatt catgtcacct gcgagtgctt accaatggtt ttatgacgga   3060
tatcccacgt tcggtgaaca caagcaggaa aaagaccttg aatacggggc atgtccaaac   3120
aacatgatgg gcacgttctc agtgcggacc gtaggaacct cgaagtccaa gtacccttta   3180
gtaattagga tttatatgag gatgaagcac gtcagggcat gggtacctcg tccaatgcgc   3240
aaccaaaact atctattcaa agccaaccca aattacgccg gcaactccat taagccaacc   3300
ggtgccagtc gcacagcgat caccactctc ggaaaatttg ggcaacaatc cggggccatc   3360
tatgtgggta actttagagt ggttaatcgc catcttgcca ctcacaatga ttgggcgaac   3420
cttgtttggg aagacagctc tcgcgactta ctcgtatcat ctaccaccgc tcagggttgt   3480
gatacgatag cccgttgcga ttgtcagaca ggagtgtact attgtaactc aaggagaaaa   3540
cactacccgg ttagtttctc aaaacccagc ttgatctttg tagaggccag cgagtactac   3600
ccagccaggt atcagtcaca cctcatgctc gcagtgggtc actcagaacc aggagattgc   3660
ggtggcatac tcagatgcca acacggtgtt gtagggatag tttctaccgg gggaaatggc   3720
ctggtggggt tcgccgacgt gagggacctt ctgtggttgg atgatgaagc catggaacag   3780
ggtgtgtctg attacattaa agggcttggt gatgctttcg gcatgggatt cacagacgca   3840
gtgtcaagag aggttgaagc cttgaaaagt catttgatcg gttcagaggg cgccgtggag   3900
aagattctta agaacttagt aaaactcatc tctgcgcttg tcattgtcat caggagtgac   3960
tacgacatgg tcacattgac ggcaacgctt gccctgattg ggtgccatgg gagcccttgg   4020
gcctggatta agtcgaaaac agcttcaatt ttgggtatac caatggccca gaagcagagc   4080
gcctcttggt taaagaagtt caacgatgcg gcgagtgccg ctaaggggct tgagtggatc   4140
tccaataaaa tcagtaaatt tatcgattgg ctcaaggaga aaatcatccc ggctgctaaa   4200
gaaaaagtcg aatttctaaa taacttgaag caacttcctt tattggaaaa ccaaatctct   4260
aaccttgaac agtcagcagc ttcgcaggag gaccttgaag cgatgtttgg caacgtgtcc   4320
tacttggccc acttttgccg caaattccaa cctctctatg ccacagaagc aaagagggtg   4380
tacgccttag aaaaaagaat gaacaattac atgcagttca agagcaaaca ccgtattgaa   4440
cctgtgtgct tgatcattag aggctcacct ggtactggga agtctttagc aacagggatt   4500
atcgctagag ctatagcaga taagtatcac tctagtgtgt attccctacc tccagaccca   4560
gatcattttg atggatataa acaacagatt gtcactgtta tggatgacct ctgccaaaat   4620
ccggatggga aagacatgtc actattctgt cagatggttt ccacagtgga ctttataccg   4680
cctatggcat ccctggagga gaagggagtc tcattcacct ccaagtttgt gattgcctcc   4740
actaacgcta gcaacatcat agtaccaaca gtctcggatt cagatgccat ccgtcgtcgg   4800
ttctttatgg actgtgatat tgaagtgacc gattcctata agacagattt gggtaggctt   4860
gatgcaggga gagcggccag gctgtgttct gagaacaaca ctgcaaattt caaacggtgc   4920
```

-continued

```
agcccactag tatgtgggaa agcaatccag cttagggata gaaagtccaa ggtgagatac   4980
agtgtggaca cagtggtgag tgagctcatt agggaatata acaacaggtc agctattggg   5040
aataccatcg aagctctttt tcaggggccc cctaaattca gaccgataag gattagtctg   5100
gaggagaagc ccgcacctga cgctatcagt gatctgctgg ctagtgttga tagtgaagaa   5160
gtccgccaat actgtagaga tcaaggatgg attgtgcctg atactcccac caacgttgag   5220
cgccacttga atagagctgt cttgattatg caatctgtag ccaccgtggt ggcagttgtg   5280
tcccttgttt acgtcatcta caagttgttt gccggtttcc aaggagcata ttccggcgcc   5340
cccaagcaaa cacttaagaa accggtgctg cgtacagcaa ccgtgcaggg accgagcttg   5400
gacttcgccc tatctttact cagaaggaac attaggcagg tccaaaccga tcagggccac   5460
ttcacaatgc taggagtgcg ggaccacttg gctgtactcc ctagacactc ccaaccagga   5520
aagaccattt gggttgagca caaactggtg aagatcgtag acgccgtgga gttggtagat   5580
gaacaagggg ttaacctaga gcttacactg gtaacgcttg acaccaatga aaaattcaga   5640
gacatcacaa ggttcatacc agaaacaatt agtcctgcta gtgatgccac tctagtcata   5700
aatactgaac atatgcccag catgtttgtg ccggttggag atgtggtcca gtatggattt   5760
ttgaatctta gtggcaagcc cactcaccgg actatgatgt acaacttccc aacaaaggca   5820
ggacagtgtg gtggtgttgt gactgctata ggtaaagtga ttgggatcca cattggtggt   5880
aatggtaggc aaggtttctg tgctgctctg aagagggggt acttttgtag tgaacagggt   5940
gagatccagt ggatgaagcc caacaaagaa actggcaggt tgaacatcaa tgggcctact   6000
cgcaccaagc ttgagccaag tgttttccat gatgtgttcg agggcaccaa agagccagca   6060
gtgctgacta gcaaagaccc aaggctggaa gtcgactttg agcaggcttt gttctcaaaa   6120
tatgtaggaa acacgcttca cgagcccgac gagtttgtca gggaggcggc tttgcactat   6180
gccaaccaac tcaaacagtt agatatcaaa accaccaaaa tgagcatgga ggatgcttgt   6240
tatggtacag agaacctgga agctatagat cttcacacta gtgcgggata cccatacagt   6300
gcactaggca ttaagaaaag ggatattttg gatccaataa ctcgtgatgt tagtaaaatg   6360
aaattctaca tggacaaata tgggttggat ctaccgtatt ccacttatgt caaagatgaa   6420
ctcagggcca ttgataagat caagaaaggg aagtcccgtc tcatagaagc gagcagtcta   6480
aatgactcag tgtacttaag gatgacattt gggcaccttt atgaaacctt ccacgccaat   6540
ccgggtacag tcactggttc agctgttgga tgcaacccag atgtgttttg gagtaagtta   6600
ccaattctac tcccaggatc gctttttgcg tttgactact cggggtatga cgccagtctc   6660
agcccagtgt ggtttagggc gttggagata gtcctgcggg aaattggata ctctgaggac   6720
gcagtgtctc tcatagaagg gatcaatcac acccaccatg tgtatcgcaa taaaacttat   6780
tgtgttcttg gggaatgcc ctcaggttgc tcaggcactt ccattttcaa ctcgatgatc   6840
aataatatca ttatcaggac actattgatt aaaacattca aagggataga tctagatgaa   6900
ttgaatatgg tggcctacgg ggatgatgtg ttagctagtt atcccttccc aattgactgt   6960
ctagagctgg caaagacagg caaggagtat ggcttgacta tgacccctgc cgacaaatca   7020
ccctgcttta atgaagttac gtgggagaat gccaccttct taaagagagg atttctgcct   7080
gatcatcaat ttccgttcct catccaccct acgatgccaa tgaaggaaat tcacgagtcc   7140
attcgctgga ccaaagacgc acgaaatacc caagatcacg tgcgctccct ctgcttgtta   7200
gcatggcaca acgggaaaga ggagtatgaa aaatttgtga gcgcaatcag atcggttcca   7260
attgggaaag cgttagccct accaaatttt gagaatctga ggagaaattg gctcgaattg   7320
```

ttttaaattt acagtttgta actgaacccc accagaaatc tggtcgcgtt aatgactggt 7380
gggggtaaat ttgttataac cagaatagca aaaaaaaaaa aaaaaaaaaa 7430

<210> SEQ ID NO 11
<211> LENGTH: 7433
<212> TYPE: DNA
<213> ORGANISM: Enterovirus 71 N772 strain

<400> SEQUENCE: 11
ttaaaacagc ctgtgggttg tacccactca cagggcccac tgggcgctag cactctggta 60
tctcggtacc tttgtgcgcc tgttttatac cccccccccc tcagtgaaac ttagaagcag 120
caaacaacga tcaatagcag acataacact ccagttatgt ctcgatcaag cacttctgtt 180
tccccggacc gagtatcaat agactgctcg cgcggttgaa ggagaaaacg ttcgttatcc 240
ggctaactac ttcgggaaac ctagtaacac catgaaagtt gcggagagct tcgttcagca 300 ctccccccagt gtagatcagg tcgatgagtc accgcattcc ccacgggcga ccgtggcggt 360
ggctgcgttg gcggcctgcc catggggtaa cccatggggc gctctaatac ggacatggtg 420
cgaagagtct actgagctag ttagtagtcc tccggcccct gaatgcggct aatcccaact 480
gcggagcaca cgcccacaag ccagcgggta gtgtgtcgta acgggcaact ctgcagcgga 540
accgactact ttgggtgtcc gtgtttcctt ttatctttat attggctgct tatggtgaca 600
attaaagaat tgttaccata tagctattgg attggccatc cggtgtgcaa cagagcaatt 660
gtttacctat ttattggttt tgtaccattg accttgaagt ctgtgattac ccttagttat 720
atcttgaccc tcaacacagc taaacatggg ttcgcaggtg tctacacagc gctccggttc 780
tcacgaaaac tcaaactcag ccactgaagg ttccaccata aactacacca ccattaatta 840
ctacaaagac tcctatgctg ccacagcagg caaacagagt ctcaagcagg atccagacaa 900
gtttgcaaat cctgttaaag acatcttcac tgaaatggca gcgccactga aatctccatc 960
cgctgaggca tgtggataca gcgatcgagt ggcgcaatta accattggca actccaccat 1020
caccacgcaa gaagcggcta acatcatagt tggttatggt gagtggcctt cctactgctc 1080
ggattctgac gctacagcag tggataaacc aacgcgcccg gatgtttcag tgaacaggtt 1140
ttatacattg gacaccaagt tgtgggagaa atcgtccaag ggatggtact ggaagttccc 1200
ggatgtgtta actgaaaccg gggtttttgg gcaaaatgca caattccact acctctaccg 1260
atcagggttc tgtattcacg tgcagtgcaa tgctagtaaa tttcaccaag gagcactcct 1320
agttgctgtc ctaccagagt acgtcattgg gacagtggct ggcggtacag ggacggaaga 1380
cagtcaccct ccttacaagc agactcaacc cggcgccgat ggcttcgaat tgcaacaccc 1440
gtacgtgctt gatgctggca tcccaatatc acagttaaca gtgtgcccac accagtggat 1500
taatttgagg accaacaatt gtgctacaat aatagtgcca tacattaacg cactaccttt 1560
tgattctgct ttgaaccact gtaactttgg cctattagtt gtgcctatta gcccgctaga 1620
ttacgaccaa ggagcgacgc cagtaatccc tataactatc acattggccc caatgtgttc 1680
tgaattcgca ggtctcaggc aagcagtcac gcaagggttt cccaccgagc tgaaacctgg 1740
cacaaatcaa tttttaacca ctgatgatgg cgtttcggca cctattctac caaacttcca 1800 ccccacccccc tgtatccaca tacctggtga agttaggaac ttgctagagt tatgccaggt 1860
ggagaccatt ttggaggtca acaatgtgcc cacgaatgcc actagcttaa tggagaggct 1920
gcgctttccg gtctcagcac aagcagggaa aggcgagctg tgtgcggtgt tcagagccga 1980

-continued

```
tcctgggcga aatggaccgt ggcagtccac cttgctgggt cagttgtgcg ggtattatac   2040
ccaatggtca ggatcattgg aggtcacctt catgttcact ggatccttca tggctactgg   2100
caagatgctc atagcctata caccgccggg aggccctttg cccaaggacc gggcaaccgc   2160
catgttgggc acgcacgtca tctgggattt tgggctgcaa tcgtctgtta cccttgtgat   2220
accatggatc agcaacactc actacagagc gcatgcccga gatggagtgt ttgactacta   2280
caccacaggg ttagtcagta tatggtatca gacaaattac gtggttccaa ttggggcgcc   2340
caatacagcc tatataatag cattagcggc agcccaaaag aacttcacta tgaaattgtg   2400
caaggatgct agtgatatcc tgcagacggg caccatccag ggagataggg tggcagatgt   2460
aattgagagt tccatagggg atagtgtgag cagagccctc actcaagctc taccagctcc   2520
cacaggccag aacacacagg tgagcagtca tcgactggat acaggtaagg ttccagcact   2580
ccaagctgct gagattggag catcatcaaa tgctagtgat gagaacatga ttgagacacg   2640
ctgtgttctt aactcgcaca gcacagctga gaccactctt gatagtttct tcagcagagc   2700
gggattagtt ggagagatag atctccccct tgaaggcaca accaacccaa atggctatgc   2760
caactgggac atagatataa caggttacgc gcaaatgcgt agaaaggtgg agctattcac   2820
ctacatgcgc tttgatgcag agttcacttt tgttgcgtgc acacccaccg ggaagttgt    2880
cccacaattg ctccaatata tgtttgtgcc acctggagcc cctaagccag attccaggga   2940
atcccttgca tggcaaactg ccaccaaccc ctcagttttt gtcaagctgt cagaccctcc   3000
agcgcaggtt tcagtaccat tcatgtcacc tgcgagtgct taccaatggt tttatgacgg   3060
atatcccaca tttggagaac ataaacagga gaaagatctt gaatatgggg catgtcctaa   3120
caacatgatg ggcacgttct cagtgcggac tgtagggact tccaagtcca aatacccttt   3180
agtggttagg atttacatga gaatgaagca cgtcagggcg tggatacctc gcccgatgcg   3240
caaccaaaac tacctattca aagccaaccc aaattatgct ggcaactcca ttaagccaac   3300
tggtaccagt cgcacggcga tcactactct tgggaaattt gggcaacagt ctggggccat   3360
ttacgtgggt aactttagag tggttaaccg tcatcttgcc actcataatg attgggcaaa   3420
tcttgtttgg gaagacagct ctcgcgactt gctcgtgtca tccaccactg cccaaggttg   3480
tgacacgatt gcccgttgca attgccagac aggggtgtac tattgtaatt caagaagaaa   3540
acactaccca gtcagttttt caaaacccag cctgatctat gtagaggcta gcgagtatta   3600
cccagccagg taccagtcac atctcatgct cgcacagggc cactcagaac ctggtgattg   3660
tggtggtatc cttagatgcc aacatggtgt cgtcggtata gtgtctactg gtggcaatgg   3720
gctcgttggc tttgcagacg tcagggacct cttgtggtta gatgaagaag ctatggagca   3780
gggcgtgtcc gactacatca agggtctcgg agatgctttc gggacaggtt tcactgatgc   3840
agtctcaagg gaggttgaag ctctcaagaa ctatcttata gggtctgaag gagcagttga   3900
aaaaattcta aaaaatctta ttaaactaat ctctgcactg gtgattgtaa tcagaagtga   3960
ttacgacatg gttaccctta ctgcaaccct agcgctgata ggttgtcatg gcagtccttg   4020
ggcttggatc aaagccaaaa cagcttctat cttaggcatc cctatcgctc agaagcaaag   4080
cgcttcttgg ctcaagaaat tcaatgacat ggccaacgct gctaaggggt tagagtgggt   4140
ttctaataag atcagcaaat tcattgattg gcttaaggag aaaatagtac cagcagctaa   4200
ggagaaggtt gaattcctaa ataacttgaa acagttgcca ttgctagaga atcagatctc   4260
aaacttggaa caatctgctg cctcacaaga ggaccttgaa gtcatgtttg ggaatgtgtc   4320
gtatctagcc cacttctgtc gcaagttcca gccgctatac gccacggaag ctaaaagggt   4380
```

ttatgccctg gagaagagaa tgaataacta tatgcagttc aagagcaaac accgaattga 4440
acctgtatgt cttattatta ggggctcacc aggcactggg aagtctttag ccactggtat 4500
cattgctcga gcaatcgctg acaagtacca ctccagcgtg tactcgcttc caccagaccc 4560
agatcatttt gatggctaca agcaacaggt ggttacagtg atggatgact tgtgtcaaaa 4620
ccccgatggc aaggatatgt ccttattctg tcaaatggta tccaccgtag acttcatccc 4680
accaatggct tctcttgagg agaagggagt ttccttcacc tctaagtttg ttatcgcatc 4740
tactaatgcc agtaacatca tagtgccaac agtgtctgac tctgacgcta ttcgccgcag 4800
gttctacatg gattgtgata ttgaagtgac agactcgtac aaaactgatc taggtagact 4860
ggatgcaggg cgagccgcca aactgtgctc tgagaacaac actgcaaatt tcaaacgttg 4920
cagcccatta gtgtgtggga aagctatcca acttagagat agaaagtcta aagttagata 4980
cagtgtggat acagtagttt cagaacttat tagggaatac agtaataggt ccgccattgg 5040
caacacaatc gaggctcttt tccaaggtcc acccaagttc aggccaatta ggattagcct 5100
tgaagagaaa ccagctccgg acgctattag cgatctcctt gctagtgtag atagtgaaga 5160
agtgcgccaa tactgcaggg atcaaggctg gatcattcct gaaactccca ccaacgtaga 5220
gcggcacctt aatagagcag tgcttgtcat gcaatccatc accacagtag tggcggttgt 5280
ctcgttggtg tatgtcatct acaagctctt tgcagggttt cagggtgcgt actctggtgc 5340
tcctaagcaa gtgcttaaga aacctgctct tcgcacagca acagtacagg gcccgagcct 5400
tgattttgct ctctccctgt tgaggaggaa catcaggcaa gtccaaacag accaggggca 5460
tttcaccatg ttgggtgtta gggatcgttt agcagtcctc ccgcgtcact cacaacccgg 5520
taaaactatt tggattgagc ataaactcgt gaacatcctt gatgcagttg aattggtgga 5580
tgagcaagga gtcaacctgg aattaaccct catcactctt gacactaacg aaaagtttag 5640
ggatatcacc aaattcatcc cagagaatat tagcactgcc agtgatgcca ctctagtgat 5700
caacacggag cacatgccct caatgtttgt cccggtgggt gacgttgtgc agtatggctt 5760
cttgaatctc agtggtaagc ctacccatcg caccatgatg tacaactttc ctactaaagc 5820
agggcagtgt ggaggagtgg tgacatctgt cgggaaggtt atcggtattc acattggtgg 5880
caatggtaga caaggttttt gcgcaggcct caaaaggagt tactttgcta gtgaacaagg 5940
agagatccag tgggttaagc ccaataaaga aactggaaga cttaacatca atggaccaac 6000
ccgcaccaag ttagaaccca gtgtattcca tgatgtcttc gagggaaata aggaaccagc 6060
tgtcttgcac ggtaaagatc cccgactcga ggtagatttt gagcaggccc tgttctctaa 6120
gtatgtggga aatacactat atgagcctga cgagtacatc aaagaggcag ccccttcatta 6180
tgcaaatcaa ttaaagcaac tagaaattaa tacctctcaa atgagcatgg aggaggcctg 6240
ctacggtact gagaatcttg aggctattga tcttcatact agtgcaggtt accccctatag 6300
tgccctggga ataaagaaaa gagacatctt agaccctacc accagggacg tgagtaaaat 6360
gaagttctac atggacaaat acggtcttga tctcccttac tccacttatg tcaaggatga 6420
gctgcgctca attgataaaa ttaggaaagg gaagtcccgt ctgatcgagg ccagtagttt 6480
aaatgattca gtgtacctca gaatgacttt cggccatttg tatgaggctt tccacgcaaa 6540
tcctgggacg ataactggat cagccgtggg gtgtaaccct gacacattct ggagcaaact 6600
gccaatcttg ctccctggtt cactctttgc ctttgactac tcaggttatg atgctagcct 6660
tagccctgtc tggttcagag cattagaatt ggtccttagg gagatagggt atagtgaagg 6720

```
cgcagtctca ctcattgagg gaatcaacca cacacaccat gtgtatcgca atacgaccta   6780

ctgtgtgctt ggtgggatgc cctcaggctg ttcgggaaca tccattttca actcaatgat   6840

caacaacatt attatcaggg cactgctcat aaaaacattt aagggcattg atttggacga   6900

actcaacatg gtcgcttatg gagatgatgt gctcgccagc taccccttcc caattgattg   6960

cttggaatta gcaaagactg gcaaggagta tggtctaacc atgactcctg cagataagtc   7020

tccttgcttt aatgaagtta attggggtaa tgcgaccttc ctcaagaggg gctttctacc   7080

cgatgaacag tttccgtttt tgatccaccc tactatgcca atgagggaga tccatgaatc   7140

cattcgatgg accaaagacg cacgaaacac tcaagatcat gtgcgatctt tgtgcctcct   7200

agcatggcat aatggtaagc aagaatatga gaaatttgtg agcacaatta ggtctatccc   7260

agtaggaaga gcgttggcca tcccaaatta tgaaaatctt agacgcaatt ggctcgagtt   7320

attttagagg ctacacgtac ctcaacccca ccagaaatct ggtcgtgaat atgactggtg   7380

ggggtaaatt tgttataacc agaatagcaa aaaaaaaaaa aaaaaaaaaa aaa          7433
```

<210> SEQ ID NO 12
<211> LENGTH: 7448
<212> TYPE: DNA
<213> ORGANISM: Enterovirus 71 C7/Osaka strain

<400> SEQUENCE: 12

```
ttaaaacagc ctgtgggttg cacccactca cagggcccac gtggcgctag cactctgatt     60

ccacggaacc tttgtgcgcc tgttttacgc cccctcccca atttgcaact tagaagcaat    120

acacaacact gatcaacagc aggcatggca caccagctat gtcttgatca agcacttctg    180

tttccccgga ccgagtatca atagactgtt cacgcggttg aaggagaaag cgtccgttat    240

ccggctaact acttcgagaa acctagtagc accattgaag ctgcagagtg tttcgctcgg    300

cacttccccc gtgtagatca ggtcgatgag tcactgcaat ccccacgggc gaccgtggca    360

gtggctgcgc tggcggcctg cctatggggc aacccatagg acgctctaat gtggacatgg    420

tgcgaagagt ctattgagct agttagtagt cctccggccc ctgaatgcgg ctaatcctaa    480

ctgcggagca catgccttca atccagaggg tggtgtgtcg taatgggcaa ctctgcagcg    540

gaaccgacta ctttgggtgt ccgtgtttcc ttttattctt acattggctg cttatggtga    600

caattgcaga attgttacca tatagctatt ggattggcca tccggtgtgc aatagagcta    660

ttatatacct atttgttggc tttgtaccac taaccttaaa atctataacc accctcgact    720

ttatattaac cctcaataca atcaaacatg ggctcacagg tgtctactca gcgatccggt    780

tcccacgaga actccaattc agctacagaa ggctccacca ttaattacac taccatcaac    840

tattacaaag actcctatgc tgcgacagcg ggcaaacaaa gcctcaaaca agaccctgat    900

aagtttgcta accctgtcaa ggacattttc actgaaatgg ctgcgccact gaagtctcca    960

tccgctgaag cttgtggtta cagtgatcgc gtggcacaac tcaccattgg aaactccacc   1020

attactacac aggaggcggc aaacatcata gtcggttatg gtgagtggcc ctcatactgc   1080

tctgatgacg atgctacagc ggtggacaaa ccaacgcgcc cagatgtttc agtgaatagg   1140

ttttacacat tggacactaa actgtgggaa aaatcatcca aggggtggta ttggaagttt   1200

cctgatgtgt tgactgagac cggagtcttt ggccagaacg cacagtttca ctatttatat   1260

agatcagggt tttgcattca tgtacaatgt aatgctagca agttccatca aggagcgctg   1320

ttagtcgcta tacttccaga gtatgttata gggacagtag caggcggcac aggaacagag   1380

gacagccacc ctccttacaa acaaacacag cctggcgccg acggttttga gctgcagcac   1440
```

ccgtacgtgc tcgatgctgg gattcctata tcacaattga cagtctgccc ccatcaatgg 1500
attaacctgc ggaccaataa ctgtgccaca ataatagtgc catatatgaa tacactgcct 1560
ttcgactctg ccctgaacca ttgcaatttt gggctgttgg tagtgcccat tagcccatta 1620
gactttgacc aaggggcaac tccggttatc cctattacaa tcactctagc tccaatgtgc 1680
tctgagtttg caggtctcag acaggcagtc acacaaggct ttcccactga gccaaaacca 1740
ggaacgaatc aattcttgac caccgatgac ggcgtctcgg cgcccattct accaaatttc 1800
caccccactc catgtattca catacccggt gaagtcagaa acctgcttga gttgtgtcaa 1860
gtggagacta ttcttgaggt taacaacgta cccaccaatg ctactagtct gatggaaagg 1920
ctacgattcc cagtgtccgc gcaagcgggg aaaggtgaat tgtgtgccgt gtttagggcc 1980
gaccctggaa gagacggccc atggcaatca acaatgctgg gccagttgtg tggatattac 2040
acccagtggt cagggtcact ggaggtcact tttatgttta ccgggtcatt catggccacg 2100
ggtaaaatgc tcatagctta cacacctcct ggcggcccat tacctaaaga tcgggccaca 2160
gcaatgctgg gcacacatgt tatctgggat tttgggctac aatcatctgt caccccttgta 2220
ataccatgga tcagcaacac ccactacagg gcgcatgccc gggatggagt gttcgattac 2280
tataccacag gactggtcag tatctggtat caaacaaact atgtagttcc aattggggca 2340
cccaacacag cttacataat agcactagcg gcagcccaga agaattttac catgaaactg 2400
tgcaaagaca ccagccacat attacagaca gcctctattc agggagatag ggtggcagat 2460
gtgatcgaga gctctatagg agatagtgtg agtagggcac ttacccaggc cctgccagca 2520
cccacaggtc aaaacacaca ggtgagtagt catcgactag acactggcga agttccagcg 2580
ctccaagctg ctgaaattgg ggcatcgtca aatactagtg atgagagtat gattgaaaca 2640
cgatgcgttc ttaactcaca cagtacagcg gagaccacct tggacagctt cttcagtagg 2700
gcaggtttgg taggagagat agatctccct cttgagggta ccactaatcc aaatggttat 2760
gccaactggg acatagacat aactggttac gcacaaatgc gcagaaaagt ggagctgttc 2820
acctacatgc gctttgatgc ggaattcact tttgttgcgt gcactcctac tggtgaggtt 2880
gttccacaat tactccagta tatgtttgtt ccccctggtg ctcccaaacc agagtctaga 2940
gagtcacttg cttggcagac agccacaaac ccctcagttt ttgtcaagtt gactgatccc 3000
ccggcacagg tctcagttcc gtttatgtca cccgcgagcg cttaccagtg gttttacgac 3060
gggtacccca cgtttggaga acataaacag gagaaagacc ttgagtatgg agcgtgtcct 3120
aataatatga tgggcacttt ctcggtgcga accgtggggt cattaaagtc caagtaccct 3180
ttggttgtca gaatatatat gagaatgaag catgtcaggg cgtggatacc tcgcccgatg 3240
cgcaaccaaa actacttgtt caaagccaac ccaaactatg ccggtaactc cattaaaccg 3300
accggcacta gtcgtactgc cattactacc cttggaaagt tcggccagca atctggggcc 3360
atctacgtgg gcaacttcag agtggttaat cgtcacctcg ctactcacaa tgactgggcg 3420
aatctcgtct gggaagacag ctcccgcgac ctattagtat cgtctaccac cgcccagggc 3480
tgtgacacaa ttgcacgttg tgactgtcaa acaggagtgt actattgtaa ctccaagaga 3540
aagcactacc cagtcagctt ctctaaaccc agcctcatat atgtggaagc tagcgagtat 3600
taccctgcta gataccaatc gcacctgatg cttgcagcgg gccactctga gcccggtgac 3660
tgcggaggca tcttaaggtg tcaacatggt gtagttggta tagtgtccac gggtggcaac 3720
gggctcgttg gttttgctga tgtgagggat ctcttgtggt tagatgaaga ggccatggag 3780

-continued caaggtgtgt ccgactatat taaggggctc ggtgacgcgt ttggaacagg cttcaccgat 3840
gctgtatcca gggaagttga agcccttagg aaccacctca tagggtctga tggagcagtt 3900
gagaaaatcc taaagaacct tatcaagctg atttcagcgt tagtaattgt gatcaggagt 3960
gattatgata tggtcaccct cacagcaact ttagccctga ttggttgtca tggaagtcct 4020
tgggcttgga ttaaagccaa aacagcatcc attttaggta tccccatcgc ccagaagcag 4080
agtgcttctt ggctaaagaa atttaatgat atggcgagtg ccgccaaggg tttagaatgg 4140
atatccaaca aaattagtaa gttcattgac tggctcaggg agaagattgt tccagcagct 4200
aaggagaaag cagaattttt aaccaatttg aagcaattac cactgttaga gaaccagatc 4260
acgaatttag agcagtccgc tgcctcacaa gaggaccttg aagctatgtt tgggaatgtg 4320
tcatacctcg cccatttctg tcgcaagttc caaccattat acgctacgga agctaagcga 4380
gtctatgttc tagagaagag aatgaacaac tacatgcagt tcaagagcaa acaccgtatt 4440
gaacctgtat gtctcatcat tagaggctca ccgggcactg gaaagtccct tgcgaccggt 4500
atcattgctc gggccatagc agacaagtat cactctagtg tgtactcact tccaccagat 4560
cctgaccatt ttgacgggta caaacagcaa gtggtcacag ttatggatga tctgtgtcaa 4620
aatcctgacg gcaaagacat gtcattattt tgccagatgg tgtccaccgt ggattttatc 4680
ccaccaatgg cttctctcga agaaaaggga gtttctttca catctaaatt tgttatcgca 4740
tctaccaacg ccagcaacat tatagtgcct acagtgtctg actctgacgc cattcgtcgc 4800
aggttttaca tggattgcga cattgaggtg acagactcat acaaaacaga cttgggtaga 4860
ctagacgctg gacgggctgc taagttatgc tctgaaaaca acaccgcaaa cttcaaacga 4920
tgcagcccac tagtgtgtgg gaaagctatt caacttaggg acaggaagtc taaggtcagg 4980
tacagcgtgg acacagtggt ttctgaactt attagagaac acaatagcag atccgctatt 5040
ggtaacacaa ttgaagcact attccaaggc ccacccaagt tcaggccaat tagaatcagt 5100
cttgaagaga agccagcccc agacgctatt agcgatctcc tcgctagtgt agacagcgag 5160
gaagtgcgcc aatactgtag ggagcaaggc tggatcatcc ctgaaactcc caccaatgtt 5220
gaacgacatc ttaatagagc agtgctagtc atgcaatcca tcgctactgt ggtggcagtc 5280
gtctcactgg tgtacgtcat ttacaagctc tttgcggggt ttcaaggtgc gtattctgga 5340
gctcccaagc aaatgctcaa gaaacctgtc ctccgcacgg caacagtaca gggtccgagt 5400
cttgactttg ctctatcctt gctgagaagg aacatcaggc aagtccaaac agatcaaggg 5460
cattttacta tgttaggtgt cagggatcgc ttggccgttc tcccacggca ctcacagccc 5520
gggaagacta tttgggtgga gcataaactt gtgaacatcc ttgacgcaat cgagctggtg 5580
gatgagcagg gcgttaattt ggaactcaca ttggtgacac tagatactaa tgaaaaattt 5640
agagatatca ccaagttcat tccagagacc attagcggcg ctagtgatgc aactttagtg 5700
atcaacacag aacatatgcc atcaatgttt gtcccagtgg gggacgttgt gcagtacggg 5760
ttcttgaacc ttagtggaaa gccaactcat aggaccatga tgtacaattt ccctacaaaa 5820
gcaggacagt gtggaggtgt ggtcacatca gtcggtaaga ttgtcggtat ccacattggc 5880
ggcaacgggc gccaggggtt ctgtgctggt ctgaagagga gttacttcgc aagtgtgcag 5940
ggtgagatcc aatgggtgaa gcctaacaag gaaactggta gactgaacat caatggacca 6000
actcgcacta agttggagcc tagcgtattt catgatgtgt ttgaaggcaa taaggaacca 6060
gcagttttaa caagtaaaga ccctagattg gaggtcgact ttgagcaagc cctgttttcc 6120
aagtatgtgg gcaatgtttt acacgagccc gatgaatatg tgactcaagc tgccctccac 6180

```
tatgcgaatc aacttaaaca attggacata aacactagca agatgagcat ggaggaagcg   6240

tgctatggca ctgaaaacct ggaagcaata gacctctgca ctagtgccgg atatccatac   6300

agcgcccttg gcattaagaa aagagacatt ctcgacccca caaccaggga tgtgtctaag   6360

atgaaattct atatggataa atacgggcta gatctgccat actctaccta tgtaaaggat   6420

gagcttaggt ccctggataa aatcaagaaa ggaaagtcac gcctgataga ggctagtagc   6480

ttgaatgact ctgtctacct cagaatgact tttgggcacc tttacgaagt gtttcatgct   6540

aaccctggca ctgtgactgg ctcagcagtg ggttgcaacc cggacgtgtt ttggagcaaa   6600

ctaccgattc tgctgcctgg gtcactcttt gccttcgact actcaggata tgatgctagt   6660

ctcagcccgg tatggttcag ggctctagaa gttgtgttac gggagattgg gtattcagag   6720

gaggccgtgt ccctaataga aggaatcaac cacacccacc atgtgtaccg gaacaaaaca   6780

tactgtgtac ttggtggaat gccctcaggg tgttctggta cttccatctt taatacaatg   6840

atcaacaaca tcatcattag aacccttttg atcaaaacct ttaagggaat agacctggat   6900

gagttgaaca tggtggccta tggggacgat gtgctggcta gttacccctt tcctattgat   6960

tgccttgagt tggctaagac tggcaaagag tatggtttga ccatgacacc tgcagacaaa   7020

tcaccctgtt tcaatgaagt aacatgggaa aatgctacct tcctgaagag agggttcttg   7080

ccagaccacc aatttccatt cttaattcac cctacgatgc ccatgagaga gatccatgag   7140

tccattcgat ggactaaaga cgcgcgcaac acccaagatc acgtgcgctc cctgtgtctg   7200

ttggcatggc acaatggtaa ggatgaatat gagaagtttg tgagtgcaat tagatcagtt   7260

ccagttggaa aagcgttggc cattcctaac tttgagaatc tgagaagaaa ttggctcgaa   7320

ttgttttaat attacagctt aaagctgaac cccactagaa atctggtcgt gttaatgact   7380

agtgggggta aatttgttat aaccagaata gcaaaaaaaa aaaaaaaaaa aaaaaaaaaa   7440

aaaaaaaa                                                            7448
```

<210> SEQ ID NO 13
<211> LENGTH: 7434
<212> TYPE: DNA
<213> ORGANISM: Enterovirus 71 2716-Yamagata-03 strain

<400> SEQUENCE: 13

```
ttaaaacagc ctgtgggttg cacccactca caggacccac gtggtgctag cactctggtt     60

ctacggaacc cttgtgcgcc tgttttacgc cccctcccca atttgcaact tagaagcaat    120

tcacaacact gatcaatagc aggcatggcg caccagctat gtcttgatca agcacttctg    180

tttccccgga ccgagtatca atagactgtt cacgcggttg aaggagaaag cgtccgttat    240

ccggctaact acttcgagaa acccagtagc gccattgaaa ctgcagagtg tttcgctcca    300

cacttccccc gtgtagatca ggtcgatgag tcactgcaat ccccacgggc gaccgtggca    360

gtggctgcgc tggcggcctg cctatggggc aacccatagg acgctctaat gtggacatgg    420

tgcgaagagt ctattgagct agttagtagt cctccggccc ctgaatgcgg ctaatcctaa    480

ctgcggagca catgccttca atccagaggg tagtgtgtcg taatgggcaa ctctgcagcg    540

gaaccgacta ctttgggtgt ccgtgtttcc ttttattctc acattggctg cttatggtga    600

caattacaga attgttacca tatagctatt ggattggcca tccggtgtgc aatagagcta    660

ttatatacct atttgttggt tttgtaccac taaccttaaa atctgcaacc actctcgact    720

atatattaac cctcaataca atcaaacatg ggctcacagg tgtccactca acgatccggc    780
```

-continued

```
tcccatgaaa actccaattc agctacagaa ggctccacca ttaattacac cactattaac    840
tattacaaag actcctatgc tgcgacagcg ggcaagcaga gcctcaaaca agaccctgat    900
aagtttgcta accctgtcaa ggacattttc actgaaatgg ctgcgcctct aaagtctcca    960
tccgctgaag cttgtggcta cagtgatcgc gtggcacaac tcaccattgg aaactccacc   1020
atcactacac aggaagcggc aaacatcata gtcggttatg gtgaatggcc ctcatactgc   1080
tctgatgacg acgctacagc ggtggataag ccaacgcgcc cagatgtttc cgtgaatagg   1140
ttttatacat tggacactaa actatgggaa aagtcatcca aggggtggta ttggaagttt   1200
cctgacgtat tgactgagac cggagtcttt ggccaaaacg cacagtttca ctatttatat   1260
agatcagggt tttgcatcca tgtgcaatgt aacgctagca agttccacca aggagcgctg   1320
ttagtcgcta tacttccaga gtatgtcata gggacagtgg cgggcggcac aggaacagag   1380
gacagtcacc ctccttacaa acaaacacaa ccaggtgccg acggttttga attgcagcac   1440
ccgtatgtgc tcgatgctgg gatccctata tcacaattga cagtatgccc ccatcaatgg   1500
attaacttac ggactaataa ctgtgccaca ataatagtgc catatatgaa tacactgcct   1560
tttgactccg ccctgaacca ttgcaatttt gggctgttgg tagtacccat tagcccatta   1620
gattttgacc aaggggcaac tccggttatc cctattacaa tcactctagc tccaatgtgc   1680
tccgaatttg ctggtctcag gcaggcagtc actcaaggct ttcccactga gccaaaacca   1740
gggacgaatc aattcttgac caccgatgat ggcgtctcag cacccattct accaaatttc   1800
catcccactc catgtattca catacccggt gaagtcagaa acctgcttga gttgtgtcaa   1860
gtggagacta ttcttgaggt taacaacgta cccaccaatg ctactagttt gatggaaaga   1920
ctacgattcc cggtgtccgc gcaagcgggg aaaggtgaat tgtgtgccgt gtttagggct   1980
gatcctggaa gagacggtcc atggcagtca acgatgctgg gccagttgtg tggatactac   2040
actcagtggt cagggtcact ggaggtcact ttcatgttca ccgggtcttt catggccacg   2100
ggtaagatgc tcatagctta tacacccccct ggcggtccct tacccaaaga tcgggctaca   2160
gcaatgctgg gcacacatgt tatctgggac tttgggctac aatcatctgt caccccttgtg   2220
ataccatgga tcagtaacac tcactacagg gcgcatgccc gggatggagt gttcgactac   2280
tataccacag gactggtcag tatctggtat caaacaaatt atgtagtccc aattggggca   2340
cccaacacag cttacataat agcactggcg gcggcccaga agaattttac catgaaactg   2400
tgcaaagaca ctagtcacat actacagaca gcctctattc agggagatag ggtggcagat   2460
gtgatcgaga gctctatagg ggacagcgtg ggtagggcac tcacccaggc cctgccagca   2520
cccacaggtc aaaacacaca ggtgagcagc catcgactag acactggtga agttccagcg   2580
ctccaagctg ctgagatcgg ggcatcgtca aatactagtg atgagagtat gattgagaca   2640
cgatgcgtcc ttaactcaca cagtacagca gagactaccc tggacagttt ctttagcaga   2700
gcaggtttgg taggagagat agatctccct ctagagggta ctaccaatcc aaatggttat   2760
gccaactggg atatagacat aactggttat gcacaaatgc gcaggaaagt ggagctgttc   2820
acctatatgc gctttgatgc ggaattcact ttcgttgcgt gcactcctac tggtgaggtt   2880
gttccacaac tactccagta tatgtttgtt ccccctggtg ctcctaaacc agagtctaga   2940
gaatcacttg cttggcagac agccacaaac ccttcagttt ttgtcaaatt aactgatccc   3000
ccggcacagg tctcagttcc gttcatgtca cccgcgagcg cttatcagtg gttttacgac   3060
gggtacccca cgtttggaga acacaaacag gagaaagatc ttgaatatgg agcgtgtcct   3120
aacaacatga tgggcacttt ctcggtgcgg accgtggggt cttcgaaatc caagtaccct   3180
```

```
ttggttgtca gaatatacat gagaatgaag catgtcaggg catggatacc tcgcccgatg   3240
cgcaaccaaa attacttgtt caaagccaat ccaaattatg ccggcaactc cattaagccg   3300
accggtacta gtcgtaccgc tattactacc cttggaaagt tcggccagca atctggggcc   3360
atctacgtgg gcaacttcag agtggttaat cgtcacctcg ctactcataa tgactgggca   3420
aacctcgttt gggaagacag ctcccgcgac ctattagtgt cgtctaccac cgcccagggc   3480
tgtgatacaa ttgcacgttg tgactgtcaa acaggagtgt actattgtaa ctccaagaga   3540
aagcactatc cagtcagctt ttctaaaccc agcctcatat atgtggaagc tagcgagtat   3600
taccctgcta ggtaccagtc gcacctgatg cttgcagcgg gccactctga gcccggcgac   3660
tgcggaggca tcttgaggtg tcaacatggt gtagttggta tagtgtccac gggtggcaac   3720
ggactcgttg gctttgctga tgtgagggac ctcttgtggt tagacgaaga agtcatggag   3780
caaggtgtct ccgactacat taaggggctt ggtgacgcgt ttgggacagg cttcaccgat   3840
gctgtgtcca gggaagttga agcccttagg aaccacctta taggatctga tggagcagtt   3900
gagaaaatcc taaagaacct tattaagctg atttcagcgt tagtaattgt gatcaggagc   3960
gattatgata tggtcaccct cacagctact ttagccctga ttggttgcca tggaagtcct   4020
tgggcttgga tcaaagccaa gacagcatcc attttaggca tccccattgc ccagaagcag   4080
agtgcttctt ggctaaagaa gttcaatgat atggcgagtg ccgccaaggg tttagagtgg   4140
atatccaaca aaattagtaa attcattgac tggctcagag agaagattgt tccagcagct   4200
agagagaaag cagaattctt aaccaacttg aagcaattgc cactgttaga gaaccagatc   4260
acgaatttag aacagtccgc tgcctcacaa gaggaccttg aagccatgtt tgggaatgtg   4320
tcatacctcg ctcatttctg tcgcaagttc caaccattat acgccacaga agctaagcgg   4380
gtctatgttc tagagaagag aatgaacaac tacatgcagt tcaagagcaa acaccgtatt   4440
gaacctgtat gtcttatcat tagaggctca ccaggcactg ggaagtccct tgcgaccgga   4500
atcattgctc gggccatagc agataagtat cactctagtg tgtactcact tccaccagac   4560
cctgaccatt ttgacgggta caaacagcaa gtggtcacag ttatggatga tctgtgtcag   4620
aatcccgacg gcaaggatat gtcgctattt tgccagatgg tgtccaccgt ggattttatc   4680
ccaccaatgg cttctcttga agaaaaggga gtttctttta catctaaatt tgttattgca   4740
tccaccaacg ccagcaacat tatagtgcct acagtgtctg actctgacgc catccgacgc   4800
aggttttaca tggattgcga cattgaggtg acggactcat ataaaacaga cttgggtaga   4860
ctagatgctg gacgggctgc taagttatgc tctgaaaaca acaccgcaaa cttcaaacga   4920
tgcagccctc tagtgtgtgg gaaggctatt caacttagag acaggaagtc caaggtcagg   4980
tacagcgtgg acacagtgat ctctgaacta attagagaat acaatagcag atccgctatt   5040
ggtaacacaa ttgaagcact attccaaggc ccgcctaagt tcaggccaat tagaatcagt   5100
cttgaggaga agccagcccc agacgctatt ggcgatcttc tcgctagtgt agacagcgag   5160
gaagtgcgcc aatactgtag ggagcaaggc tggatcatcc ctgaaactcc caccaatgtt   5220
gaacgacatc ttaacagagc agtgctagtt atgcaatcca tcgctactgt ggtggcagtt   5280
gtctcactgg tgtatgtcat ttacaagctc tttgcggggt ttcaaggcgc gtattctgga   5340
gctcccaagc aagtgctcaa gaaacccgtc ctccgcacgg caacagtgca gggtccaagt   5400
cttgactttg ctctatccct gctgagaagg aacatcaggc aagtccaaac agatcagggg   5460
cattttacca tgttaggtgt cagggatcgc ttagctgttc tcccacggca cgcacagccc   5520
```

-continued

```
gggaagacta tttgggtgga gcacaagctt gtgaacgtcc tcgacgcaat cgagctggtg   5580

gatgaacagg gcgttaattt ggaactcaca ttggtgacac tagacactaa tgaaaaattt   5640

agagatatca ccaagttcat tccagagacc attagcggcg ctagtgatgc aactttagtg   5700

atcaatacag aacatatgcc atcaatgttt gtcccagtgg gggacgtcgt gcagtatggg   5760

ttcttgaacc ttagtgggaa gccaacacat aggaccatga tgtacaattt ccctacaaaa   5820

gcaggacaat gtggaggtgt ggtcacatca gtcggtaaga ttgttggcat tcacattggc   5880

ggcaacgggc gccaagggtt ctgtgctggt ttgaagagga gttacttcgc aagtgtgcag   5940

ggtgagatcc aatgggtgaa gcctaacaaa gaaactggta gactgaacat caatggacca   6000

actcgcacta agctggagcc tagtgtgttt catgatgtgt ttgaaggcaa taaggaacca   6060

gcagtcttaa caagtaagga ccctagattg gaggtcgact ttgagcaagc cctgttttcc   6120

aagtatgtgg gcaatgtttt acatgagccc gatgaatacg tgactcaagc tgccctccac   6180

tatgcgaatc aactcaaaca gttggacata aacactagca agatgagcat ggaggaagcg   6240

tgctatggca ctgagaacct ggaagcaata gatctctgta ctagtgccgg atatccatac   6300

agcgcccttg gcatcaagaa aagagacatt ctcgaccccg taaccaggga tgtgtctaag   6360

atgaaattct atatggataa atacgggcta gatctgccat actccaccta cgtgaaggat   6420

gagcttagat ccctggataa aatcaagaaa ggaaaatcac gcctgataga ggctagtagc   6480

ttgaatgact ctgtctacct cagaatgacc tttgggcatc tttacgaggt atttcatgct   6540

aaccctggca ctgtgaccgg ttcggcagtg ggttgcaacc cagacgtgtt ttggagtaaa   6600

ctaccgatcc tactgcctgg gtcactcttt gcctttgact actcaggata tgatgctagc   6660

ctcagcccgg tatggttcag ggctctagaa gttgtgttac gggaaattgg gtatccagag   6720

gaggctgtgt ccctaataga aggaatcaac cacactcacc acgtgtaccg gaacaaaaca   6780

tattgtgtac ttggtgggat gccttcaggg tgttctggta cttccatctt taactcaatg   6840

atcaacaaca tcatcattag aaccctctta atcaaaacct ttaagggaat agacctggat   6900

gagttgaaca tggtggccta tggggacgat gtattggcta gttatccctt tcctatcgat   6960

tgccttgagc tggctaagac tggcaaagag tatggtttga ctatgacacc tgcagacaaa   7020

tcaccctgtt tcaatgaagt gacatgggaa aatgctacct tccttaagag agggttcttg   7080

ccagaccacc aatttccatt cttaattcac cctacgatgc ctatgagaga gatccatgag   7140

tccattcgat ggactaaaga cgcacgcaat acccaagatc acgtgcgctc tctgtgcctg   7200

ttggcatggc acaatggtaa ggatgaatat gaaaagtttg tgagtgcaat tagatcagtt   7260

ccagttggaa aagcgttggc cattcctaat tttgagaatt tgagaagaaa ttggctcgaa   7320

ttattttaac attacagctt aaagctgaac cccactagaa atctggtcgt gttaatgact   7380

agtgggggta aatttgttat aaccagaata gcaaaaaaaa aaaaaaaaaa aaaa         7434
```

<210> SEQ ID NO 14
<211> LENGTH: 66
<212> TYPE: DNA
<213> ORGANISM: Artificial Sequence
<220> FEATURE:
<223> OTHER INFORMATION: EV71 Y90-3896 5'-primer

<400> SEQUENCE: 14

```
ctttcgtctt caagaattgc ggccgcgtaa tacgactcac tataggttaa aacagcctgt     60

gggttg                                                                66
```

<210> SEQ ID NO 15
<211> LENGTH: 59
<212> TYPE: DNA
<213> ORGANISM: Artificial Sequence
<220> FEATURE:
<223> OTHER INFORMATION: EV71 Y90-3896 3'-primer

<400> SEQUENCE: 15
gagaattgtc gaatatgttt aaactttttt tttttttttt ttttttttg ctattctgg 59

<210> SEQ ID NO 16
<211> LENGTH: 52
<212> TYPE: DNA
<213> ORGANISM: Artificial Sequence
<220> FEATURE:
<223> OTHER INFORMATION: EV71 N772 5'-primer

<400> SEQUENCE: 16
ctaggcggcc gcgtaatacg actcactata ggttaaaaca gcctgtgggt tg 52

<210> SEQ ID NO 17
<211> LENGTH: 45
<212> TYPE: DNA
<213> ORGANISM: Artificial Sequence
<220> FEATURE:
<223> OTHER INFORMATION: EV71 N772 3'-primer

<400> SEQUENCE: 17
cacagtcgac tttttttttt tttttttttt tttttgctat tctgg 45

<210> SEQ ID NO 18
<211> LENGTH: 52
<212> TYPE: DNA
<213> ORGANISM: Artificial Sequence
<220> FEATURE:
<223> OTHER INFORMATION: EV71 C7-Osaka 5'-primer

<400> SEQUENCE: 18
ctaggcggcc gcgtaatacg actcactata ggttaaaaca gcctgtgggt tg 52

<210> SEQ ID NO 19
<211> LENGTH: 45
<212> TYPE: DNA
<213> ORGANISM: Artificial Sequence
<220> FEATURE:
<223> OTHER INFORMATION: EV71 C7/Osaka 3'-primer

<400> SEQUENCE: 19
cacactcgag tttttttttt tttttttttt tttttgctat tctgg 45

<210> SEQ ID NO 20
<211> LENGTH: 66
<212> TYPE: DNA
<213> ORGANISM: Artificial Sequence
<220> FEATURE:
<223> OTHER INFORMATION: EV71 2716-Yamagata 5'-primer

<400> SEQUENCE: 20
ctttcgtctt caagaattgc ggccgcgtaa tacgactcac tataggttaa aacagcctgt 60
gggttg 66

<210> SEQ ID NO 21
<211> LENGTH: 59
<212> TYPE: DNA
<213> ORGANISM: Artificial Sequence
<220> FEATURE:

-continued

<223> OTHER INFORMATION: EV71 2716-Yamagata 3'-primer

<400> SEQUENCE: 21
gagaattgtc gaatatgttt aaactttttt tttttttttt ttttttttg ctattctgg 59

STABLE PRODUCTION OF VIRULENT ENTEROVIRUS 71 AND USE THEREOF

RELATED APPLICATION

This application is a 35 § 371 national phase application of PCT Application PCT/JP2018/012410 filed Mar. 27, 2018, which claims priority to Japanese Application No. 2017-072562 filed Mar. 31, 2017. The entire contents of each are incorporated herein by reference in its entirety.

Statement Regarding Electronic Filing of a Sequence Listing

A Sequence Listing in ASCII text format, submitted under 37 C.F.R. § 1.821, entitled 5576-361ST25.txt, 52,868 bytes in size, generated on Sep. 12, 2019, and filed via EFS-Web, is provided in lieu of a paper copy. This Sequence Listing is hereby incorporated by reference into the specification for its disclosures.

FIELD OF THE INVENTION

The present invention relates to the stable production of a virulent hand, foot and mouth disease virus, and relates to screening for a vaccine or an antiviral drug using a virulent hand, foot and mouth disease virus.

BACKGROUND OF THE INVENTION

Hand, foot and mouth disease is a viral disease typically caused by viruses classified in human enterovirus group A (HEV-A) within the genus Enterovirus of the family Picornaviridae. Hand, foot and mouth disease manifests vesicular exanthema in the oral mucosa and distal portions of the extremities as a prominent symptom. Hand, foot and mouth disease may become epidemic in the summer, mostly in children, and the disease is generally mild and heals spontaneously in several days without special treatment. However, enterovirus 71 (EV71) has been reported to cause, in rare cases, severe complications of the central nervous system such as aseptic meningitis or encephalitis, in East Asia, a large number of deaths ascribable to major epidemics of EV71 have been reported since the late 1990s. This may be partly because enteroviruses, including EV71, which are RNA viruses, have a very high mutation rate resulting in virulent mutants during major epidemics of the viruses, as in other RNA viruses e.g., influenza viruses). Hence, the enteroviruses are considered to be dangerous viruses to public health. Thus, there is a demand for the development of vaccines or antiviral drugs thereagainst.

For the development of vaccines or antiviral drugs against enteroviruses, animal models susceptible to enterovieruses are necessary. The present inventors have already found that scavenger receptor class B member 2 (SCARB2), a cell surface receptor, is a molecule essential for EV71 infection, and prepared a transgenic mouse expressing human SCARB2 as an EV71-susceptible model mouse (Non Patent Document 1). Meanwhile, EV71 for infecting the model mouse is prepared by culturing using virus-susceptible cells such as RD cells. However, EV71 cultured using virus-susceptible cells has often been confirmed to exhibit marked reduction in its pathogenicity. This has been a major obstacle to the development of vaccines or antiviral drugs against EV71.

CITATION LIST

Non Patent Document

Non Patent Document 1: Fujii, K., et al., Proc. Nat. Acad. Sci. U.S.A., Vol. 110, No. 36, pp. 14753-14758 (2013)

SUMMARY OF INVENTION

Technical Problem

Cell membrane surface receptors binding to enteroviruses classified in HEV-A, including EV71, are known to include some molecules such as heparan sulfate and PSGL-1, in addition to SCARB2. However, functional difference among these cell membrane surface receptors, their correlation with the pathogenicity of the enteroviruses, selective pressure for mutated enteroviruses, or the like have not yet been elucidated.

The present invention has been made with an object to elucidate a mechanism underlying infection by enteroviruses classified in HEV-A, including EV71, and to provide stable production of virulent hand, foot and mouth disease viruses.

Solution to Problem

The present inventors have conducted diligent studies and consequently found that less virulent EV71, which infects via heparan sulfate, propagates more dominantly than virulent EV71, which infects via SCARB2, so that the attenuation of EV71 occurs. On the basis of this novel finding, the present inventors have established a host cells and a method for stably propagating virulent hand, foot and mouth disease viruses.

Specifically, according to one embodiment, the present invention provides a host cell for stably propagating virulent hand, foot and mouth disease virus, the host cell expressing no heparan sulfate and overexpressing primate scavenger receptor class B member 2 (SCARB2).

The virulent hand, foot and mouth disease virus is preferably a virus classified in human enterovirus group A.

The virulent hand, foot and mouth disease virus is preferably enterovirus 71, Coxsackie virus A16, Coxsackie virus A14 or Coxsackie virus A7.

The host cell preferably dose not express the EXT1 gene and/or EXT2 gene.

The SCARB2 is preferably human SCARB2.

The cell is preferably an RD cell.

According to one embodiment, the present invention also provides a method for stably producing a virulent hand, foot and mouth disease virus, comprising the steps of: (1) introducing genomic RNA of the virulent hand, foot and mouth disease virus into the host cell described above so as to obtain a cell producing the virulent hand, foot and mouth disease virus; (2) culturing the cell obtained by the step (1) so as to propagate the virulent hand, foot and mouth disease virus; and (3) harvesting the virulent hand, foot and mouth disease virus propagated by the step (2).

The virulent hand, foot and mouth disease virus is preferably a virus classified in human enterovirus group A.

The virulent hand, foot and mouth disease virus is preferably enterovirus 71, Coxsackie virus A16, Coxsackie virus A14 or Coxsackie virus A7.

According to one embodiment, the present invention also provides a virulent hand, foot and mouth disease virus strain prepared by the method described above.

According to one embodiment, the present invention also provides a method for screening for an anti-hand, foot and mouth disease virus vaccine, comprising the steps of: (1) providing a transgenic mouse expressing primate scavenger receptor class B member 2 (SCARB2); (2) inoculating a candidate vaccine into the transgenic mouse; (3) challenging the transgenic mouse of the step (2) with the virulent hand, foot and mouth disease virus strain described above; and (4) analyzing the transgenic mouse of the step (3).

According to one embodiment, the present invention also provides a method for screening for an anti-hand, foot and mouth disease virus drug, comprising the steps of: (1) providing a transgenic mouse expressing primate scavenger receptor class B member 2 (SCARB2); (2) infecting the transgenic mouse with the virulent hand, foot and mouth disease virus strain described above; (3) administering a candidate compound of the anti-hand, foot and mouth disease virus drug to the transgenic mouse of the step (2); and (4) analyzing the transgenic mouse of the step (3).

The SCARB2 is preferably human SCARB2.

The transgenic mouse is preferably at the age of 4 weeks or older.

Advantageous Effects of Invention

The host cell and the method for stably propagating a virulent hand, foot and mouth disease virus according to the present invention can culture a hand, foot and mouth disease virus without attenuating the causative virus and are therefore capable of stably and efficiently providing the virulent hand, foot and mouth disease virus strains.

The virulent hand, foot and mouth disease virus strains and the method for screening for an anti-hand, foot and mouth disease virus vaccine or an anti-hand, foot and mouth disease virus drug using the same according to the present invention stably have high reproducibility. Hence, the virulent virus strains and the method according to the present invention are useful for the development and quality control of vaccines and antiviral drugs.

DESCRIPTION OF EMBODIMENTS

Figure 1:
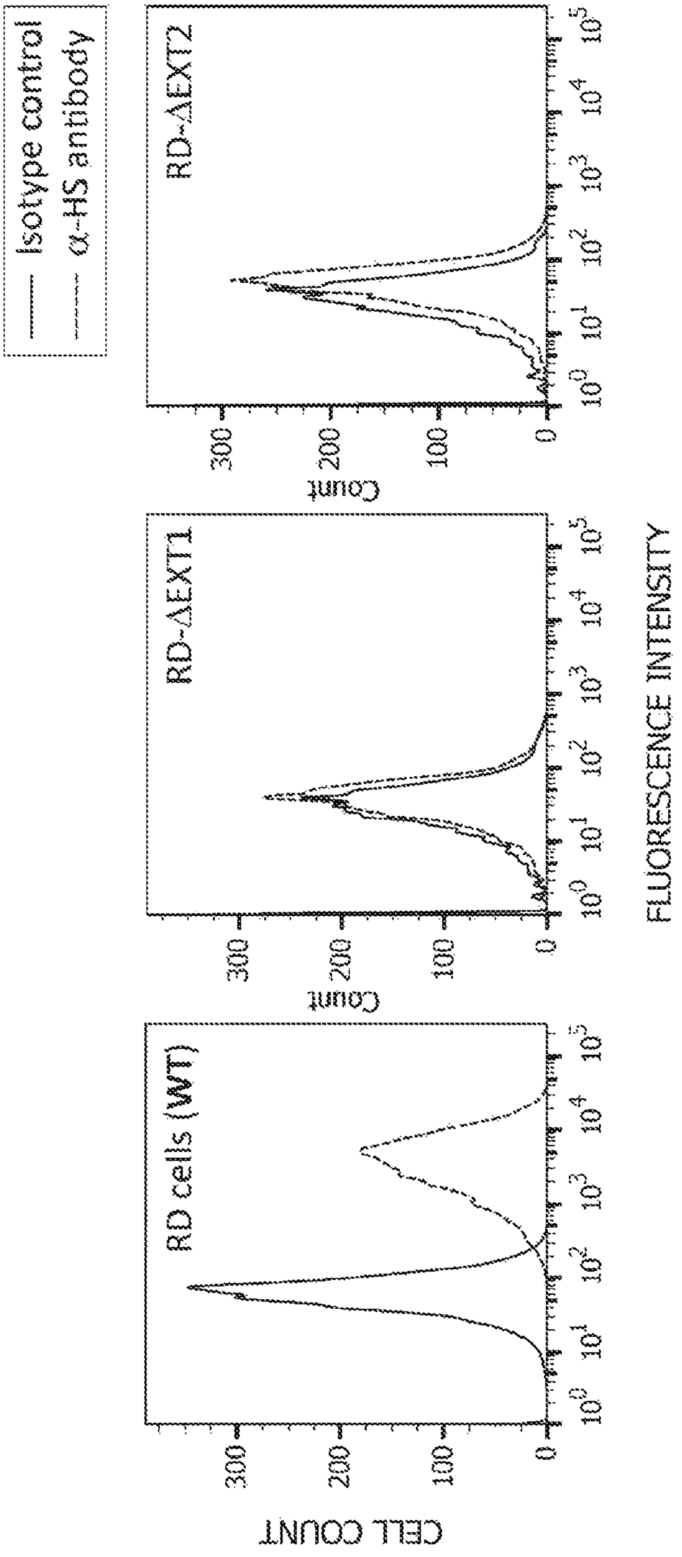
FIG. 1 is a diagram showing results of confirming a heparan sulfate expression level in EXT1 gene- or EXT2 gene-knockout RD cells.

Hereinafter, the present invention will be described in detail. However, the present invention is not limited by the embodiments described in the present specification.

According to the first embodiment, the present invention provides a host cell for stably propagating virulent hand, foot and mouth disease virus, the host cell expressing no heparan sulfate and overexpressing primate scavenger receptor class B member 2 (SCARB2).

The “hand, foot and mouth disease virus” means an enterovirus that infects humans and causes hand, foot and mouth disease. Also, the “virulent hand, foot and mouth disease virus” according to the present embodiment refers to a hand, foot and mouth disease virus that has neuropathogenicity and causes lethal infection.

Enteroviruses are viruses classified in the genus Enterovirus of the family Picornaviridae. These viruses have no envelope and contain positive-sense, single-stranded RNA in a dodecahedral capsid constituted by 4 types of proteins, VP1 to VP4. The genus Enterovirus includes polioviruses, Coxsackie group A viruses (CAV), Coxsackie group B viruses (CBV), echoviruses, and enteroviruses. Among them, the enteroviruses that infect humans are classified into 4 species: human enterovirus species A (HEV-A), human enterovirus species B (HEV-B), human enterovirus species C (HEV-C), and human enterovirus species D (HEV-D), on the basis of molecular phylogenetic analysis, and further classified into many serotypes depending on difference in neutralizing reactivity brought about by antibodies.

An enterovirus of any serotype can be used as the hand, foot and mouth disease virus according to the present embodiment as long as the enterovirus is virulent. A gene mutation determinative of the severity of the virulence of the hand, foot and mouth disease virus has not yet been fully identified; however, the present invention is partly based on the finding that the 145th amino acid of the VP1 capsid protein is glutamic acid (E) (VP1-145E) in most cases in EV71 isolated from EV71-infected patients, whereas this amino acid is glycine (G) (VP1-145G) or glutamine (Q) (VP1-145Q) in EV71 passaged in cultured cells, and these EV71 viruses are less virulent. Although not wishing to be bound by any particular theory, the mutation in the 145th amino acid of the VP1 capsid protein may change the surface charge distribution of the virus particle, resulting in changes in the binding affinity of EV71 for heparan sulfate, which presumably brings about change in the virulence of EV71. Thus, any hand, foot and mouth disease virus that exhibits no binding affinity for heparan sulfate, as in VP1-145E, and causes infection mediated by SCARB2, is likely to be virulent, as in VP1-145E. In this context, the “infection” means a series of processes in which a virus particle binds to the surface of a host cell, is thereby taken up into the host cell, and uncoated so that a progeny virus grows.

Specifically, the virulent hand, foot and mouth disease virus according to the present embodiment is preferably a virus classified into HEV-A, particularly preferably enterovirus 71 (EV71), Coxsackie virus A16 (CVA16), Coxsackie virus A14 (CVA14) or Coxsackie virus A7 (CVA7), most preferably EV71.

The enterovirus 71 (EV71) is further classified into subgenogroups A, B1 to B5, and C1 to C5 on the basis of the molecular phylogenetic analysis of the VP1 gene. The EV71 according to the present embodiment can be EV71 of any subgenogroup. Examples thereof include, but are not limited to, Y90-3896 strains subgenogroup C1), Isehara strains (subgenogroup C2), N772-Sendai. H-06 strains (subgenogroup C4), and 2716-Yamagata-03 strains (subgenogroup B5). All of these strains isolated from EV71-infected patients are VP1-145E. Nucleotide sequence information on EV71 of each subgenogroup can be obtained from a predetermined database.

The virulent hand, foot and mouth disease viruses according to the present embodiment can be defined by 50% lethal dose ($LD_{50}$) in an enterovirus-susceptible model mouse expressing human SCARB2 (Proc. Nat. Acad. Sci. Vol. 110, No. 36, pp. 14753-14758). The $LD_{50}$ of the virulent hand, foot and mouth disease virus according to the present embodiment is preferably $10^6$ $TCID_{50}$ or lower, particularly preferably $10^5$ $TCID_{50}$ or lower.

The "host cell" according to the present embodiment refers to target cells that can be infected with a hand, foot and mouth disease viruses. The "infection" is as defined above. The host cell according to the present embodiment can be prepared using any mammalian cells generally used for the culturing of viruses. Examples of the cells that can be used for preparing the host cell according to the present embodiment include, but are not limited to, RD cells, Vero cells, HeLa cells, MDCK cells, COS-7 cells, HEK293T cells, and BHK cells. The cell that can be used for preparing the host cells according to the present embodiment is preferably an RD cell.

The host cell according to the present embodiment expresses no heparan sulfate. The "heparan sulfate" is a sugar chain having glucosamine and uronic acid as constituents and is widespread, in the form of proteoglycan bound with a core protein, on cell surface or in extracellular matrix. The phrase "expressing no heparan sulfate" means that the amount of the heparan sulfate produced is lost or decreased to an extent that the heparan sulfate cannot be detected by a detection approach (e.g., immunochemical approach) usually performed.

The host cell according to the present embodiment expresses no heparan sulfate because an enzyme involved in the biosynthesis of heparan sulfate is inactivated due to a mutation, or a gene encoding the enzyme is not expressed. Preferably, the host cell according to the present embodiment expresses no heparan sulfate because the gene encoding the enzyme involved in the biosynthesis of heparan sulfate is not expressed. It is known that the EXT gene family is involved in the biosynthesis of heparan sulfate. This family includes EXT1, EXT2, EXTL1, EXTL2 and EXTL3 genes. The EXT1 and EXT2 genes each encode an enzyme having both the activities of α1,4-GlcNAc transferase and β1,4-GlcA transferase, while the EXTL1, EXTL2 and EXTL3 genes also each encode GlcNAc transferase. Thus, preferably, the host cell according to the present embodiment does not express the EXT1, EXT2, EXT1, EXTL2 and/or EXTL3 genes. Particularly preferably, the host cell according to the present embodiment does not express any one or both of the EXT1 and EXT2 genes.

The expression of the gene involved in the biosynthesis of heparan sulfate can be deleted by a method well known in the art. For example, the gene itself may be destroyed (knockout) by a genome editing technique using CRISPR/Cas9 or the like, or the expression of the gene may be suppressed (knockdown) by gene silencing using siRNA or the like. Also, the genes involved in the biosynthesis of heparan sulfate have already been cloned, and the nucleotide sequence information of the genes can be obtained from a predetermined database. For example, GenBank Accession No. NM_000127 for human EXT1 gene, and GenBank Accession Nos. NM_000401, NM_207122, and NM_1178083 for human EXT2 gene are available.

The host cell according to the present embodiment further overexpresses primate scavenger receptor class B member 2 (SCARB2). The "scavenger receptor class B member 2 (SCARB2)" (hereinafter, simply referred to as "SCARB2") is a cell surface receptor protein having two transmembrane regions and is a molecule essential for infection by some viruses classified into HEV-A. The "overexpression" of SCARB2 refers to the state in which SCARB2 is expressed beyond the original expression level of a host cell harboring no exogenous SCARB2-encoding gene.

In the present embodiment, SCARB2 can be overexpressed by introducing an exogenous SCARB2-encoding gene into the host cells. The SCARB2-encoding gene that can be used in the present embodiment may be derived from any primate and is preferably human-derived. The SCARB2-encoding gene has already been cloned, and the nucleotide sequence information of the gene can be obtained from a predetermined database. For example, GenBank Accession No. BC021892.1 for human SCARB2 gene is available.

The transfer of the exogenous SCARB2-encoding gene to the host cells can be performed by a method well known in the art. The exogenous SCARB2-encoding gene can be introduced into the host cells, for example, by transfecting the host cells with an expression vector having an insert of the exogenous SCARB2-encoding gene. For example, a plasmid such as pcDNA3.1 (Invitrogen) or a retrovirus vector can be used as the expression vector. The transfection can be performed by a well-known method such as a calcium phosphate coprecipitation method, an electroporation method, a microinjection method, or a lipofection method.

The host cell of the present embodiment is useful for stably propagating virulent hand, foot and mouth disease viruses. In this context, the term "stably" means that virulence possessed by a seed virus for propagation is maintained in a virus strain obtained by propagation. The hand, foot and mouth disease virus has a very high mutation frequency for culturing, as in other RNA viruses. Hence, in the case of using host cells generally used in the art with the hand, foot and mouth disease virus, a less virulent hand, foot and mouth disease virus appears due to a mutation as the number of culture days or the cell passage number increased, and a repetition of the preferential infection of host cells with this less virulent virus attenuates the hand, foot and mouth disease virus strain. In contrast, selective infection with the less virulent hand, foot and mouth disease virus resulting from a mutation is minimized in the host cell according to the present embodiment, which can therefore produce the virulent hand, foot and mouth disease virus strain that maintains virulence similar to that before culturing.

According to the second embodiment, the present invention provides a method for stably producing a virulent hand, foot and mouth disease virus, comprising the steps of: (1) introducing genomic RNA of the virulent hand, foot and mouth disease virus into the host cell described above so as to obtain a cell producing the virulent hand, foot and mouth disease virus; (2) culturing the cell obtained by the step (1) so as to propagate the virulent hand, foot and mouth disease virus; and (3) harvesting the virulent hand, foot and mouth disease virus propagated by the step (2).

The terms "host cell", "virulent hand, foot and mouth disease virus" and "stably" according to the present embodiment are as defined in the first embodiment.

In the method of the present embodiment, genomic RNA of the virulent hand, foot and mouth disease virus is introduced into the host cells according to the first embodiment to prepare a cell producing the virulent hand, foot and mouth disease virus (hereinafter, simply referred to as a "virus-producing cell"). The introduction of the genomic RNA of the virulent hand, foot and mouth disease virus to the host cells may be performed by infection with the virulent hand, foot and mouth disease virus or may be performed by transfection with the prepared genomic RNA of the virulent hand, foot and mouth disease virus.

The infection of the host cells with the virulent hand, foot and mouth disease virus can be performed according to heretofore known conditions. For example, the host cells can be seeded at a density of $10^4$ to $10^5$ cells/$cm^2$ and then infected by the addition of the virulent hand, foot and mouth disease virus at MOI=0.01 to 10. The virulent hand, foot and mouth disease virus for infecting the host cells can be isolated from throat swabs, rectum swabs, feces, or the like of an animal infected with a hand, foot and mouth disease virus or a hand, foot and mouth disease patient which has developed a central nervous system disease, or can be obtained from National Institute of Infectious Diseases of Japan or a local institute of health in Japan.

The genomic RNA of the virulent hand, foot and mouth disease virus can be prepared by cloning cDNA of the virulent hand, foot and mouth disease virus and by in vitro transcription of the cDNA. The transfection of the host cells with the genomic RNA of the virulent hand, foot and mouth disease virus can be performed by a well-known method such as a lipofection method, an electroporation method, or a microinjection method. The cDNA of the virulent hand, foot and mouth disease virus can be prepared by a known method from the virulent hand, foot and mouth disease virus isolated or obtained in the same way as above.

Subsequently, the virus-producing cells thus obtained are cultured to culture the virulent hand, foot and mouth disease virus. The culture conditions for the virus-producing cell can be known conditions. For example, the virus-producing cells can be cultured for approximately 3 to 7 days until a cytopathic effect (CPE) is observed. CPE is a morphological change in virus-producing cells that occurs by the intracellular accumulation of cultured viruses, and can be easily confirmed by observation under an optical microscope.

Subsequently, the propagated virulent hand, foot and mouth disease virus is harvested. The propagated virulent hand, foot and mouth disease virus is released into the culture medium or is accumulated inside the producing cells, and can be harvested by a heretofore known method. The propagated virulent hand, foot and mouth disease virus can be harvested, for example, by repeated sonication or freeze-thaw cycling of the culture solution containing the virus-producing cells so as to destroy the virus-producing cells, followed by the removal of cell debris by centrifugation. If necessary, the harvested virulent hand, foot and mouth disease virus may be further purified by polyethylene glycol precipitation, density gradient ultracentrifugation, or the like.

The method of the present embodiment employs the host cells that can stably culture virulent hand, foot and mouth disease viruses. Thus, the method of the present embodiment can minimize the propagation of less virulent hand, foot and mouth disease viruses and easily and stably produce the virulent hand, foot and mouth disease viruses. Hence, the method of the present embodiment is capable of easily preparing virulent hand, foot and mouth disease virus strains.

According to the third embodiment, the present invention provides a virulent hand, foot and mouth disease virus strain prepared by the method described above.

In the present embodiment, the "virulent hand, foot and mouth disease virus strain" is a population of multiple causative virus particles of hand, foot and mouth disease and refers to the population that exhibits high virulence as a whole. The term "virulent" according to the present embodiment is as defined in the first embodiment. The virulent hand, foot and mouth disease virus strain according to the present embodiment may be substantially constituted by a virulent hand, foot and mouth disease virus of a single serotype or subgenogroup or may be substantially constituted by virulent causative viruses of hand, foot and mouth disease of a plurality of serotypes or subgenogroups. In this context, the phrase "substantially constituted" means that a hand, foot and mouth disease virus attenuated due to a mutation contaminates the prepared hand, foot and mouth disease virus strain to an extent that does not influence the neuropathogenicity of the virus strain. Preferably, the virulent hand, foot and mouth disease virus strain according to the present embodiment is substantially constituted by a VP1-145E mutant of EV71, or a mutant of EV71, CVA16, CVA14 or CVA7 that has binding affinity for SCARB2 similar thereto and causes infection mediated by SCARB2.

The virulent hand, foot and mouth disease virus strains according to the present embodiment have neuropathogenicity and can cause lethal infection. Hence, the virulent hand, foot and mouth disease virus strains according to the present embodiment are useful for the development of vaccines or antiviral drugs against virulent virus strains of hand, foot and mouth disease.

According to the fourth embodiment, the present invention provides a method for screening for an anti-hand, foot and mouth disease virus vaccine, comprising the steps of: (1) providing a transgenic mouse expressing primate scavenger receptor class B member 2 (SCARB2); (2) inoculating a candidate vaccine into the transgenic mouse; (3) challenging the transgenic mouse of the step (2) with the virulent hand, foot and mouth disease virus strain described above; and (4) analyzing the transgenic mouse of the step (3).

The terms "SCARB2" and "virulent hand, foot and mouth disease virus" according to the present embodiment are as defined in the first embodiment. The term "virulent hand, foot and mouth disease virus strain" is as defined in the third embodiment.

The method of the present embodiment employs a transgenic mouse expressing primate SCARB2. The transgenic mouse according to the present embodiment can be produced by a method well known in the art. The transgenic mouse expressing primate SCARB2 can be produced, for example, by introducing an expression vector comprising a gene encoding primate SCARB2 located downstream of an appropriate promoter sequence into mouse fertilized eggs by microinjection or the like. The transgenic mouse according to the present embodiment is preferably produced by the introduction of an artificial chromosome, such as BAC, comprising a cloned full-length primate SCARB2 gene locus including transcriptional regulatory regions. The SCARB2-encoding gene that can be used in the present embodiment can be derived from any primate and is preferably human-derived. Nucleotide sequence information on the gene encoding primate SCARB2 can be obtained from a predetermined database, as described in the first embodiment.

Alternatively, an already established strain may be used as the transgenic mouse expressing primate SCARB2. For example, hSCARB2-Tg10 (Proc. Nat. Acad. Sci. U.S.A., Vol. 110, No. 36, pp. 14753-14758), a transgenic mouse expressing human SCARB2, can be used.

The transgenic mouse used in the present embodiment is preferably an adult mouse having a mature immune response. Since the immune response of mouse pups younger than 4 weeks is at an immature state of development, the effect of a vaccine cannot be sufficiently evaluated in some cases. Thus, the transgenic mouse used in the present embodiment is preferably at 4 weeks or older, particularly preferably at the age of 4 to 12 weeks.

Subsequently, a candidate vaccine is inoculated into the transgenic mouse. The candidate vaccine includes a vaccine in a development phase as well as a commercialized vaccine to be assayed for quality control before shipment. Examples of the candidate vaccine include inactivated vaccines, empty virus-like particle vaccines, live (attenuated) vaccines, peptide vaccines, and DNA vaccines. The amount of the candidate vaccine inoculated differs depending on the type of the candidate vaccine and can be appropriately selected, for example, in the range of 0.01 to 10 μg/kg of body weight.

In the present embodiment, the candidate vaccine may be mixed with an adjuvant for administration. The adjuvant is a substance that nonspecifically potentiates the immune response of a host animal, and various adjuvants are known in the art. Examples of the adjuvant that can be used in the present embodiment include, but are not limited to, aluminum hydroxide, calcium phosphate, aluminum phosphate, alum, popes, and carboxyvinyl polymers.

In the present embodiment, the inoculation of the candidate vaccine can be performed once or repetitively a plurality of times. Preferably, the inoculation is performed repetitively a plurality of times. In the case of inoculating the candidate vaccine repetitively a plurality of times, it is preferred to repeat inoculation at intervals of 2 to 4 weeks. Examples of the administration route of the candidate vaccine include, but are not particularly limited to, intraperitoneal administration, intravenous administration, and subcutaneous administration.

Subsequently, the transgenic mouse inoculated with the candidate vaccine is challenged with the virulent hand, foot and mouth disease virus strain. The challenge can be performed by administering the virulent hand, foot and mouth disease virus strains in an amount that kills 90% or more transgenic mice that have not received the candidate vaccine. Specifically, the dose of the virulent hand, foot and mouth disease virus strain according to the present embodiment for challenge is preferably an amount of 10 to 100 times $LD_{50}$ for the transgenic mice that have not received the candidate vaccine. Examples of the administration route of the virulent hand, foot and mouth disease virus strain according to the present embodiment include, but are not particularly limited to, intraperitoneal administration, intravenous administration, and subcutaneous administration.

The challenge with the virulent hand, foot and mouth disease virus strain according to the present embodiment is preferably performed 1 to 20 weeks after the inoculation of the candidate vaccine. In order to determine the timing of the challenge, sera may be collected from the transgenic mice inoculated with the candidate vaccine, and antibody titer of the sera can be confirmed in advance.

Subsequently, the challenged transgenic mouse is analyzed to evaluate the efficacy of the candidate vaccine. The analysis of the transgenic mice can be performed by observing, for example, a live or dead status or the presence or absence of paralytic symptoms, by a method well known in the art.

In the screening method of the present embodiment, the candidate vaccine can be evaluated as being promising as an anti-hand, foot and mouth disease virus vaccine when the administration of this candidate vaccine significantly decreases death rate and paralytic symptoms as compared with transgenic mice that have not received the candidate vaccine. On the other hand, the candidate vaccine can be evaluated as being not promising or effective as an anti-hand, foot and mouth disease virus vaccine when the administration of this candidate vaccine does not change or increases death rate and paralytic symptoms as compared with transgenic mice that have not received the candidate vaccine.

According to the fifth embodiment, the present invention provides a method for screening for an anti-hand, foot and mouth disease virus drug, comprising the steps of: (1) providing a transgenic mouse expressing primate scavenger receptor class B member 2 (SCARB2); (2) infecting the transgenic mouse with the virulent hand, foot and mouth disease virus strain described above; (3) administering a candidate compound of the anti-hand, foot and mouth disease virus drug to the transgenic mouse of the step (2); and (4) analyzing the transgenic mouse of the step (3).

The terms "SCARB2", "virulent hand, foot and mouth disease virus" and "infection" according to the present embodiment are as defined in the first embodiment. The term "virulent hand, foot and mouth disease virus strain" is as defined in the third embodiment.

The method of the present embodiment employs a transgenic mouse expressing primate SCARB2. The transgenic mouse according to the present embodiment is the same as in the fourth embodiment. The transgenic mouse used in the present embodiment is preferably at 4 weeks or older, particularly preferably at the age of 4 to 12 weeks.

Subsequently, the transgenic mouse is infected by the administration of the virulent hand, foot and mouth disease virus strain. The dose of the virulent hand, foot and mouth disease virus strain is preferably an amount of 10 to 100 times $LD_{50}$ for the transgenic mice. Examples of the administration route of the virulent hand, foot and mouth disease virus strain according to the present embodiment include, but are not particularly limited to, intraperitoneal administration, intravenous administration, and subcutaneous administration.

Subsequently, a candidate compound of the anti-hand, foot and mouth disease virus drug is administered to the transgenic mouse infected with the virulent hand, foot and mouth disease virus. Examples of the candidate compound include synthetic compounds, peptidic compounds, nucleic acids, and antibodies. These candidate compounds may be novel or may be known. The concentration of the candidate compound to be administered differs depending on the type of the compound and can be appropriately selected, for example, in the range of 1 nM to 10 μM. The administration of the candidate compound can be performed over, for example, 1 day to 2 weeks. Examples of the administration route of the candidate compound include, but are not particularly limited to, oral administration, intraperitoneal administration, intravenous administration, and subcutaneous administration.

Subsequently, the transgenic mouse given the candidate compound is analyzed to evaluate the efficacy of the candidate compound as an anti-hand, foot and mouth disease virus drug. The analysis of the transgenic mice can be performed by a method well known in the art, as in the fourth embodiment.

In the screening method of the present embodiment, the candidate compound can be evaluated as being promising as an anti-hand, foot and mouth disease virus drug when the administration of this candidate compound significantly decreases death rate and paralytic symptoms as compared with transgenic mice that have not received the candidate compound. On the other hand, the candidate compound can be evaluated as being not promising as an anti-hand, foot and mouth disease virus drug when the administration of this candidate compound does not change or increases death rate and paralytic symptoms as compared with transgenic mice that have not received the candidate compound.

EXAMPLES

Hereinafter, the present invention will be further described with reference to Examples. However, these examples do not limit the present invention by any means.

1. Preparation of Heparan Sulfate (HS)-Deficient Cells

RD cells expressing no heparan sulfate (HS) were prepared by genome editing using a CRISPR/Cas9 system. The sequence of guide RNA (sgRNA) targeting each of the EXT1 gene (GenBank Accession No. NM_000127) and the EXT2 gene (GenBank Accession Nos. NM_000401, NM_207122, and NM_1178083) was designed. The following DNA fragment encoding the sgRNA was inserted to the BbsI cleavage site of pSpCas9(13B)-2A-GFP plasmid (Addgene)

(i) DNA Sequence for EXT1-sgRNA

```
[Formula 1]
                                      (SEQ ID NO: 1)
Sense:          caccacccacaacacatc

                                      (SEQ ID NO: 2)
Antisense:      aaaccatttcctccttc
```

(ii) DNA Sequence for EXT2-sgRNA

```
[Formula 2]
                                      (SEQ ID NO: 3)
Sense:          cacccttcaattcaccaatcca

                                      (SEQ ID NO: 4)
Antisense:      aaacctatttacattaac
```

RD cells were transfected with the obtained plasmid and cultured for 3 days. Then, the cells were applied to FACSAria (Becton, Dickinson and Company) to separate GFP-positive cells. Cloning was carried out as to the separated cells by the limiting dilution method to obtain a single clone.

The obtained single clone was analyzed for the expression level of HS on the cell surface by the following procedures: the cells were collected by detachment with trypsin and suspended in PBS containing 2% fetal bovine serum. Then, $2\times10^5$ cells were separated and reacted on ice with mouse anti-HS monoclonal antibody F58-10E4 (AMS Biotechnology (Europe) Ltd.) (1:50 dilution) or isotype control antibody mouse IgM MM-30 (BioLegend, Inc.) (1:50 dilution), as a primary antibody, and Cy3-labeled anti-mouse IgM antibody (Jackson ImmunoResearch Laboratories, Inc.) (1:200 dilution as a secondary antibody, for 30 minutes each. Then, unreacted antibodies were removed from the reaction solution by centrifugation to prepare a sample for analysis. The sample for analysis was applied to BD LSRFortessa X-20 (Becton, Dickinson and Company) to analyze the amount of Cy3 bound to the cell surface. Also, a sample prepared by the same procedures as above, except that wild-type RD cells were used instead of the obtained single clone, was used as a negative control.

The results are shown in FIG. 1. In the wild-type RD cells, the fluorescence intensity peak of the sample reacted with the anti-HS antibody was remarkably shifted as compared with the fluorescence intensity peak of the control sample reacted with the isotype control antibody, confirming that HS was expressed in a large amount (FIG. 1, left). On the other hand, in the EXT1 gene-knockout RD cell clone (RD-ΔEXT1) and the EXT2 gene-knocked RD cell clone (RD-ΔEXT2), the fluorescence intensity peak of the sample reacted with the anti-HS antibody almost overlapped with the fluorescence intensity peak of the control sample reacted with the isotype control antibody, confirming that no HS was substantially expressed (FIG. 1, center and right).

2. Preparation of HS-Deficient/SCARB2-Overexpressing Cell

The human SCARB2 gene (GenBank Accession Nos. NM_001204255 and NM_005506) was introduced into each of RD-ΔEXT1 and RD-ΔEXT2 obtained in the above Item 1, by the following procedures to prepare HS-deficient RD cells overexpressing human SCARB2 (RD-ΔEXT1-SCARB2 and RD-ΔEXT2-SCARB2). GP2-293 packaging cells were transfected with a retrovirus vector having an insert of the human SCARB2 gene (pQCXIP-hSCARB2) and pVSV-G. Two days later, the supernatant was collected to obtain a retrovirus for human SCARB2 expression. RD-ΔEXT1 and RD-ΔEXT2 were each infected with the obtained retrovirus and then selectively cultured in the presence of 1 μg/ml puromycin to obtain RD-ΔEXT1-SCARB2 and RD-ΔEXT2-SCARB2. Also, cells (RD-SCARB2) were prepared by allowing wild-type RD cells to overexpress the SCARB2 gene by the same procedures as above.

3. Culturing of EV71 using HS-Deficient/SCARB2-Overexpressing Cells

First, EV71 with a passage number of P0 was prepared by the following protocol: genomic RNA was extracted from an EV71 Isehara strain (obtained from National Institute of Infectious Diseases of Japan), and cDNA was prepared therefrom using SuperScript® III reverse transcriptase (Thermo Fisher Scientific, Inc.). The cDNA (SEQ ID NO: 7) against the full-length genomic RNA was amplified by PCR using the following primer set.

5' primer (NotI cleavage sequence+T7 promoter sequence+5'-terminal 20 bases of the virus genome)

```
[Formula 3]
                                                  (SEQ ID NO: 5)
cggcggccgcgtaatacgactcactataggttaaaacagcctgggttg
```

3' primer (SalI cleavage sequence+poly(A) sequence (25 bases)+3'-terminal 10 bases of the virus genome)

```
[Formula 4]
                                                  (SEQ ID NO: 6)
tactcacttttttttttttttttttttttttctattct
```

TABLE 1

| EV71 Isehara strain full-length cDNA sequence (SEQ ID NO: 7) |
|---|
| [Table 1A] |
| TTAAAACAGCCTGTGGGTTGCACCCACCCACAGGGCCCACTGGGCGCCAGCACTCTGGTA |
| CTGAGGTACCTTTGTGCGCCTGTTTTTACTTCCCCTCCCCGAAGTAACTTAGAAGCTGTA |

TABLE 1-continued

| EV71 Isehara strain full-length cDNA sequence (SEQ ID NO: 7) |
|---|
| AATCAACGATCAATAGTAGGTGTGACACACCAGTCACACTTTGGTCAAGCACTTCTGTTT |
| CCCCGGACTGAGTATCAATAGGCTGCTCGCGCGGCTGAAGGAGAAAACGTTCGTTACCCG |
| ACCAACTACTTCGAGAAGCTTAGTACCACCATGAACGAGGCAGAGTGTTTCGTTCAGCAC |
| AACCCCAGTGTAGATCAGGCTGATGAGTCACTGCAACCCCCATGGGCGACCATGGCAGTG |
| GCTGCGTTGGCGGCCTGCCCATGGAGAAATCCATGGGACGCTCTAATTCTGACATGGTGC |
| GAAGAGCCTATTGAGCTAGTTGGTAGTCCTCCGGCCCCTGAATGCGGCTAATCCTAACTG |
| CGGAGCACATGCTCACAAACCAGTGGGTGGTGTGTCGTAACGGGCAACTCTGCAGCGGAA |
| CCGACTACTTTGGGTGTCCGTGTTTCCTTTTATTCTTATATTGGCTGCTTATGGTGACAA |
| TCAAAGAATTGTTACCATATAGCTATTGGATTGGCCATCCAGTGTGCAACAGAGCAATTG |
| TTTATCTATTCATTGGTTTCGTACCTTTATCACTGAAGTCTGTGATCACTCTTAAATTCA |
| TTTTGACCCTCAATACAATTAAACATGGGCTCACAGGTGTCCACACAGCGCTCCGGTTCG |
| CATGAAAATTCTAACTCAGCCACCGAGGGTTCCACCATAAATTATACTACCATTAATTAC |
| TATAAAGACTCCTATGCCGCCACAGCAGGTAAACAGAGCCTTAAGCAGGACCCAGACAAG |
| TTTGCAAATCCTGTCAAAGACATCTTCACTGAAATGGCAGCGCCATTAAAATCTCCATCT |
| GCTGAGGCATGTGGTTACAGCGATCGGGTAGCACAGTTAACTATTGGCAACTCTACCATC |
| ACTACGCAAGAAGCAGCAAACATGATAGTTGGCTATGGTGAGTGGCCATCCTACTGCTCG |
| GATTCTGACGCCACAGCAGTGGACAAACCAACGCGCCCAGATGTTTCAGTGAATAGGTTT |
| TATACATTGGACACTAAATTGTGGGAGAAATCATCCAAGGGGTGGTACTGGAAATTCCCG |
| GATGTGTTGACTGAAACCGGGGTCTTCGGTCAAAATGCACAATTCCACTACCTCTATCGG |
| TCGGGATTCTGCATTCACGTGCAGTGCAATGCTAGTAAGTTCCACCAAGGAGCACTCCTA |
| GTCGCTGTCCTCCCAGAATATGTCATTGGGACAGTAGCAGGTGGCACAGGGACGGAGGAT |
| AGTCACCCCCCTTACAAGCAGACTCAACCCGGTGCTGATGGCTTTGAATTGCAACACCCG |
| TACGTGCTTGATGCTGGCATTCCAATATCACAATTAACAGTGTGCCCACACCAGTGGATT |
| AATTTGAGGACTAACAATTGTGCCACAATAATAGTACCGTACATAAACGCACTACCCTTT |
| GATTCTGCCTTGAACCATTGCAACTTTGGTCTGCTGGTTGTGCCTATTAGCCCGTTAGAT |
| TATGACCAAGGTGCGACGCCAGTGATCCCCATTACTATCACATTGGCCCCAATGTGCTCT |
| GAATTTGCAGGCCTTAGGCAAGCAGTTACGCAAGGGTTTCCTACTGAGCTGAAACCCGGC |
| ACAAACCAATTTTTAACCACTGACGATGGCGTCTCAGCACCCATTCTGCCAAACTTTCAC |
| CCCACCCCGTGTATCCATATACCCGGTGAAGTTAGAAACTTGCTAGAGCTATGCCAGGTG |
| GAGACCATCTTAGAGGTTAACAATGTACCCACGAATGCCACTAGCTTAATGGAGAGGCTG |
| CGCTTCCCGGTCTCAGCCCAAGCCGGGAAAGGTGAACTATGTGCAGTGTTCAGAGCTGAC |
| CCTGGGCGAAATGGACCATGGCAGTCCACCCTGTTGGGTCAGTTGTGTGGGTATTACACC |
| CAATGGTCAGGATCACTGGAAGTCACCTTCATGTTTACTGGGTCCTTTATGGCTACTGGC |
| AAGATGCTCATAGCATACACACCACCAGGAGGCCCCTTACCCAAGGACCGGGCGACCGCC |
| ATGTTGGGTACACACGTCATCTGGGACTTTGGGTTGCAATCGTCTGTCACCCTTGTAATA |
| CCATGGATCAGCAACACTCACTACAGAGCGCACGCTCGAGATGGTGTGTTCGATTACTAC |
| ACTACAGGTTTGGTTAGCATATGGTACCAGACGAATTACGTGGTTCCAATTGGGGCACCT |
| AATACAGCCTACATAATAGCATTGGCGGCAGCCCAGAAGAATTTCACCATGAAGTTGTGT |
| AAGGATGCTAGTGATATCCTACAGACAGGCACTATCCAGGGAGACAGGGTGGCAGATGTG |

TABLE 1-continued

| EV71 Isehara strain full-length cDNA sequence (SEQ ID NO: 7) |
|---|
| ATTGAGAGTTCTATAGGGGATAGTGTGAGCAGAGCCCTCACCCAAGCTTTACCGGCACCT |
| ACAGGCCAAAACACGCAGGTAAGCAGCCACCGATTAGACACTGGTAAAGTTCCAGCACTC |
| CAAGCCGCTGAAATTGGAGCATCATCAAATGCCAGCGATGAGAGTATGATTGAGACACGA |
| TGTGTTCTTAATTCACACAGCACAGCTGAGACCACTCTTGATAGCTTCTTCAGTAGAGCG |

| [Table 1B] |
|---|
| GGATTAGTTGGAGAGATAGACCTCCCTCTTGAAGGCACAACCAACCCGAATGGGTATGCA |
| AATTGGGACATAGACATAACAGGTTACGCGCAAATGCGTAGAAAGGTGGAGCTGTTTACC |
| TACATGCGTTTTGACGCAGAGTTCACCTTCGTAGCGTGCACGCCTACCGGGGAAGTTGTC |
| CCGCAATTGCTCCAATATATGTTTGTACCACCTGGAGCCCCCAAGCCAGACTCTAGAGAA |
| TCTCTTGCATGGCAAACTGCCACTAATCCCTCAGTCTTTGTGAAGCTGTCAGACCCCCCA |
| GCACAGGTTTCAGTTCCATTCATGTCACCTGCAAGCGCCTACCAATGGTTTTATGACGGG |
| TATCCCACATTCGGTGAACACAAGCAGGAAAAAGACCTTGAATATGGSGCATGCCCAAAC |
| AACATGATGGGTACGTTCTCGGTGCGGACTGTAGGAACCTCGAAGTCCAAGTACCCATTG |
| GTGATCAGGATTTACATGAGGATGAAGCACGTCAGGGCGTGGATACCTCGCCCAATGCGT |
| AACCAAAACTACTTATTTAAAGCCAACCCAAATTATGCTGGTAACTCCATTAAACCAACT |
| GGTACCAGTCGCACAGCGATCACCACTCTCGGGAAATTTGGACAGCAATCCGGGGCTATC |
| TACGTGGGCAACTTTAGAGTGGTTAACCGCCACCTTGCTACTCATKATGACTGSGCAAAC |
| CTTGTTTGGGAAGACAGCTCCCGCGACTTGCTCGTATCATCTACCTCTGCCCAAGGTTGT |
| GACACGATTGCTCGTTGCAACTGTCAGACAGGAGTGTATTACTGTAACTCAATGAGAAAA |
| CACTATCCGGTCAGTTTCTCGAAGCCCAGTTTGATCTTCGTAGAGGCCAGCGAGTATTAC |
| CCTGCTAGATACCAGTCACACCTTATGCTTGCAGTGGGTCACTCGGAGCCAGGGGATTGC |
| GGTGGCATTCTTAGATGCCAACACGGTGTCGTAGGGATAGTTTCCACCGGGGGAAACGCC |
| CTAGTGGGGTTCGCCGATGTGAGGGATCTTCTGTGGTTGGATGATGAGGCCATGGAGCAG |
| GGCGTGACTGATTACATTAAAGGGCTTGGAGATGCTTTTGGCATGGGGTTTACAGACGCA |
| GTGTCAAGAGAAGTTGAAGCATTGAAAAATCACTTGATCGGCTCAGAGGGTGCCGTGGAG |
| AGGATCCTTAAGAACTTAGTTAAACTCATCTCTGCGCTCGTCATTGTCATCAGGAGTGAT |
| TATGACATGGTCACATTGACGGCAACACTTGCCCTGATCGGGTGTCACGGCAGCCCTTGG |
| GCCTGGATTAAGTCGAAAACAGCGTCGATTTTGGGCATACCGATGGCTCAAAAGCAGAGT |
| GCCTCTTGGTTAAAGAAGTTCAACGATGCGGCGAGTGCCGCCAAGGGGCTTGAGTGGATC |
| TCCAACAAAATCAGCAAATTTATCGATTCCCTCAAGGAGAAAATTATCCCGGCTGCTAAA |
| GAGAAAGTCGAGTTTCTAAACAATCTAAAGCAACTCCCCTTATTGGAGAACCAAATTTCT |
| AATCTCGAACAGTCAGCAGCTTCCCAGGAGGACCTCGAAGCGATGTTTGGCAACGTGTCT |
| TATCTGGCCCACTTCTGCCGCAAATTCCAACCCCTCTATGCCACGGAAGCAAAGAGGGTG |
| TATGCCCTAGAAAAGAGAATGAATAATTACATGCAGTTCAAGAGCAAACACCGTATTGAA |
| CCTGTATGCCTGATTATCAGAGGCTCGCCTGGCACTGGGAAGTCCTTGGCAACAGGGATT |
| ATTGCTAGAGCTATAGCTGACAAGTACCACTCCAGTGTGTATTCCTTACCTCCGGACCCA |
| GATCACTTTGATGGATACAAGCAACAGATCGTTACTGTTATGGATGATCTATGCCAAAAC |
| CCGGACGGGAAAGACATGTCACTATTTTGTCAGATGGTCTCCACAGTGGATTTTATACCG |
| CCTATGGCATCTCTGGAGGAGAAGGGAGTCTCATTCACCTCCAAGTTTGTGATTGCCTCC |

TABLE 1-continued

| EV71 Isehara strain full-length cDNA sequence (SEQ ID NO: 7) |
|---|
| ACTAACGCCAGTAACATCATAGTGCCAACAGTCTCGGATTCAGATGCCATCCGTCGTCCC |
| TTCTTCATGGACTGCGATATTGAGGTGACCGATTCCTATAAGACAGAGCTGGGTAGGCTT |
| GATGCAGGGAGAGCAGCTAGGCTGTGCTCTGAGAACAACACTGCAAACTTTAAACGGTGC |
| AGCCCATTAGTCTGTGGGAAAGCAATCCAGCTTAGGGATAGGAAGTCTAAGGTGAGATAC |
| AGTGTGGACACGGTGGTGAGTGAGCTTATCAGGGAGTATAACAACAGATCAGCTATTGGG |
| AATACCATCGAAGCTCTTTTCCAAGGACCCCCTAAATTTAGACCGATAAGGATTAGCCTA |
| GAGGAGAAGCCCGCACCTGATGCTATTAGTGACCTATTAGCTAGTGTCGATAGTGAAGAG |
| GTTCGCCAATACTGTAGAGATCAGGGATGGATTGTACCTGATTCTCCCACCAACGTTGAG |
| CGCCACTTGAATAGAGCTGTCTTGATCATGCAATCTATAGCCACCGTGGTAGCGGTTGTG |
| TCCCTTGTTTATGTCATCTACAAGTTGTTCGCCGGTTTTCAAGGAGCATATTCCGGCGCC |
| CCTAAGGAAGCACTCAAGAAACCAGTGTTGCGTACGGCAACTGTGCAGGGGCCAAGCTTG |

| [Table 1C] |
|---|
| GACTTCGCCCTATCTCTACTTAGGAGGAACATCAGGCAGGTCCAAACCGACCAGGGCCAC |
| TTTACAATGTTAGGAGTGCGAGACCACTTGGCTGTGCTCCCCAGACACTCCCAACCAGGA |
| AAGACCATCTGGGTTGAACACAAATTAGTGAAGATCGTGGATGCTGTGGAGCTAGTAGAT |
| GAGCAAGGAGTTAACCTAGAGCTCACACTGGTGACGCTTGACACCAACGAAAAATTTAGA |
| GACATCACAAGATTCATACCAGAAACAATTAGTCCTGCTAGTGATGCCACTTTAGTTATA |
| AATACTGAACATATGCCCAATATGTTTGTGCCAGTTGGAGATGTAGTCCAGTATGGATTT |
| TTGAACCTTAGTGGTAAGCCCACTCACAGGACTATGATGTACAATTTCCCAACAAAAGCA |
| GGACAGTGTGGTGGTGTCGTGACTCCTGTGGGTAAAGTGATTGGGATCCACATCCGTGGC |
| AACGGTAGGCAGGGTTTCTGCGCTGCCCTGAAGAGAGGATACTTTTGCAGCGAACAAGGT |
| GAGATCCAATGGATGAAGCCCAACAAAGAAACTGGCAGGTTAAACATCAACGGACCTACT |
| CGCACTAAACTTGAACCAAGTGTCTTTCATGATGTGTTCGAGGGCACTAAAGAGCCAGCA |
| GTGCTGACTAGTAAAGACCCAAGGCTGGAGGTTGACTTTGAACAGGCTCTTTTTTCAAAA |
| TACGTGGGAAACACGCTTCATGAACCTGACGAGTTTGTCAAGGAGGCGGCCTTACATTAT |
| GCCAACCAACTCAAGCAGTTAGATATTAAGACCACCAAGATGAGCATGGAGGATGCTTGT |
| TACGGTACAGAGAACCTGGAAGCTATAGACCTTCACACAAGTGCAGGATATCCATACAGT |
| GCACTGGGCATCAAGAAAAGGGATATTTTGGACCCAACAACTCGCGATGTCAGCAAGATG |
| AAATTTACATGGACAAGTATGGGTTAGATCTACCGTACTCCACTTATGTTAAAGATGAAA |
| CTCAGGGCCATCGACAAGGTCAAGAAAGGGAAGTCTCGTCTCATAGAAGCGAGCAGTCTA |
| AATGACTCAGTGTACTTGAGAATGACATTTGGGCACCTTTATGAAACTTTTCATGCCAAT |
| CCAGGTACAGTCACTGGTTCAGCTGTTGGATGCAATCCAGATGTGTTCTGGAGTAAGTTG |
| CCAATTCTACTTCCAGGATCGCTTTTTGCATTTGACTACTCGGGGTATGACGCTAGTCTC |
| AGCCCAGTGTGGTTCAGGGCGCTGGAGATAGTCCTACGGGAAATTGGGTACTCCGAGGAC |
| GCAGTGTCTCTCATAGAAGGGATCAATCACACTCACCATGTGTACCGCAATAAAACTTAT |
| TGTGTTCTTGGGGGAATGCCCTCAGGTTGCTCAGGCACCTCCATTTTCAACTCGATGATC |
| AATAACATCATTATTAGGACACTCCCGATTAAAACATTCAAAGGGATAGATCTAGATGAA |
| TTGAATATGGTGGCCTACGGGGATGATGTGTTGGCTAGTTACCCCTTCCCAATTGACTGT |
| CTGGAATTGGCAAGAACAGGCAAGGAGTATGGTTTAACTATGACCCCTGCCGACAAGTCA |

TABLE 1-continued

| EV71 Isehara strain full-length cDNA sequence (SEQ ID NO: 7) |
|---|
| CCTTGCTTTAATGAAGTTACATGGGAGAATGCCACTTTCTTGAAGAGAGGATTCTTGCCT |
| GATCATCAATTCCCGTTCCTCATCCACCCCACGATGCCAATGAGGGAGATTCACGAATCT |
| ATTCGTTGGACTAAAGATGCACGAAGTACTCAAGATCACGTGCGCTCTCTCTGCTTATTA |
| GCATGGCACAACGGGAAAGAGGAGTATGAAAAATTTGTGAGTACAATCAGATCAGTTCCA |
| ATTGGAAAGGCATTGGCAATACCGAATTTTGAGAATCTGAGAAGAAATTGGCTCGAATTG |
| TTTTAAATTTACAGTTTGTAACTGAACCCTACCAGTAATCTGGTCGTGTTAATGACTGGT |
| GGGGGTAAATTTGTTATAACCAGAATAGCAAAAAAAAAAAAAAAAAAAAAAAAA |

The obtained full-length cDNA was inserted to the NotI/SalI cleavage site of pSAV14 vector and cloned. The resultant was subjected to a transcription reaction as a template in an in vitro ascription using MEGAscript® T7 kit (Ambion, Inc.) to obtain full-length genomic RNA. Then, $2\times10^6$ RD-SCARB2 cells were transfected with 4 μg of the full-length genomic RNA using Lipofectamine® 2000. On the next day or on the day after the next, the cells were collected when a cytopathic effect (CPE) was observed in 90% or more of the cells. The collected cells were frozen and thawed three times and a sonicator was used so that the cells were completely homogenized to release viruses. Then, cell debris was removed by centrifugation, and the supernatant was collected as a virus fluid.

RD-SCARB2 cells ($1\times10^6$ cells) were infected with the harvested virus at MOI=0.01. A cytopathic effect (CPE) was observed over 5 days. The cells were collected when marked CPE was observed. The cultured virus was harvested by the same procedures as above. This virus was used as EV71 with a passage number of P0. RD-SCARB2 cells were infected with EV71 with a passage number of P0 by the same procedures as above to obtain EV71 with a passage number of P1. The same procedures as above were repeated using EV71 with a passage number of P1 to obtain EV71 with a passage number of P2 (RD-SCARB2(P2)). Then, EV71 viruses with passage numbers of P3 to P5 were further obtained by the continuous passage of RD-SCARB2(P2) by the same procedures as above using the cells obtained in each of the above Items 1 and 2 instead of RD-SCARB2 cells.

The amino acid sequence of the capsid protein VP1 of each of the obtained EV71 viruses with passage numbers of P2 to P5 was analyzed by the following procedures: RNA was extracted from EV71 viruses with passage numbers of P0 to P3, and cDNA was synthesized by reverse transcription. A partial region (corresponding to the 58th to 297th amino acids of PV1) of the VP1 gene (GenBank Accession No. AB177816) was amplified using primers having sequences given below. The nucleotide sequence of the amplified DNA fragment was analyzed by sequencing.

```
[Formula 5]
                              (SEQ ID NO: 8)
Forward: CNAYAYAATATATTA

                              (SEQ ID NO: 9)
Reverse: ANACNARRTTNCCCATCA
```

The results are shown in Table 2. In EV71 passaged using the wild-type RD cells, the 145th amino acid glutamic acid (E) of VP1 was mutated to glutamine (Q) by one passage. In contrast, in EV71 passaged using RD-ΔEXT1-SCARB2 and RD-ΔEXT2-SCARB2, it was confirmed that the 145th amino acid glutamic acid of VP1 was maintained without being mutated even by 3 repeated passages. These results demonstrated that virulent EV71 having glutamic acid (E) as the 145th amino acid of VP1 can be stably cultured by use of a host cell expressing no HS and overexpressing SCARB2.

TABLE 2

| | 145th amino acid of VP1 | | |
|---|---|---|---|
| Host cell | P2 | P3 | P5 |
| RD | — | Q | Q |
| RD-ΔEXT1 | — | E | Q |
| RD-ΔEXT2 | — | E | Q |
| RD-SCARB2 | E | E | Q/E |
| RD-ΔEXT1-SCARB2 | — | E | E |
| RD-ΔEXT2-SCARB2 | — | E | E |

4. Change in Virulence of EV71 by Passages—(1)

EV71 viruses with passage numbers of P1 to P3 were prepared by continuous passage using the cells obtained in each of the above Items 1 and 2 by the same procedures as in the above Item 3 except that a 2716-Yamagata-03 strain (obtained from Yamagata Prefectural Institute of Public Health) cultured by one passage in RD-SCAR132 cells was used as EV71 with a passage number of P0. The pathogenicity thereof was analyzed by the following procedures: hSCARB2-Tg10 (Proc. Nat. Acad. Sci. U.S.A., Vol. 110, No. 36, pp. 14753-14758) was used as a transgenic mouse expressing human SCARB2. 0.5 ml of each EV71 described above with $10^6$ $TCID_{50}$/ml was intraperitoneally administered to 6- to 7-week-old hSCARB2-Tg10 (10 mice for each group). After the administration, live or dead status, paralytic symptoms, and changes in body weight were observed every day over 2 weeks. The rate of paralysis indicates the percentage of mice confirmed to have the symptoms of complete or incomplete paralysis in any of the extremities over 2 days or longer. The rate of change in body weight was calculated with the body weight before administration defined as 100%.

The results are shown in Tables 3 to 5. EV71 passaged using RD-ΔEXT1-SCARB2 and RD-ΔEXT2-SCARB2 was found to maintain pathogenicity equal to or greater than that of P0 even by 3 repeated passages. These results demonstrated that virulent EV71 can be stably cultured by use of a host cell expressing no HS and overexpressing SCARB2.

TABLE 3

| Rate of paralysis (%) 2 weeks after administration of EV71 | | | |
|---|---|---|---|
| Host cell | P0 | P1 | P3 |
| RD | — | 10 | 0 |
| RD-ΔEXT1 | — | — | 0 |
| RD-ΔEXT2 | — | 0 | 0 |
| RD-SCARB2 | 90 | 60 | 0 |
| RD-ΔEXT1-SCARB2 | — | 100 | 100 |
| RD-ΔEXT2-SCARB2 | — | 100 | 100 |

TABLE 4

| Mortality (%) 2 weeks after administration of EV71 | | | |
|---|---|---|---|
| Host cell | P0 | P1 | P3 |
| RD | — | 0 | 0 |
| RD-ΔEXT1 | — | — | 0 |
| RD-ΔEXT2 | — | 0 | 0 |
| RD-SCARB2 | 50 | 30 | 0 |
| RD-ΔEXT1-SCARB2 | — | 90 | 100 |
| RD-ΔEXT2-SCARB2 | — | 60 | 70 |

TABLE 5

| Change in body weight (%) 6 days after administration of EV71 | | | |
|---|---|---|---|
| Host cell | P0 | P1 | P3 |
| RD | — | 99.6 | 96.7 |
| RD-ΔEXT1 | — | — | 96.1 |
| RD-ΔEXT2 | — | 95.6 | 97.4 |
| RD-SCARB2 | 83.3 | 91.0 | 96.9 |
| RD-ΔEXT1-SCARB2 | — | 76.0 | All died |
| RD-ΔEXT2-SCARB2 | — | 72.7 | 73.0 |

Figure 2:
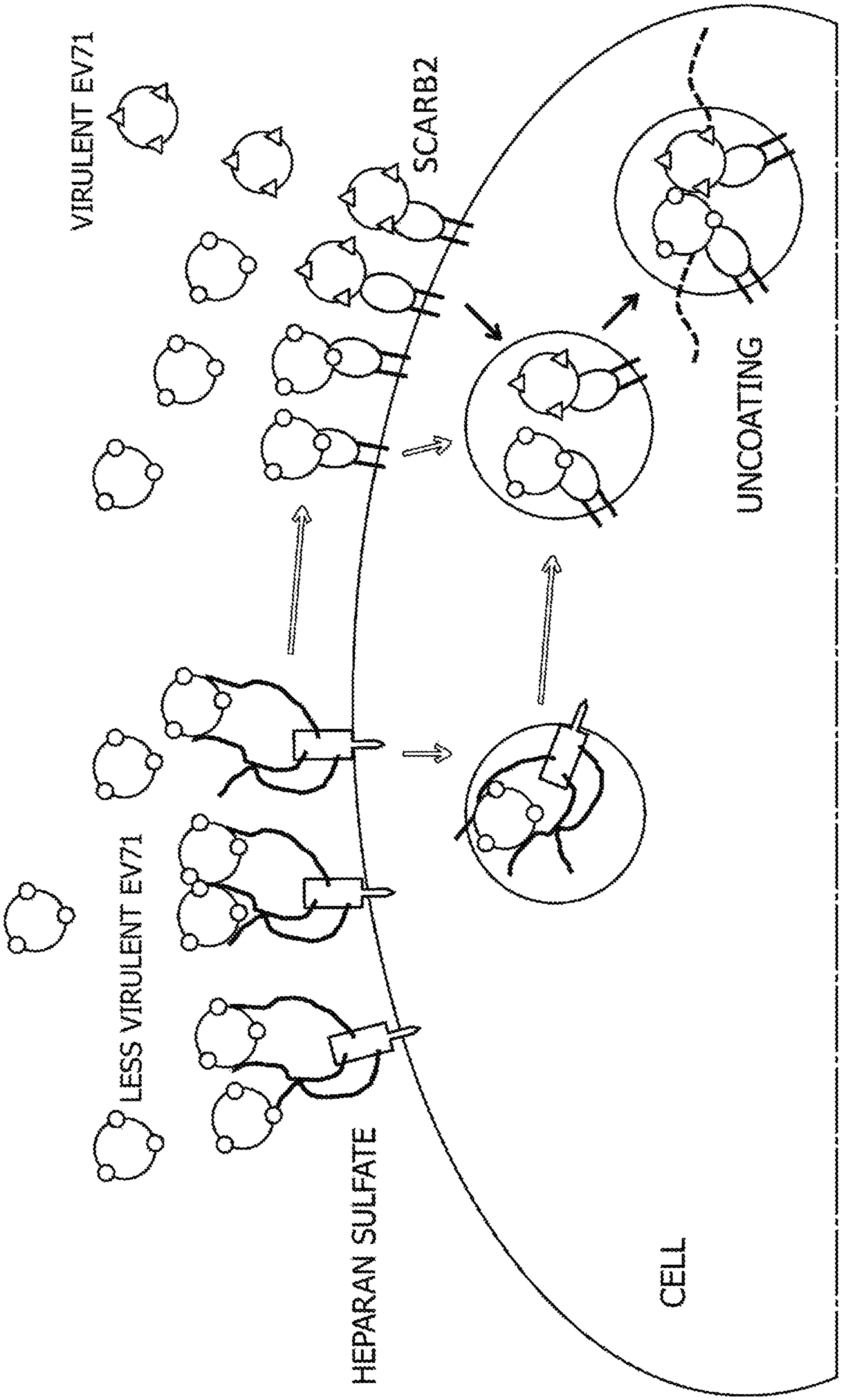
FIG. 2 is a schematic diagram showing a mechanism underlying EV71 infection mediated by heparan sulfate or SCARB2.
Figure 3A:
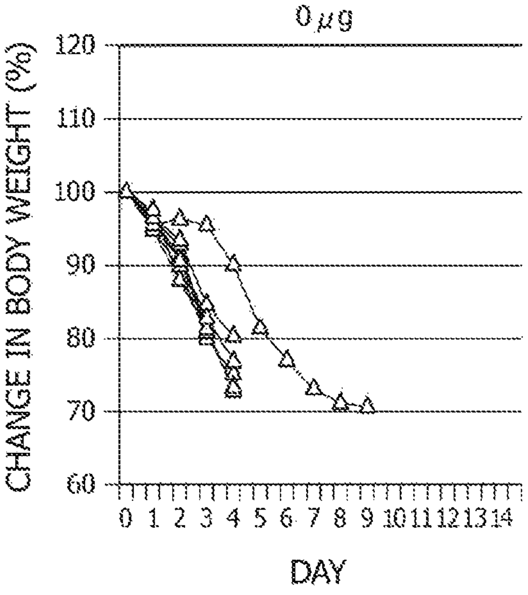
FIG. 3 is a graph showing change in the body weights of (vaccination (−) or (+)) challenged with a virulent EV71 (N772 strain).
Figure 3B:
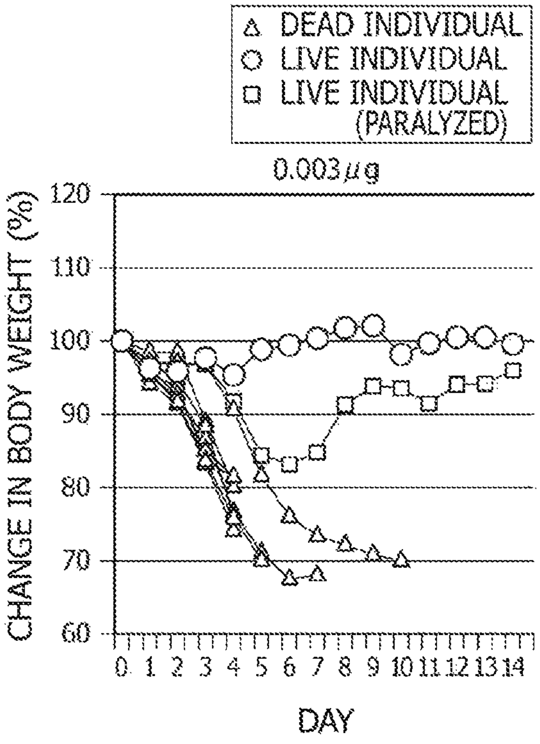
Figure 3C:
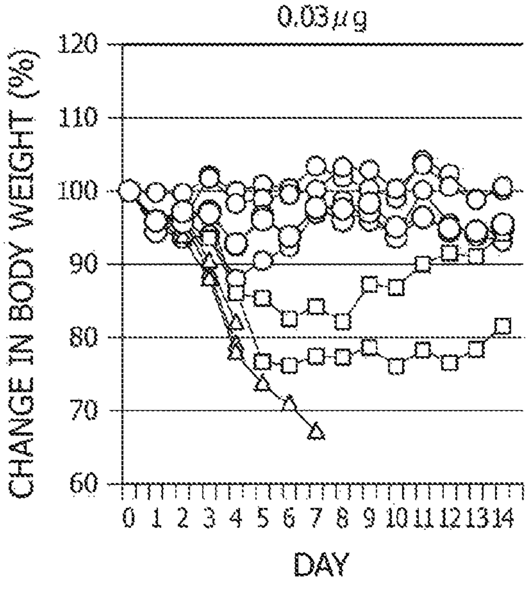
Figure 3D:
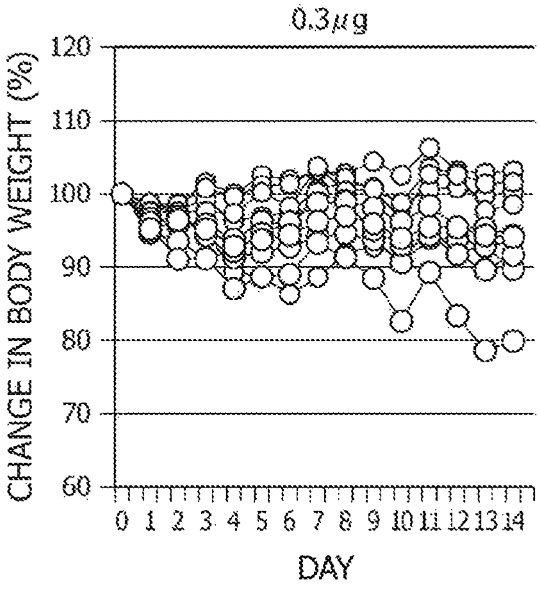

A hypothesized mechanism underlying the attenuation of EV71 based on the results described above is shown in FIG. 2. Virulent EV71 having glutamic acid (E) as the 145th amino acid of the VP1 capsid protein (VP1-145E) and less virulent EV71 having glycine (G) or glutamine (Q) as this amino acid (VP1-145G or VP1-145Q) both infect a host cell via SCARB2 (black arrows). However, when HS is expressed on cell surface, the less virulent EV71 is attracted by HS and thereby comes close to the cell surface. Thus, the less virulent EV71 more easily infects the host cell via SCARB2 than the virulent EV71 does. Furthermore, less virulent EV71 taken up into the cell by binding to HS also joins into the route of infection mediated by SCARB2 and then grow (white arrows). As a result, the less virulent EV71 grows preferentially, probably causing the attenuation of EV71 with increase in numbers of passage.

5. Change in Virulence of EV71 by Passages—(2)

Cells were transfected with full-length genomic RNA and a cultured virus was harvested by the same procedures as in the above Item 3 except that RD-ΔEXT1-SCARB2 was used as a host cell instead of RD-SCARB2. A virus obtained by culturing the harvested virus by one passage (RD-ΔEXT1-SCARB2(P1)) and EV71 with a passage number of P0 prepared using RD-SCARB2 in the above Item 3 (RD-SCARB2(P2)) were each intravenously administered to each 10-week-old hSCARB2-Tg10 (10 mice for each group). A survival rate was compared 2 weeks after administration.

The results are shown in Table 6. RD-ΔEXT1-SCARB2 (P1) was found to have virulence 1000 or more times higher than that of RD-SCARB2(P2).

TABLE 6

| Comparison of virulence between RD-SCARB2(P2) and RD-ΔEXT1-SCARB2(P1) | | | | | | | | |
|---|---|---|---|---|---|---|---|---|
| Host cell | Amount of virus inoculated (log $TCID_{50}$) | | | | | | | log |
| (passage number) | 1 | 2 | 3 | 4 | 5 | 6 | 7 | $LD_{50}$ |
| RD-SCARB2(P2) | 100 | 100 | 100 | 100 | 100 | 90 | 10 | >6.5 |
| RD-ΔEXT1-SCARB2(P1) | 90 | 100 | 90 | 20 | 0 | 0 | 0 | 3.5 |

6. Vaccine Efficacy Test Using Virulent EV71—(1)

Each hSCARB2-Tg10 transgenic mouse was immunized by the following procedures using each of a SK-EV006 (VP1-145G) strain (obtained from National Institute of Infectious Diseases of Japan) as a live vaccine against EV71, and this strain fixed in formalin as an inactivated vaccine.

(Immunization with Live Vaccine)

The SK-EV006 (VP-145G) strain with $10^6 TCID_{50}$ was intraperitoneally administered to each 4-week-old hSCARB2-Tg10 transgenic mouse (initial immunization). Then, the same administration as above was also performed at the age of 8 weeks (booster). PBS was administered to a control group.

(Immunization with Inactivated Vaccine)

An amount of 100 μl of formalin-fixed SK-EV006 (VP-145G) was mixed with an equal amount of Alhydrogel® (InvivoGen) to obtain an inactivated vaccine preparation. An amount of 0.3 μg of the inactivated vaccine preparation was subcutaneously administered to each 4-week-old hSCARB2-Tg10 transgenic mouse (initial immunization). Then, the same administration as above was also performed at the age of 8 weeks (booster). The same amount as above of Alhydrogel/PBS was administered to a control group.

Blood was collected from each mouse at the age of 10 weeks to obtain serum. A neutralizing antibody titer in the serum was evaluated by the standard plaque reduction neutralization test (PRNT). Briefly, the obtained serum was serially diluted and mixed with a challenge virus (500 pfu), followed by plaque assay using RD cells and a SK-EV006 (VP-145G) strain. The reciprocal of the maximum dilution of serum that achieved 80% decrease in the number of plaques was recorded as the neutralizing antibody titer.

On the day following the blood collection, a challenge virus was intravenously administered to each mouse. The challenge virus used was an Isehara strain (RD-SCARB2 (P2) prepared in the above Item 3). The dose of the challenge virus was set to an amount of 10 to 100 times $LD_{50}$ determined in advance by infecting a 10-week-old mouse with the challenge virus. After the challenge, live or dead status and paralytic symptoms were observed every day over 2 weeks. The rate of paralysis was calculated as described in the above Item 5.

The results are shown in Tables 7 and 8. When the live vaccine or the inactivated vaccine is administered, elevation in neutralizing antibody titer and remarkable decrease in death rate and rate of paralysis were observed, indicating protection against challenge with virulent EV71. From these results, it was confirmed that anti-EV71 vaccine can be screened for using an adult hSCARB2-Tg10 mouse.

TABLE 7

| Protective effect of live vaccine (challenge: Isehara RD-SCARB2(P2) with $10^7$ $TCID_{50}$) | | | |
|---|---|---|---|
| Amount of vaccination ($log_{10}$ $TCID_{50}$) | Neutralizing antibody titer (geometric mean) | Death rate (%) | Rate of paralysis (%) |
| 0 | <8 | 90 | 90 |
| 6.0 | >256 | 0 | 10 |

TABLE 8

| Protective effect of inactivated vaccine (challenge: Isehara RD-SCARB2(P2) with $10^7$ $TCID_{50}$) | | | |
|---|---|---|---|
| Amount of vaccination (μg/shot) | Neutralizing antibody titer (geometric mean) | Death rate (%) | Rate of paralysis (%) |
| 0 | <16 | 75 | 75 |
| 0.3 | >256 | 0 | 0 |

7. Vaccine Efficacy Test Using Virulent EV71—(2)

Each hSCARB2-Tg10 transgenic mouse was immunized with an inactivated vaccine in the same way as in the above Item 6. The plaque assay was conducted by the same procedures as in the above Item 6 except that blood was collected from each mouse at the age of 21 weeks. On the day following the blood collection, challenge infection was performed by the same procedures as in the above Item 6 except that RD-ΔEXT1-SCARB2(P1) ($LD_{50}=19^{3.5}$) prepared in the above Item 3 was used as a challenge virus. The death rate and the rate of paralysis were calculated.

The results are shown in Table 9. In the case of using RD-ΔEXT1-SCARB2(P1) as a challenge virus, it was confirmed that sufficient challenge is attainable by a smaller amount of the virus than that of RD-SCARB2(P2) because of its high virulence. These results demonstrated that EV71 passage-culturing in a host cell expressing no HS and overexpressing SCARB2 is useful as a challenge virus for vaccine assay.

TABLE 9

| Protective effect of inactivated vaccine (challenge: Isehara RD-ΔEXT1-SCARB2(P1) with 2 × $10^5$ $TCID_{50}$) | | |
|---|---|---|
| Amount of vaccination (μg/shot) | Death rate (%) | Rate of paralysis (%) |
| 0 | 100 | 100 |
| 0.003 | 0 | 33 |
| 0.03 | 17 | 17 |
| 0.3 | 0 | 13 |

8. Vaccine Efficacy Test Using Virulent EV71—(3)

In addition to the Isehara strain (subgenogroup C2), virulent EV71 differing in subgenogroup (Y90-3896 strain (subgenogroup C1) (obtained from Virus Research Center, Sendai), N772 strain (subgenogroup C4) (obtained from Virus Research Center, Sendai). C7/Osaka strain (subgenogroup B4) (obtained from National Institute of Infectious Diseases, Japan), and 2716-Yamagata-03 strain (subgenogroup B5) (obtained from Yamagata Prefectural Institute of Public Health)) were prepared as challenge viruses for vaccine assay. The full-length cDNA sequence of the virulent EV71 and primer sets used for cDNA amplification are shown below.

TABLE 10

| Y90-3896 strain (subgenogroup C1)(SEQ ID NO: 10) |
|---|
| [Table 10A] |
| TTAAAACAGCCTGTGGGTTGCACCCACCCACAGGGCCCACTGGGCGCCAGCACTCTGGTA |
| CTTAGGTACCTTTGTGCGCCTGTTTTATCTCCCTTCCCCCGAAGTAACTTAGAAGCTGTG |
| AGCTAACGATCAACAGTAGGTGTGACATACCAGTCATATCTTGATCAAGCACTTCTGTTT |
| CCCCGGACTGAGTATCAATAGGCTGCTCGCGCGGCTGAAAGAGAAAACGTTCGTCACCCG |
| GCCAACTACTTCGAGAAGCTTAGTACCACCATGAACGAGGCAGAGTGTTTCGCTCGGCAC |
| AACCCCAGTGTAGATCAGGCTGATGAGTCACTGCAATCCCCATGGGCGACCATGGCAGTG |
| GCTGCGTTGGCGGCCTGCCCATGGAGAAATCCATGGGACGCTCTAATTCTGACATGGTGC |
| GAAGAGCCTATTGAGCTAGCTGGTAGTCCTCCGGCCCCTGAATGCGGCTAATCCTAACTG |
| CGGAGCACACACCCACAAGCCAGTGGGCAGTGTGTCGTAACGGGCAACTCTGCAGCGGAA |
| CCGACTACTTTGGGTGTCCGTGTTTCCTTTTATTCTTGTATTGGCTGCTTATGGTGACAA |
| TCAAAGAGTTGTTACCATATAGCTATTGGATTGGCCATCCGGTGTGCAACAGAGCAATTA |
| TTTACCTATTTATTGGTTTTGTACCATTGACACTGAAGTCTGTGATTACCCTTAATTTTA |
| TTTTGACCCTCAACACAGTCAAACATGGGCTCACAGGTGTCCACACAACGCTCCGGCTCA |
| CATGAAAACTCTAACTCAGCTACTGAGGGCTCCACCATAAACTACACTACTATTAATTAC |
| TACAAGGACTCCTATGCCGCTACAGCAGGCAAACAGAGCCTCAAGCAGGATCCAGATAAG |
| TTTGCAAATCCTGTCAAAGATATTTTCACTGAAATGGCAGCGCCACTAAAGTCCCCATCC |
| GCTGAAGCATGTGGATACAGCGACCGAGTAGCGCAGTTAACTATTGGCAACTCTACCATC |

TABLE 10-continued

| Y90-3896 strain (subgenogroup C1)(SEQ ID NO: 10) |
| --- |
| ACTACACAAGAAGCAGCAAACATTATAGTTGGCTATGGTGAATGGCCCTCCTACTGCTCG |
| GATTCTGACGCTACAGCAGTGGACAAACCAACGCGCCCAGATGTTTCGGTGAACAGGTTT |
| TACACATTGGACACCAAATTATGGGAGAAATCGTCCAAGGGATGGTACTGGAAATTCCCG |
| GATGTGTTAACAGAAACCGGGGTTTTTGGCCAGAATGCACAATTCCATTACCTCTATCGG |
| TCAGGGTTCTGCATTCACGTGCAATGCAATGCTAGCAAATTCCATCAGGGAGCGCTCCTA |
| GTCGCTGTTCTCCCGGAGTATGTCATTGGGACAGTGGCGGGTGGCACAGGGACGGAGGAT |
| AGCCACCCCCCTTACAAGCAGACTCAACCCGGCGCTGATGGTTTTGAGTTACAACATCCG |
| TACGTGCTTGACGCTGGCATTCCAATATCACAATTAACAGTGTGCCCACATCAGTGGATT |
| AACTTGAGGACCAACAATTGTGCCACAATAATAGTGCCATACATTAATGCACTGCCCTTT |
| GATTCTGCCTTAAACCATTGTAACTTTGGCCTACTGGTTGTGCCCATTAGCCCGTTGGAC |
| TTCGACCAAGGAGCGACGCCAGTGATCCCCATTACTATCACATTGGCCCCAATGTGTTCT |
| GAATTTGCAGGTCTTAGGCAAGCGGTCACGCAAGGATTTCCTACTGAGCTGAAACCTGGC |
| ACAAACCAATTTTTAACCACTGACGATGGCGTTTCAGCGCCCATTCTGCCAAACTTTCAC |
| CCCACCCCATGCATCCATATACCTGGTGAGGTTAGAAATTTGCTAGAGCTATGCCAGGTG |
| GAGACTATCTTAGAGGTCAACAATGTACCCACGAATGCCACTAGTTTAATGGAGAGACTG |
| CGCTTTCCGGTCTCAGCCCAAGCAGGAAAAGGCGAGTTGTGTGCAGTGTTCAGAGCCGAT |
| CCTGGGCGAAATGGGCCTTGGCAATCTACCTTGTTGGGCCAGTTGTGCGGGTACTACACT |
| CAATGGTCAGGATCACTGGAAGTCACGTTCATGTTCACTGGGTCCTTTATGGCCACCGGC |
| AAGATGCTTATAGCTTACACGCCACCAGGAGGCCCTTTGCCCAAGGACCGGGCGACCGCC |
| ATGTTGGGTACGCATGTCATCTGGGATTTTGGGCTGCAATCGTCTGTCACCCTTGTAATA |
| CCATGGATCAGCAACACTCATTACAGAGCGCATGCTCGAGATGGGGTGTTCGACTATTAC |
| ACTACAGGCCTGGTTAGTATATGGTATCAGACGAACTATGTGGTTCCCATTGGAGCACCC |
| AATACAGCCTATATAATAGCGTTAGCGGCAGCCCAGAAGAATTTTACCATGAAATTGTGT |
| AAGGATGCCAGTGATATCTTACAGACAGGCACTATTCAGGGGGATAGGGTGGCAGATGTG |
| ATTGAGAGTTCTATAGGGGATAGTGTGAGCAGAGCTCTCACTCAAGCTCTACCGGCACCC |
| ACAGGCCAGGACACGCAGGTAAGCAGCCATCGATTGGATACTGGCAAAGTTCCAGCACTC |
| CAAGCCGCTGAGATTGGAGCATCATCAAATGCTAGTGATGAGAGTATGATTGAGACACGA |
| TGTGTTCTTAATTCGCACAGCACAGCTGAGACCACTCTCGATAGTTTCTTCAGCAGAGCG |
| [Table 10B] |
| GGATTAGTTGGGGAGATAGACCTTCCTCTTGAAGGCACAACCAACCCAAATGGTTATGCA |
| AATTGGGACATAGATATAACAGGTTATGCGCAGATGCGTAGAAAGGTGGAGCTGTTCACC |
| TACATGCGTTTTGACGCAGAATTCACCTTCGTCGCGTGCACGCCCACCGGGGAGGTTGTC |
| CCACAATTACTCCAATATATGTTTGTGCCACCTGGGGCCCCCAAGCCAGAATCCAGAGAA |
| TCCCTCGCATGGCAAACTGCCACCAATCCCTCGGTTTTTGTTAAGCTATCAGACCCCCCA |
| GCGCAGGTTTCAGTTCCATTCATGTCACCTGCGAGTGCTTACCAATGGTTTTATGACGGA |
| TATCCCACGTTCGGTGAACACAAGCAGGAAAAAGACCTTGAATACGGGGCATGTCCAAAC |
| AACATGATGGGCACGTTCTCAGTGCGGACCGTAGGAACCTCGAAGTCCAAGTACCCTTTA |
| GTAATTAGGATTTATATGAGGATGAAGCACGTCAGGGCATGGGTACCTCGTCCAATGCGC |
| AACCAAAACTATCTATTCAAAGCCAACCCAAATTACGCCGGCAACTCCATTAAGCCAACC |

TABLE 10-continued

| Y90-3896 strain (subgenogroup C1)(SEQ ID NO: 10) |
|---|
| GGTGCCAGTCGCACAGCGATCACCACTCTCGGAAAATTTGGGCAACAATCCGGGGCCATC |
| TATGTGGGTAACTTTAGAGTGGTTAATCGCCATCTTGCCACTCACAATGATTGGGCGAAC |
| CTTGTTTGGGAAGACAGCTCTCGCGACTTACTCGTATCATCTACCACCGCTCAGGGTTGT |
| GATACGATAGCCCGTTGCGATTGTCAGACAGGAGTGTACTATTGTAACTCAAGGAGAAAA |
| CACTACCCGGTTAGTTTCTCAAAACCCAGCTTGATCTTTGTAGAGGCCAGCGAGTACTAC |
| CCAGCCAGGTATCAGTCACACCTCATGCTCGCAGTGGGTCACTCAGAACCAGGAGATTGC |
| GGTGGCATACTCAGATGCCAACACGGTGTTGTAGGGATAGTTTCTACCGGGGGAAATGGC |
| CTGGTGGGGTTCGCCGACGTGAGGGACCTTCTGTGGTTGGATGATGAAGCCATGGAACAG |
| GGTGTGTCTGATTACATTAAAGGGCTTGGTGATGCTTTCGGCATGGGATTCACAGACGCA |
| GTGTCAAGAGAGGTTGAAGCCTTGAAAAGTCATTTGATCGGTTCAGAGGGCGCCGTGGAG |
| AAGATTCTTAAGAACTTAGTAAAACTCATCTCTGCGCTTGTCATTGTCATCAGGAGTGAC |
| TACGACATGGTCACATTGACGGCAACGCTTGCCCTGATTGGGTGCCATGGGAGCCCTTGG |
| GCCTGGATTAAGTCGAAAACAGCTTCAATTTTGGGTATACCAATGGCCCAGAAGCAGAGC |
| GCCTCTTGGTTAAAGAAGTTCAACGATGCGGCGAGTGCCGCTAAGGGGCTTGAGTGGATC |
| TCCAATAAAATCAGTAAATTTATCGATTGGCTCAAGGAGAAAATCATCCCGGCTGCTAAA |
| GAAAAAGTCGANTTTCTAAATAACTTGAAGCAACTTCCTTTATTGGAAAACCAAATCTCT |
| AACCTTGAACAGTCAGCAGCTTCGCAGGAGGACCTTGAAGCGATGTTTGGCAACGTGTCC |
| TACTTGGCCCACTTTTGCCGCAAATTCCAACCTCTCTATGCCACAGAAGCAAAGAGGGTG |
| TACGCCTTAGAAAAAAGAATGAACAATTACATGCAGTTCAAGAGCAAACACCGTATTGAA |
| CCTGTGTGCTTGATCATTAGAGGCTCACCTGGTACTGGGAAGTCTTTAGCAACAGGGATT |
| ATCGCTAGAGCTATAGCAGATAAGTATCACTCTAGTGTGTATTCCCTACCTCCAGACCCA |
| GATCATTTTGATGGATATAAACAACAGATTGTCACTGTTATGGATGACCTCTGCCAAAAT |
| CCGGATGGGAAAGACATGTCACTATTCTGTCAGATGGTTTCCACAGTGGACTTTATACCG |
| CCTATGGCATCCCTGGAGGAGAAGGGAGTCTCATTCACCTCCAAGTTTGTGATTGCCTCC |
| ACTAACGCTAGCAACATCATAGTAGCAACAGTCTCGGATTCAGATGCCATCCGTCGTCGG |
| TTCTTTATGGACTGTGATATTGAAGTGACCGATTCCTATAAGACAGATTTGGGTAGGCTT |
| GATGCAGGGAGAGCGGCCAGGCTGTGTTCTGAGAACAACACTGCAAATTTCAAACGGTGC |
| AGCCCACTAGTATGTGGGAAAGCAATCCAGCTTAGGGATAGAAAGTCCAAGGTGAGATAC |
| AGTGTGGACACAGTGGTGAGTGAGCTCATTAGGGAATATAACAACAGGTCAGCTATTGGG |
| AATACCATCGAAGCTCTTTTTCAGGGGCCCCCTAAATTCAGACCGATAAGGATTAGTCTG |
| GAGGAGAAGCCCGCACCTGACGCTATCAGTGATCTGCTGGCTAGTGTTGATAGTGAAGAA |
| GTCCGCCAATACTGTAGAGATCAAGGATGGATTGTGCCTGATACTCCCACCAACGTTGAG |
| CGCCACTTGAATAGAGCTGTCTTGATTATGCAATCTGTAGCCACCGTGGTGGCAGTTGTG |
| TCCCTTGTTTACGTCATCTACAAGTTGTTTGCCGGTTTCCAAGGAGCATATTCCGGCGCC |
| CCCAAGCAAACACTTAAGAAACCGGTGCTGCGTACAGCAACCGTGCAGGGACCGAGCTTG |

| [Table 10C] |
|---|
| GACTTCGCCCTATCTTTACTCAGAAGGAACATTAGGCAGGTCCAAACCGATCAGGGCCAC |
| TTCACAATGCTAGGAGTGCGGGACCACTTGGCTGTACTCCCTAGACACTCCCAACCAGGA |
| AAGACCATTTGGGTTGAGCACAAACTGGTGAAGATCGTAGACGCCGTGGAGTTGGTAGAT |

TABLE 10-continued

| Y90-3896 strain (subgenogroup C1)(SEQ ID NO: 10) |
|---|
| GAACAAGGGGTTAACCTAGAGCTTACACTGGTAACGCTTGACACCAATGAAAAATTCAGA |
| GACATCACAAGGTTCATACCAGAAACAATTAGTCCTGCTAGTGATGCCACTCTAGTCATA |
| AATACTGAACATATGCCCAGCATGTTTGTGCCGGTTGGAGATGTGGTCCAGTATGGATTT |
| TTGAATCTTAGTGGCAAGCCCACTCACCGGACTATGATGTACAACTTCCCAACAAAGGCA |
| GGACAGTGTGGTGGTGTTGTGACTGCTATAGGTAAAGTGATTGGGATCCACATTGGTGGT |
| AATGGTAGGCAAGGTTTCTGTGCTGCTCTGAAGAGGGGGTACTTTTGTAGTGAACAGGGT |
| GAGATCCAGTGGATGAAGCCCAACAAAGAAACTGGCAGGTTGAACATCAATGGGCCTACT |
| CGCACCAAGCTTGAGCCAAGTGTTTTCCATGATGTGTTCGAGGGCACCAAAGAGCCAGCA |
| GTGCTGACTAGCAAAGACCCAAGGCTGGAAGTCGACTTTGAGCAGGCTTTGTTCTCAAAA |
| TATGTAGGAAACACGCTTCACGAGCCCGACGAGTTTGTCAGGGAGGCGGCTTTGCACTAT |
| GCCAACCAACTCAAACAGTTAGATATCAAAACCACCAAAATGAGCATGGAGGATGCTTGT |
| TATGGTACAGAGAACCTGGAAGCTATAGATCTTCACACTAGTGCGGGATACCCATACAGT |
| GCACTAGGCATTAAGAAAAGGGATATTTTGGATCCAATAACTCGTGATGTTAGTAAAATG |
| AAATTCTACATGGACAAATATGGGTTGGATCTACCGTATTCCACTTATGTCAAAGATGAA |
| CTCAGGGCCATTGATAAGATCAAGAAAGGGAAGTCCCGTCTCATAGAAGCGAGCAGTCTA |
| AATGACTCAGTGTACTTAAGGATGACATTTGGGCACCTTTATGAAACCTTCCACGCCAAT |
| CCGGGTACAGTCACTGGTTCAGCTGTTGGATGCAACCCAGATGTGTTTTGGAGTAAGTTA |
| CCAATTCTACTCCCAGGATCGCTTTTTGCGTTTGACTACTCGGGGTATGACGCCAGTCTC |
| AGCCCAGTGTGGTTTAGGGCGTTGGAGATAGTCCTGCGGGAAATTGGATACTCTGAGGAC |
| GCAGTGTCTCTCATAGAAGGGATCAATCACACCCACCATGTGTATCGCAATAAAACTTAT |
| TGTGTTCTTGGGGGAATGCCCTCAGGTTGCTCAGGCACTTCCATTTTCAACTCGATGATC |
| AATAATATCATTATCAGGACACTATTGATTAAAACATTCAAAGGGATAGATCTAGATGAA |
| TTGAATATGGTGGCCTACGGGGATGATGTGTTAGCTAGTTATCCCTTCCCAATTGACTGT |
| CTAGAGCTGGCAAAGACAGGCAAGGAGTATGGCTTGACTATGACCCCTGCCGACAAATCA |
| CCCTGCTTTAATGAAGTTACGTGGGAGAATGCCACCTTCTTAAAGAGAGGATTTCTGCCT |
| GATCATCAATTTCCGTTCCTCATCCACCCTACGATGCCAATGAAGGAAATTCACGAGTCC |
| ATTCGCTGGACCAAAGACGCACGAAATACCCAAGATCACGTGCGCTCCCTCTGCTTGTTA |
| GCATGGCACAACGGGAAAGAGGAGTATGAAAAATTTGTGAGCGCAATCAGATCGGTTCCA |
| ATTGGGAAAGCGTTAGCCCTACCAAATTTTGAGAATCTGAGGAGAAATTGGCTCGAATTG |
| TTTTAAATTTACAGTTTGTAACTGAACCCCACCAGAAATCTGGTCGCGTTAATGACTGGT |
| GGCCGTAAATTTGTTATAACCAGAATAGCAAAAAAAAAAAAAAAAAAAAA |

TABLE 11

| N772 strain (subgenogroup C4)(SEQ ID NO: 11) |
|---|
| [Table 11A] |
| TTAAAACAGCCTGTGGGTTGTACCCACTCACAGGGCCCACTGGGCGCTAGCACTCTGGTA |
| TCTCGGTACCTTTGTGCGCCTGTTTTATACCCCCCCCCCCTCAGTGAAACTTAGAAGCAG |
| CAAACAACGATCAATAGCAGACATAACACTCCAGTTATGTCTCGATCAAGCACTTCTGTT |

TABLE 11-continued

| N772 strain (subgenogroup C4)(SEQ ID NO: 11) |
|---|
| TCCCCGGACCGAGTATCAATAGACTGCTCGCGCGGTTGAAGGAGAAAACGTTCGTTATCC |
| GGCTAACTACTTCGGGAAACCTAGTAACACCATGAAAGTTGCGGAGAGCTTCGTTCAGCA |
| CTCCCCCAGTGTAGATCAGGTCGATGAGTCACCGCATTCCCCACGGGCGACCGTGGCGGT |
| GGCTGCGTTGGCGGCCTGCCCATGGGGTAACCCATGGGGCGCTCTAATACGGACATGGTG |
| CGAAGAGTCTACTGAGCTAGTTAGTAGTCCTCCGGCCCCTGAATGCGGCTAATCCCAACT |
| GCGGAGCACACGCCCACAAGCCAGCGGGTAGTGTGTCGTAACGGGCAACTCTGCAGCGGA |
| ACCGACTACTTTGGGTGTCCGTGTTTCCTTTTATCTTTATATTGGCTGCTTATGGTGACA |
| ATTAAAGAATTGTTACCATATAGCTATTGGATTGGCCATCCGGTGTGCAACAGAGCAATT |
| GTTTACCTATTTATTGGTTTTGTACCATTGACCTTGAAGTCTGTGATTACCCTTAGTTAT |
| ATCTTGACCCTCAACACAGCTAAACATGGGTTCGCAGGTGTCTACACAGCGCTCCGGTTC |
| TCACGAAAACTCAAACTCAGCCACTGAAGGTTCCACCATAAACTACACCACCATTAATTA |
| CTACAAAGACTCCTATGCTGCCACAGCAGGCAAACAGAGTCTCAAGCAGGATCCAGACAA |
| GTTTGCAAATCCTGTTAAAGACATCTTCACTGAAATGGCAGCGCCACTGAAATCTCCATC |
| CGCTGAGGCATGTGGATACAGCGATCGAGTGGCGCAATTAACCATTGGCAACTCCACCAT |
| CACCACGCAAGAAGCGGCTAACATCATAGTTGGTTATGGTGAGTGGCCTTCCTACTGCTC |
| GGATTCTGACGCTACAGCAGTGGATAAACCAACGCGCCCGGATGTTTCAGTGAACAGGTT |
| TTATACATTGGACACCAAGTTGTGGGAGAAATCGTCCAAGGGATGGTACTGGAAGTTCCC |
| GGATGTGTTAACTGAAACCGGGGTTTTTGGGCAAAATGCACAATTCCACTACCTCTACCG |
| ATCAGGGTTCTGTATTCACGTGCAGTGCAATGCTAGTAAATTTCACCAAGGAGCACTCCT |
| AGTTGCTGTCCTACCAGAGTACGTCATTGGGACAGTGGCTGGCGGTACAGGGACGGAAGA |
| CAGTCACCCTCCTTACAAGCAGACTCAACCCGGCGCCGATGGCTTCGAATTGCAACACCC |
| GTACGTGCTTGATGCTGGCATCCCAATATCACAGTTAACAGTGTGCCCACACCAGTGGAT |
| TAATTTGAGGACCAACAATTGTGCTACAATAATAGTGCCATACATTAACGCACTACCTTT |
| TGATTCTGCTTTGAACCACTGTAACTTTGGCCTATTAGTTGTGCCTATTAGCCCGCTAGA |
| TTACGACCAAGGAGCGACGCCAGTAATCCCTATAACTATCACATTGGCCCCAATGTGTTC |
| TGAATTCGCAGGTCTCAGGCAAGCAGTCACGCAAGGGTTTCCCACCGAGCTGAAACCTGG |
| CACAAATCAATTTTTAACCACTGATGATGGCGTTTCGGCACCTATTCTACCAAACTTCCA |
| CCCCACCCCCTGTATCCACATACCTGGTGAAGTTAGGAACTTGCTAGAGTTATGCCAGGT |
| GGAGACCATTTTGGAGGTCAACAATGTGCCCACGAATGCCACTAGCTTAATGGAGAGGCT |
| GCGCTTTCCGGTCTCAGCACAAGCAGGGAAAGGCGAGCTGTGTGCGGTGTTCAGAGCCGA |
| TCCTGGGCGAAATGGACCGTGGCAGTCCACCTTCCCGGGTCAGTTGTGCGGGTATTATAC |
| CCAATGGTCAGGATCATTGGAGGTCACCTTCATGTTCACTGGATCCTTCATGGCTACTGG |
| CAAGATGCTCATAGCCTATACACCGCCGGGAGGCCCTTTGCCCAAGGACCGGGCAACCGC |
| CATGTTGGGCACGCACGTCATCTGGGATTTTGGGCTGCAATCGTCTGTTACCCTTGTGAT |
| ACCATGGATCAGCAACACTCACTACAGAGCGCATGCCCGAGATGGAGTGTTTGACTACTA |
| CACCACAGGGTTAGTCAGTATATGGTATCAGACAAATTACGTGGTTCCAATTGGGGCGCC |
| CAATACAGCCTATATAATAGCATTAGCGGCAGCCCAAAAGAACTTCACTATGAAATTGTG |
| CAAGGATGCTAGTGATATCCTGCAGACGGGCACCATCCAGGGAGATAGGGTGGCAGATGT |
| AATTGAGAGTTCCATAGGGGATAGTGTGAGCAGAGCCCTCACTCAAGCTCTACCAGCTCC |

TABLE 11-continued

| N772 strain (subgenogroup C4)(SEQ ID NO: 11) |
|---|
| CACAGGCCAGAACACACAGGTGAGCAGTCATCGACTGGATACAGGTAAGGTTCCAGCACT |
| CCAAGCTGCTGAGATTGGAGCATCATCAAATGCTAGTGATGAGAACATGATTGAGACACG |
| CTGTGTTCTTAACTCGCACAGCACAGCTGAGACCACTCTTGATAGTTTCTTCAGCAGAGC |

| [Table 11B] |
|---|
| GGGATTAGTTGGAGAGATAGATCTCCCCCTTGAAGGCACAACCAACCCAAATGGCTATGC |
| CAACTGGGACATAGATATAACAGGTTACGCGCAAATGCGTAGAAAGGTGGAGCTATTCAC |
| CTACATGCGCTTTGATGCAGAGTTCACTTTTGTTGCGTGCACACCCACCGGGGAAGTTGT |
| CCCACAATTGCTCCAATATATGTTTGTGCCACCTGGAGCCCCTAAGCCAGATTCCAGGGA |
| ATCCCTTGCATGGCAAACTGCCACCAACCCCTCAGTTTTTGTCAAGCTGTCAGACCCTCC |
| AGCGCAGGTTTCAGTACCATTCATGTCACCTGCGAGTGCTTACCAATGGTTTTATGACGG |
| ATATCCCACATTTGGAGAACATAAACAGGAGAAAGATCTTGAATATGGGGCATGTCCTAA |
| CAACATGATGGGCACGTTCTCAGTGCGGACTGTAGGGACTTCCAAGTCCAAATACCCTTT |
| AGTGGTTAGGATTTACATGAGAATGAAGCACGTCAGGGCGTGGATACCTCGCCCGATGCG |
| CAACCAAAACTACCTATTCAAAGCCAACCCAAATTATGCTGGCAACTCCATTAAGCCAAC |
| TGGTACCAGTCGCACGGCGATCACTACTCTTGGGAAATCTGGGCAACAGTCTGGGGCCAT |
| TTACGTGGGTAACTTTAGAGTGGTTAACCGTCATCTTGCCACTCATAATGATTGGGCAAA |
| TCTTGTTTGGGAAGACAGCTCTCGCGACTTCCCCGTGTCATCCACCACTGCCCAAGGTTG |
| TGACACGATTGCCCGTTGCAATTGCCAGACAGGGGTGTACTATTGTAATTCAAGAAGAAA |
| ACACTACCCAGTCAGTTTTTCAAAACCCAGCCTGATCTATGTAGAGGCTAGCGAGTATTA |
| CCCAGCCAGGTACCAGTCACATCTCATGCTCGCACAGGGCCACTCAGAACCTGGTGATTG |
| TGGTGGTATCCTTAGATGCCAACATGGTGTCGTCGGTATAGTGTCTACTGGTGGCAATGG |
| GCTCGTTGGCTTTGCAGACGTCAGGGACCTCTTGTGGTTAGATGAAGAAGCTATGGAGCA |
| GGGCGTGTCCGACTACATCAAGGGTCTCGGAGATGCTTTCGGGACAGGTTTCACTGATGC |
| AGTCTCAAGGGAGGTTGAAGCTCTCAAGAACTATCTTATAGGGTCTGAAGGAGCAGTTGA |
| AAAAATTCTAAAAAATCTTATTAAACTAATCTCTGCACTGGTGATTGTAATCAGAAGTGA |
| TTAGGACATGGTTACCCTTACTGCAACCCTAGCGCTGATAGGTTGTCATGGCAGTCCTTG |
| GGCTTGGATCAAAGCCAAAACAGCTTCTATCTTAGGCATCCCTATCGCTCAGAAGCAAAG |
| CGCTTCTTGGCTCAAGAAATTCAATGACATGGCCAACGCTGCTAAGGGGTTAGAGTGGGT |
| TTCTAATAAGATCAGCAAATTCATTGATTGGCTTAAGGAGAAAATAGTACCAGCAGCTAA |
| GGAGAAGGTTGAATTCCTAAATAACTTGAAACAGTTGCCATTGCTAGAGAATCAGATCTC |
| AAACTTGGAACAATCTGCTGCCTCACAAGAGGACCTTGAAGTCATGTTTGGGAATGTGTC |
| GTATCTAGCCCACTTCTGTCGCAAGTTCCAGCCGCTATACGCCACGGAAGCTAAAAGGGT |
| TTATGCCCTGGAGAAGAGAATGAATAACTATATGCAGTTCAAGAGCAAACACCGAATTGA |
| ACCTGTATGTCTTATTATTAGGGGCTCACCAGGCACTGGGAAGTCTTTAGCCACTGGTAT |
| CATTGCTCGAGCAATCGCTGACAAGTACCACTCCAGCGTGTACTCGCTTCCACCAGACCC |
| AGATCATTTTGATGGCTACAAGCAACAGGTGGTTACAGTGATGGATGACTTGTGTCAAAA |
| CCCCGATGGCAAGGATATGTCCTTATTCTGTCAAATGGTATCCACCGTAGACTTCATCCC |
| ACCAATGGCTTCTCTTGAGGAGAAGGGAGTTTCCTTCACCTCTAAGTTTGTTATCGCATC |
| TACTAATGCCAGTAACATCATAGTGCCAACAGTGTCTGACTCTGACGCTATTCGCCGCAG |

TABLE 11-continued

| N772 strain (subgenogroup C4)(SEQ ID NO: 11) |
|---|
| GTTCTACATGGATTGTGATATTGAAGTGACAGACTCGTACAAAACTGATCTAGGTAGACT |
| GGATGCAGGGCGAGCCGCCAAACTGTGCTCTGAGAACAACACTGCAAATTTCAAACGTTG |
| CAGCCCATTAGTGTGTGGGAAAGCTATCCAACTTAGAGATAGAAAGTCTAAAGTTAGATA |
| CAGTGTGGATACAGTAGTTTCAGAACTTATTAGGGAATACAGTAATAGGTCCGCCATTGG |
| CAACACAATCGAGGCTCTTTTCCAAGGTCCACCCAAGTTCAGGCCAATTAGGATTAGCCT |
| TGAAGAGAAACCAGCTCCGGACGCTATTAGCGATCTCCTTGCTAGTGTAGATAGTGAAGA |
| AGTGCGCCAATACTGCAGGGATCAAGGCTGGATCATTCCTGAAACTCCCACCAACGTAGA |
| GCGGCACCTTAATAGAGCAGTGCTTGTCATGCAATCCATCACCACAGTAGTGGCGGTTGT |
| CTCGTTGGTGTATGTCATCTACAAGCTCTTTGCAGGGTTTCAGGGTGCGTACTCTGGTGC |
| TCCTAAGCAAGTGCTTAAGAAACCTGCTCTTCGCACAGCAACAGTACAGGGCCCGAGCCT |
| [Table 11C] |
| TGATTTTGCTCTCTCCCTGTTGAGGAGGAACATCAGGCAAGTCCAAACAGACCAGGGGCA |
| TTTCACCATGTTGGGTGTTAGGGATCGTTTAGCAGTCCTCCCGCGTCACTCACAACCCGG |
| TAAAACTATTTGGATTGAGCATAAACTCGTGAACATCCTTGATGCAGTTGAATTGGTGGA |
| TGAGCAAGGAGTCAACCTGGAATTAACCCTCATCACTCTTGACACTAACGAAAAGTTTAG |
| GGATATCACCAAATTCATCCCAGAGAATATTAGCACTGCCAGTGATGCCACTCTAGTGAT |
| CAACACGGAGCACATGCCCTCAATGTTTGTCCCGGTGGGTGACGTTGTGCAGTATGGCTT |
| CTTGAATCTCAGTGGTAAGCCTACCCATCGCACCATGATGTACAACTTTCCTACTAAAGC |
| AGGGCAGTGTGGAGGAGTGGTGACATCTGTCGGGAAGGTTATCGGTATTCACATTGGTGG |
| CAATGGTAGACAAGGTTTTTGCGCAGGCCTCAAAAGGAGTTACTTTGCTAGTGAACAAGG |
| AGAGATCCAGTGGGTTAAGCCCAATAAAGAAACTGGAAGACTTAACATCAATGGACCAAC |
| CCGCACCAAGTTAGAACCCAGTGTATTCCATGATGTCTTCGAGGGAAATAAGGAACCAGC |
| TGTCTTGCACGGTAAAGATCCCCGACTCGAGGTAGATTTTGAGCAGGCCCTGTTCTCTAA |
| GTATGTGGGAAATACACTATATGAGCCTGACGAGTACATCAAAGAGGCAGCCCTTCATTA |
| TGCAAATCAATTAAAGCAACTAGAAATTAATACCTCTCAAATGAGCATGGAGGAGGCCTG |
| CTACGGTACTGAGAATCTTGAGGCTATTGATCTTCATACTAGTGCAGGTTACCCCTATAG |
| TGCCCTGGGAATAAAGAAAAGAGACATCTTAGACCCTACCACCAGGGACGTGAGTAAAAT |
| GAAGTTCTACATGGACAAATACGGTCTTGATCTCCCTTACTCCACTTATGTCAAGGATGA |
| GCTGCGCTCAATTGATAAAATTAGGAAAGGGAAGTCCCGTCTGATCGAGGCCAGTAGTTT |
| AAATGATTCAGTGTACCTCAGAATGACTTTCGGCCATTTGTATGAGGCTTTCCACGCAAA |
| TCCTGGGACGATAACTGGATCAGCCGTGGGGTGTAACCCTGACACATTCTGGAGCAAACT |
| GCCAATCTTGCTCCCTGGTTCACTCTTTGCCTTTGACTACTCAGGTTATGATGCTAGCCT |
| TAGCCCTGTCTGGTTCAGAGCATTAGAATTGGTCCTTAGGGAGATAGGGTATAGTGAAGG |
| CGCAGTCTCACTCATTGAGGGAATCAACCACACACACCATGTGTATCGCAATACGACCTA |
| CTGTGTGCTTGGTGGGATGCCCTCAGGCTGTTCGGGAACATCCATTTTCAACTCAATGAT |
| CAACAACATTATTATCAGGGCACTGCTCATAAAAACATTTAAGGGCATTGATTTGGACGA |
| ACTCAACATGGTCGCTTATGGAGATGATGTGCTCGCCAGCAGCTACCTCCCAATTGATTG |
| CTTGGAATTAGCAAAGACTGGCAAGGAGTATGGTCTAACCATGACTCCTGCAGATAAGTC |
| TCCTTGCTTTAATGAAGTTAATTGGGGTAATGCGACCTTCCTCAAGAGGGGCTTTCTACC |

TABLE 11-continued

| N772 strain (subgenogroup C4)(SEQ ID NO: 11) |
|---|
| CGATGAACAGTTTCCGTTTTTGATCCACCCTACTATGCCAATGAGGGAGATCCATGAATC |
| CATTCGATGGACCAAAGACGCACGAAACACTCAAGATCATGTGCGATCTTTGTGCCTCCT |
| AGCATGGCATAATGGTAAGCAAGAATATGAGAAATTTGTGAGCACAATTAGGTCTATCCC |
| AGTAGGAAGAGCGTTGGCCATCCCAAATTATGAAAATCTTAGACGCAATTCCCTCGAGTT |
| ATTTTAGAGGCTACACGTACCTCAACCCCACCAGAAATCTGGTCGTGAATATGACTGGTG |
| GGGGTAAATTTGTTATAACCAGAATAGCAAAAAAAAAAAAAAAAAAAAAAAAA |

TABLE 12

| C7/Osaka strain (subgenogroup B4)(SEQ ID NO: 12) |
|---|
| [Table 12A] |
| TTAAAACAGCCTGTGGGTTGCACCCACTCACAGGGCCCACGTGGCGCTAGCACTCTGATT |
| CCACGGAACCTTTGTGCGCCTGTTTTACGCCCCCTCCCCAATTTGCAACTTAGAAGCAAT |
| ACACAACACTGATCAACAGCAGGCATGGCACACCAGCTATGTCTTGATCAAGCACTTCTG |
| TTTCCCCGGACCGAGTATCAATAGACTGTTCACGCGGTTGAAGGAGAAAGCGTCCGTTAT |
| CCGGCTAACTACTTCGAGAAACCTAGTAGCACCATTGAAGCTGCAGAGTGTTTCGCTCGG |
| CACTTCCCCCGTGTAGATCAGGTCGATGAGTCACTGCAATCCCCACGGGCGACCGTGGCA |
| GTGGCTGCGCTGGCGGCCTGCCTATGGGGCAACCCATAGGACGCTCTAATGTGGACATGG |
| TGCGAAGAGTCTATTGAGCTAGTTAGTAGTCCTCCGGCCCCTGAATGCGGCTAATCCTAA |
| CTGCGGAGCACATGCCTTCAATCCAGAGGGTGGTGTGTCGTAATGGGCAACTCTGCAGCG |
| GAACCGACTACTTTGGGTGTCCGTGTTTCCTTTTATTCTTACATTGGCTGCTTATGGTGA |
| CAATTGCAGAATTGTTACCATATAGCTATTGGATTGGCCATCCGGTGTGCAATAGAGCTA |
| TTATATACCTATTTGTTGGCTTTGTACCACTAACCTTAAAATCTATAACCACCCTCGACT |
| TTATATTAACCCTCAATACAATCAAACATGGGCTCACAGGTGTCTACTCAGCGATCCGGT |
| TCCCACGAGAACTCCAATTCAGCTACAGAAGGCTCCACCATTAATTACACTACCATCAAC |
| TATTACAAAGACTCCTATGCTGCGACAGCGGGCAAACAAAGCCTCAAACAAGACCCTGAT |
| AAGTTTGCTAACCCTGTCAAGGACATTTTCACTGAAATGGCTGCGCCACTGAAGTCTCCA |
| TCCGCTGAAGCTTGTGGTTACAGTGATCGCGTGGCACAACTCACCATTGGAAACTCCACC |
| ATTACTACACAGGAGGCGGCAAACATCATAGTCGGTTATGGTGAGTGGCCCTCATACTGC |
| TCTGATGACGATGCTACAGCGGTGGACAAACCAACGCGCCCAGATGTTTCAGTGAATAGG |
| TTTTACACATTGGACACTAAACTGTGGGAAAAATCATCCAAGGGGTGGTATTGGAAGTTT |
| CCTGATGTGTTGACTGAGACCGGAGTCTTTGGCCAGAACGCACAGTTTCACTATTTATAT |
| AGATCAGGGTTTTGCATTCATGTACAATGTAATGCTAGCAAGTTCCATCAAGGAGCGCTG |
| TTAGTCGCTATACTTCCAGAGTATGTTATAGGGACAGTAGCAGGCGGCACAGGAACAGAG |
| GACAGCCACCCTCCTTACAAACAAACACAGCCTGGCGCCGACGGTTTTGAGCTGCAGCAC |
| CCGTACGTGCTCGATGCTGGGATTCCTATATCACAATTGACAGTCTGCCCCCATCAATGG |
| ATTAACCTGCGGACCAATAACTGTGCCACAATAATAGTGCCATATATGAATACACTGCCT |
| TTCGACTCTGCCCTGAACCATTGCAATTTTGGGCTGTTGGTAGTGCCCATTAGCCCATTA |
| GACTTTGACCAAGGGGCAACTCCGGTTATCCCTATTACAATCACTCTAGCTCCAATGTGC |
| TCTGAGTTTGCAGGTCTCAGACAGGCAGTCACACAAGGCTTTCCCACTGAGCCAAAACCA |

TABLE 12-continued

| C7/Osaka strain (subgenogroup B4)(SEQ ID NO: 12) |
| --- |
| GGAACGAATCAATTCTTGACCACCGATGACGGCGTCTCGGCGCCCATTCTACCAAATTTC |
| CACCCCACTCCATGTATTCACATACCCGGTGAAGTCAGAAACCTGCTTGAGTTGTGTCAA |
| GTGGAGACTATTCTTGAGGTTAACAACGTACCCACCAATGCTACTAGTCTGATGGAAAGG |
| CTACGATTCCCAGTGTCCGCGCAAGCGGGGAAAGGTGAATTGTGTGCCGTGTTTAGGGCC |
| GACCCTGGAAGAGACGGCCCATGGCAATCAACAATGCTGGGCCAGTTGTGTGGATATTAC |
| ACCCAGTGGTCAGGGTCACTGGAGGTCACTTTTATGTTTACCGGGTCATTCATGGCCACG |
| GGTAAAATGCTCATAGCTTACACACCTCCTGGCGGCCCATTACCTAAAGATCGGGCCACA |
| GCAATGCTGGGCACACATGTTATCTGGGATTTTGGGCTACAATCATCTGTCACCCTTGTA |
| ATACCATGGATCAGCAACACCCACTACAGGGCGCATGCCCGGGATGGAGTGTTCGATTAC |
| TATACCACAGGACTGGTCAGTATCTGGTATCAAACAAACTATGTAGTTCCAATTGGGGCA |
| CCCAACACAGCTTACATAATAGCACTAGCGGCAGCCCAGAAGAATTTTACCATGAAACTG |
| TGCAAAGACACCAGCCACATATTACAGACAGCCTCTATTCAGGGAGATAGGGTGGCAGAT |
| GTGATCGAGAGCTCTATAGGAGATAGTGTGAGTAGGGCACTTACCCAGGCCCTGCCAGCA |
| CCCACAGGTCAAAACACACAGGTGAGTAGTCATCGACTAGACACTGGCGAAGTTCCAGCG |
| CTCCAAGCTGCTGAAATTGGGGCATCGTCAAATACTAGTGATGAGAGTATGATTGAAACA |
| CGATGCGTTCTTAACTCACACAGTACAGCGGAGACCACCTTGGACAGCTTCTTCAGTAGG |

[Table 12B]

| |
| --- |
| GCAGGTTTGGTAGGAGAGATAGATCTCCCTCTTGAGGGTACCACTAATCCAAATGGTTAT |
| GCCAACTGGGACATAGACATAACTGGTTACGCACAAATGCGCAGAAAAGTGGAGCTGTTC |
| ACCTACATGCGCTTTGATGCGGAATTCACTTTTGTTGCGTGCACTCCTACTGGTGAGGTT |
| GTTCCACAATTACTCCAGTATATGTTTGTTCCCCCTGGTGCTCCCAAACCAGAGTCTAGA |
| GAGTCACTTGCTTGGCAGACAGCCACAAACCCCTCAGTTTTTGTCAAGTTGACTGATCCC |
| CCGGCACAGGTCTCAGTTCCGTTTATGTCACCCGCGAGCGCTTACCAGTGGTTTTACGAC |
| GGGTACCCCACGTTTGGAGAACATAAACAGGAGAAAGACCTTGAGTATGGAGCGTGTCCT |
| AATAATATGATGGGCACTTTCTCGGTGCGAACCGTGGGGTCATTAAAGTCCAAGTACCCT |
| TTGGTTGTCAGAATATATATGAGAATGAAGCATGTCAGGGCGTGGATACCTCGCCCGATG |
| CGCAACCAAAACTACTTGTTCAAAGCCAACCCAAACTATGCCGGTAACTCCATTAAACCG |
| ACCGGCACTAGTCGTACTGCCATTACTACCCTTGGAAAGTTCGGCCAGCAATCTGGGGCC |
| ATCTACGTGGGCAACTTCAGAGTGGTTAATCGTCACCTCGCTACTCACAATGACTGGGCG |
| AATCTCGTCTGGGAAGACAGCTCCCGCGACCTATTAGTATCGTCTACCACCGCCCAGGGC |
| TGTGACACAATTGCACGTTGTGACTGTCAAACAGGAGTGTACTATTGTAACTCCAAGAGA |
| AAGCACTACCCAGTCAGCTTCTCTAAACCCAGCCTCATATATGTGGAAGCTAGCGAGTAT |
| TACCCTGCTAGATACCAATCGCACCTGATGCTTGCAGCGGGCCACTCTGAGCCCGGTGAC |
| TGCGGAGGCATCTTAAGGTGTCAACATGGTGTAGTTGGTATAGTGTCCACTGGTGGCAAC |
| GGGCTCGTTGGTTTTGCTGATGTGAGGGATCTCTTGTGGTTAGATGAAGAGGCCATGGAG |
| CAAGGTGTGTCCGACTATATTAAGGGGCTCGGTGACGCGTTTGGAACAGGCTTCACCGAT |
| GCTGTATCCAGGGAAGTTGAAGCCCTTAGGAACCACCTCATAGGGTCTGATGGAGCAGTT |
| GAGAAAATCCTAAAGAACCTTATCAAGCTGATTTCAGCGTTAGTAATTGTGATCAGGAGT |
| GATTATGATATGGTCACCCTCACAGCAACTTTAGCCCTGATTGGTTGTCATGGAAGTCCT |

TABLE 12-continued

| C7/Osaka strain (subgenogroup B4)(SEQ ID NO: 12) |
|---|
| TGGGCTTGGATTAAAGCCAAAACAGCATCCATTTTAGGTATCCCCATCGCCCAGAAGCAG |
| AGTGCTTCTTGGCTAAAGAAATTTAATGATATGGCGAGTGCCGCCAAGGGTTTAGAATGG |
| ATATCCAACAAAATTAGTAAGTTCATTGACTGGCTCAGGGAGAAGATTGTTCCAGCAGCT |
| AAGGAGAAAGCAGAATTTTTAACCAATTTGAAGCAATTACCACTGTTAGAGAACCAGATC |
| ACGAATTTAGAGCAGTCCGCTGCCTCACAAGAGGACCTTGAAGCTATGTTTGGGAATGTG |
| TCATACCTCGCCCATTTCTGTCGCAAGTTCCAACCATTATACGCTAGGGAAGCTAAGCGA |
| GTCTATGTTCTAGAGAAGAGAATGAACAACTACATGCAGTTCAAGAGCAAACACCGTATT |
| GAACCTGTATGTCTCATCATTAGAGGCTCACCGGGCACTGGAAAGTCCCTTGCGACCGGT |
| ATCATTGCTCGGGCCATAGCAGACAAGTATCACTCTAGTGTGTACTCACTTCCACCAGAT |
| CCTGACCATTTTGACGGGTACAAACAGCAAGTGGTCACAGTTATGGATGATCTGTGTCAA |
| AATCCTGACGGCAAAGACATGTCATTATTTTGCCAGATGGTGTCCACCGTGGATTTTATC |
| CCACCAATGGCTTCTCTCGAAGAAAAGGGAGTTTCTTTCACATCTAAATTTGTTATCGCA |
| TCTACCAACGCCAGCAACATTATAGTGCCTACAGTGTCTGACTCTGACGCCATTCGTCGC |
| AGGTTTTACATGGATTGCGACATTGAGGTGACAGACTCATACAAAACAGACTTGGGTAGA |
| CTAGACGCTGGACGGGCTGCTAAGTTATGCTCTGAAAACAACACCGCAAACTTCAAACGA |
| TGCAGCCCACTAGTGTGTGGGAAAGCTATTCAACTTAGGGACAGGAAGTCTAAGGTCAGG |
| TACAGCGTGGACACAGTGGTTTCTGAACTTATTAGAGAACACAATAGCAGATCCGCTATT |
| GGTAACACAATTGAAGCACTATTCCAAGGCCCACCCAAGTTCAGGCCAATTAGAATCAGT |
| CTTGAAGAGAAGCCAGCCCCAGACGCTATTAGCGATCTCCTCGCTAGTGTAGACAGCGAG |
| GAAGTGCGCCAATACTGTAGGGAGCAAGGCTGGATCATCCCTGAAACTCCCACCAATGTT |
| GAACGACATCTTAATAGAGCAGTGCTAGTCATGCAATCCATCGCTACTGTGGTGGCAGTC |
| GTCTCACTGGTGTACGTCATTTACAAGCTCTTTGCGGGGTTTCAAGGTGCGTATTCTGGA |
| GCTCCCAAGCAAATGCTCAAGAAACCTGTCCTCCGCACGGCAACAGTACAGGGTCCGAGT |

| [Table 12C] |
|---|
| CTTGACTTTGCTCTATCCTTGCTGAGAAGGAACATCAGGCAAGTCCAAACAGATCAAGGG |
| CATTTTACTATGTTAGGTGTCAGGGATCGCTTGGCCGTTCTCCCACGGCACTCACAGCCC |
| GGGAAGACTATTTGGGTGGAGCATAAACTTGTGAACATCCTTGACGCAATCGAGCTGGTG |
| GATGAGCAGGGCGTTAATTTGGAACTCACATTGGTGACACTAGATACTAATGAAAAATTT |
| AGAGATATCACCAAGTTCATTCCAGAGACCATTAGCGGCGCTAGTGATGCAACTTTAGTG |
| ATCAACACAGAACATATGCCATCAATGTTTGTCCCAGTGGGGGACGTTGTGCAGTACGGG |
| TTCTTGAACCTTAGTGGAAAGCCAACTCATAGGACCATGATGTACAATTTCCCTACAAAA |
| GCAGGACAGTGTGGAGGTGTGGTCACATCAGTCGGTAAGATTGTCGGTATCCACATTGGC |
| GGCAACGGGCGCCAGGGGTTCTGTGCTGGTCTGAAGAGGAGTTACTTCGCAAGTGTGCAG |
| GGTGAGATCCAATGGGTGAAGCCTAACAAGGAAACTGGTAGACTGAACATCAATGGACCA |
| ACTCGCACTAAGTTGGAGCCTAGCGTATTTCATGATGTGTTTGAAGGCAATAAGGAACCA |
| GCAGTTTTAACAAGTAAAGACCCTAGATTGGAGGTCGACTTTGAGCAAGCCCTGTTTTCC |
| AAGTATGTGGGCAATGTTTTACACGAGCCCGATGAATATGTGACTCAAGCTGCCCTCCAC |
| TATGCGAATCAACTTAAACAATTGGACATAAACACTAGCAAGATGAGCATGGAGGAAGCG |
| TGCTATGGCACTGAAAACCTGGAAGCAATAGACCTCTGCACTAGTGCCGGATATCCATAC |

TABLE 12-continued

| C7/Osaka strain (subgenogroup B4)(SEQ ID NO: 12) |
|---|
| AGCGCCCTTGGCATTAAGAAAAGAGACATTCTCGACCCCACAACCAGGGATGTGTCTAAG |
| ATGAAATTCTATATGGATAAATACGGGCTAGATCTGCCATACTCTACCTATGTAAAGGAT |
| GAGCTTAGGTCCCTGGATAAAATCAAGAAAGGAAAGTCACGCCTGATAGAGGCTAGTAGC |
| TTGAATGACTCTGTCTACCTCAGAATGACTTTTGGGCACCTTTACGAAGTGTTTCATGCT |
| AACCCTGGCACTGTGACTGGCTCAGCAGTGGGTTGCAACCCGGACGTGTTTTGGAGCAAA |
| CTACCGATTCTGCTGCCTGGGTCACTCTTTGCCTTCGACTACTCAGGATATGATGCTAGT |
| CTCAGCCCGGTATGGTTCAGGGCTCTAGAAGTTGTGTTACGGGAGATTGGGTATTCAGAG |
| GAGGCCGTGTCCCTAATAGAAGGAATCAACCACACCCACCATGTGTACCGGAACAAAACA |
| TACTGTGTACTTGGTGGAATGCCCTCAGGGTGTTCTGGTACTTCCATCTTTAATACAATG |
| ATCAACAACATCATCATTAGAACCCTTTTGATCAAAACCTTTAAGGGAATAGACCTGGAT |
| GAGTTGAACATGGTGGCCTATGGGGACGATGTGCTGGCTAGTTACCCCTTTCCTATTGAT |
| TGCCTTGAGTTGGCTAAGACTGGCAAAGAGTATGGTTTGACCATGACACCTGCAGACAAA |
| TCACCCTGTTTCAATGAAGTAACATGGGAAAATGCTACCTTCCTGAAGAGAGGGTTCTTG |
| CCAGACCACCAATTTCCATTCTTAATTCACCCTACGATGCCCATGAGAGAGATCCATGAG |
| TCCATTCGATGGACTAAAGACGCGCGCAACACCCAAGATCACGTGCGCTCCCTGTGTCTG |
| TTGGCATGGCACAATGGTAAGGATGAATATGAGAAGTTTGTGAGTGCAATTAGATCAGTT |
| CCAGTTGGAAAAGCGTTGGCCATTCCTAACTTTGAGAATCTGAGAAGAAATTGGCTCGAA |
| TTGTTTTAATATTACAGCTTAAAGCTGAACCCCACTAGAAATCTGGTCGTGTTAATGACT |
| AGTGGGGGTAAATTTGTTATAACCAGAATAGCAAAAAAAAAAAAAAAAAAAAAAAAAAAA |
| AAAAAAAA |

TABLE 13

| 2716-Yamagata-03 strain (subgenogroup B5)(SEQ ID NO: 13) |
|---|
| [Table 13A] |
| TTAAAACAGCCTGTGGGTTGCACCCACTCACAGGACCCACGTGGTGCTAGCACTCTGGTT |
| CTACGGAACCCTTGTGCGCCTGTTTTACGCCCCCTCCCCAATTTGCAACTTAGAAGCAAT |
| TCACAACACTGATCAATAGCAGGCATGGCGCACCAGCTATGTCTTGATCAAGCACTTCTG |
| TTTCCCCGGACCGAGTATCAATAGACTGTTCACGCGGTTGAAGGAGAAAGCGTCCGTTAT |
| CCGGCTAACTACTTCGAGAAACCCAGTAGCGCCATTGAAACTGCAGAGTGTTTCGCTCCA |
| CACTTCCCCCGTGTAGATCAGGTCGATGAGTCACTGCAATCCCCACGGGCGACCGTGGCA |
| GTGGCTGCGCTGGCGGCCTGCCTATGGGGCAACCCATAGGACGCTCTAATGTGGACATGG |
| TGCGAAGAGTCTATTGAGCTAGTTAGTAGTCCTCCGGCCCCTGAATGCGGCTAATCCTAA |
| CTGCGGAGCACATGCCTTCAATCCAGAGGGTAGTGTGTCGTAATGGGCAACTCTGCAGCG |
| GAACCGACTACTTTGGGTGTCCGTGTTTCCTTTTATTCTCACATTGGCTGCTTATGGTGA |
| CAATTACAGAATTGTTACCATATAGCTATTGGATTGGCCATCCGGTGTGCAATAGAGCTA |
| TTATATACCTATTTGTTGGTTTTGTACCACTAACCTTAAAATCTGCAACCACTCTCGACT |
| ATATATTAACCCTCAATACAATCAAACATGGGCTCACAGGTGTCCACTCAACGATCCGGC |
| TCCCATGAAAACTCCAATTCAGCTACAGAAGGCTCCACCATTAATTACACCACTATTAAC |

TABLE 13-continued

| 2716-Yamagata-03 strain (subgenogroup B5)(SEQ ID NO: 13) |
|---|
| TATTACAAAGACTCCTATGCTGCGACAGCGGGCAAGCAGAGCCTCAAACAAGACCCTGAT |
| AAGTTTGCTAACCCTGTCAAGGACATTTTCACTGAAATGGCTGCGCCTCTAAAGTCTCCA |
| TCCGCTGAAGCTTGTGGCTACAGTGATCGCGTGGCACAACTCACCATTGGAAACTCCACC |
| ATCACTACACAGGAAGCGGCAAACATCATAGTCGGTTATGGTGAATGGCCCTCATACTGC |
| TCTGATGACGACGCTACAGCGGTGGATAAGCCAACGCGCCCAGATGTTTCCGTGAATAGG |
| TTTTATACATTGGACACTAAACTATGGGAAAAGTCATCCAAGGGGTGGTATTGGAAGTTT |
| CCTGACGTATTGACTGAGACCGGAGTCTTTGGCCAAAACGCACAGTTTCACTATTTATAT |
| AGATCAGGGTTTTGCATCCATGTGCAATGTAACGCTAGCAAGTTCCACCAAGGAGCGCTG |
| TTACTCGCTATACTTCCAGAGTATGTCATAGGGACAGTGGCGGGCGGCACAGGAACAGAG |
| GACAGTCACCCTCCTTACAAACAAACACAACCAGGTGCCGACGGTTTTGAATTGCAGCAC |
| CCGTATGTGCTCGATGCTGGGATCCCTATATCACAATTGACAGTATGCCCCCATCAATGG |
| ATTAACTTACGGACTAATAACTGTGCCACAATAATAGTGCCATATATGAATACACTGCCT |
| TTTGACTCCGCCCTGAACCATTGCAATTTTGGGCTGTTGGTAGTACCCATTAGCCCATTA |
| GATTTTGACCAAGGGGCAACTCCGGTTATCCCTATTACAATCACTCTAGCTCCAATGTGC |
| TCCGAATTTCCCGGTCTCAGGCAGGCAGTCACTCAAGGCTTTCCCACTGAGCCAAAACCA |
| GGGACGAATCAATTCTTGACCACCGATGATGGCGTCTCAGCACCCATTCTACCAAATTTC |
| CATCCCACTCCATGTATTCACATACCCGGTGAAGTCAGAAACCTGCTTGAGTTGTGTCAA |
| GTGGAGACTATTCTTGAGGTTAACAACGTACCCACCAATGCTACTAGTTTGATGGAAAGA |
| CTACGATTCCCGGTGTCCGCGCAAGCGGGGAAAGGTGAATTGTGTGCCGTGTTTAGGGCT |
| GATCCTGGAAGAGACGGTCCATGGCAGTCAACGATGCTGGGCCAGTTGTGTGGATACTAC |
| ACTCAGTGGTCAGGGTCACTGGAGGTCACTTTCATCTTCACCGGGTCTTTCATGGCCACG |
| GGTAAGATGCTCATAGCTTATACACCCCCTGGCGGTCCCTTACCCAAAGATCGGGCTACA |
| GCAATGCTGGGCACACATGTTATCTGGGACTTTGGGCTACAATCATCTGTCACCCTTGTG |
| ATACCATGGATCAGTAACACTCACTACAGGGCGCATGCCCGGGATGGAGTGTTCGACTAC |
| TATACCACAGGACTGGTCAGTATCTGGTATCAAACAAATTATGTAGTCCCAATTGGGGCA |
| CCCAACACAGCTTACATAATAGCACTGGCGGCGGCCCAGAAGAATTTTACCATGAAACTG |
| TGCAAAGACACTAGTCACATACTACAGACAGCCTCTATTCAGGGAGATAGGGTGGCAGAT |
| GTGATCGAGAGCTCTATAGGGGACAGCGTGGGTAGGGCACTCACCCAGGCCCTGCCAGCA |
| CCCACAGGTCAAAACACACAGGTGAGCAGCCATCGACTAGACACTGGTGAAGTTCCAGCG |
| CTCCAAGCTGCTGAGATCGGGGCATCGTCAAATACTAGTGATGAGAGTATGATTGAGACA |
| CGATGCGTCCTTAACTCACACAGTACAGCAGAGACTACCCTGGACAGTTTCTTTAGCAGA |

[Table 13B]

| |
|---|
| GCAGGTTTGGTAGGAGAGATAGATCTCCCTCTAGAGGGTACTACCAATCCAAATGGTTAT |
| GCCAACTGGGATATAGACATAACTGGTTATGCACAAATGCGCAGGAAAGTGGAGCTGTTC |
| ACCTATATGCGCTTTGATGCGGAATTCACTTTCGTTGCGTGCACTCCTACTGGTGAGGTT |
| GTTCCACAACTACTCCAGTATATGTTTGTTCCCCCTGGTGCTCCTAAACCAGAGTCTAGA |
| GAATCACTTGCTTGGCAGACAGCCACAAACCCTTCAGTTTTTGTCAAATTAACTGATCCC |
| CCGGCACAGGTCTCAGTTCCGTTCATGTCACCCGCGAGCGCTTATCAGTGGTTTTACGAC |
| GGGTACCCCACGTTTGGAGAACACAAACAGGAGAAAGATCTTGAATATGGAGCGTGTCCT |

TABLE 13-continued

| 2716-Yamagata-03 strain (subgenogroup B5)(SEQ ID NO: 13) |
|---|
| AACAACATGATGGGCACTTTCTCGGTGCGGACCGTGGGGTCTTCGAAATCCAAGTACCCT |
| TTGGTTGTCAGAATATACATGAGAATGAAGCATGTCAGGGCATGGATACCTCGCCCGATG |
| CGCAACCAAAATTACTTGTTCAAAGCCAATCCAAATTATGCCGGCAACTCCATTAAGCCG |
| ACCGGTACTAGTCGTACCGCTATTACTACCCTTGGAAAGTTCGGCCAGCAATCTGGGGCC |
| ATCTACGTGGGCAACTTCAGAGTGGTTAATCGTCACCTCGCTACTCATAATGACTGGGCA |
| AACCTCGTTTGGGAAGACAGCTCCCGCGACCTATTAGTGTCGTCTACCACCGCCCAGGGC |
| TGTGATACAATTGCACGTTGTGACTGTCAAACAGGAGTGTACTATTGTAACTCCAAGAGA |
| AAGCACTATCCAGTCAGCTTTTCTAAACCCAGCCTCATATATGTGGAAGCTAGCGAGTAT |
| TACCCTGCTAGGTACCAGTCGCACCTGATGCTTGCAGCGGGCCACTCTGAGCCCGGCGAC |
| TGCGGAGGCATCTTGAGGTGTCAACATGGTGTAGTTGGTATAGTGTCCACGGGTGGCAAC |
| GGACTCGTTGGCTTTGCTGATGTGAGGGACCTCTTGTGGTTAGACGAAGAAGTCATGGAG |
| CAAGGTGTCTCCGACTACATTAAGGGGCTTGGTGACGCGTTTGGGACAGGCTTCACCGAT |
| GCTGTGTCCAGGGAAGTTGAAGCCCTTAGGAACCACCTTATAGGATCTGATGGAGCAGTT |
| GAGAAAATCCTAAAGAACCTTATTAAGCTGATTTCAGCGTTAGTAATTGTGATCAGGAGC |
| GATTATGATATGGTCACCCTCACAGCTACTTTAGCCCTGATTGGTTGCCATGGAAGTCCT |
| TGGGCTTGGATCAAAGCCAAGACAGCATCCATTTTAGGCATCCCCATTGCCCAGAAGCAG |
| AGTGCTTCTTGGCTAAAGAAGTTCAATGATATGGCGAGTGCCGCCAAGGGTTTAGAGTGG |
| ATATCCAACAAAATTAGTAAATTCATTGACTGGCTCAGAGAGAAGATTGTTCCAGCAGCT |
| AGAGAGAAAGCAGAATTCTTAACCAACTTGAAGCAATTGCCACTGTTAGAGAACCAGATC |
| ACGAATTTAGAACAGTCCGCTGCCTCACAAGAGGACCTTGAAGCCATGTTTGGGAATGTG |
| TCATACCTCGCTCATTTCTGTCGCAAGTTCCAACCATTATACGCCACAGAAGCTAAGCGG |
| GTCTATGTTCTAGAGAAGAGAATGAACAACTACATGCAGTTCAAGAGCAAACACCGTATT |
| GAACCTGTATGTCTTATCATTAGAGGCTCACCAGGCACTGGGAAGTCCCTTGCGACCGGA |
| ATCATTSCTCGGGCCATAGCAGATAAGTATCACTCTAGTGTGTACTCACTTCCACCAGAC |
| CCTGACCATTTTGACGGGTACAAACAGCAAGTGGTCACAGTTATGGATGATCTGTGTCAG |
| AATCCCGACGGCAAGGATATGTCGCTATTTTGCCAGATGGTGTCCACCGTGGATTTTATC |
| CCACCAATGGCTTCTCTTGAAGAAAAGGGAGTTTCTTTTACATCTAAATTTGTTATTGCA |
| TCCACCAACGCCAGCAACATTATAGTGCCTACAGTGTCTGACTCTGACGCCATCCGACGC |
| AGGTTTTACATGGATTGCGACATTGAGGTGACGGACTCATATAAAACAGACTTGGGTAGA |
| CTAGATGCTGGACGGGCTGCTAAGTTATGCTCTGAAAACAACACCGCAAACTTCAAACGA |
| TGCAGCCCTCTAGTGTGTGGGAAGGCTATTCAACTTAGAGACAGGAAGTCCAAGGTCAGG |
| TACAGCGTGGACACAGTGATCTCTGAACTAATTAGAGAATACAATAGCAGATCCGCTATT |
| GGTAACACAATTGAAGCACTATTCCAAGGCCCGCCTAAGTTCAGGCCAATTAGAATCAGT |
| CTTGAGGAGAAGCCAGCCCCAGACGCTATTGGCGATCTTCTCGCTAGTGTAGACAGCGAG |
| GAAGTGCGCCAATACTGTAGGGAGCAAGGCTCGATCATCCCTGAAACTCCCACCAATGTT |
| GAACGACATCTTAACAGAGCAGTGCTAGTTATGCAATCCATCGCTACTGTGGTGGCAGTT |
| GTCTCACTGGTGTATGTCATTTACAAGCTCTTTGCGGGGTTTCAAGGCGCGTATTCTGGA |
| GCTCCCAAGCAAGTGCTCAAGAAACCCGTCCTCCGCACGGCAACAGTGCAGGGTCCAAGT |

TABLE 13-continued

| 2716-Yamagata-03 strain (subgenogroup B5)(SEQ ID NO: 13) |
|---|
| [Table 13C] |
| CTTGACTTTGCTCTATCCCTGCTGAGAAGGAACATCAGGCAAGTCCAAACAGATCAGGGG |
| CATTTTACCATGTTAGGTGTCAGGGATCGCTTAGCTGTTCTCCCACGGCACGCACAGCCC |
| GGGAAGACTATTTGGGTGGAGCACAAGCTTGTGAACGTCCTCGACGCAATCGAGCTGGTG |
| GATGAACAGGGCGTTAATTTGGAACTCACATTGGTGACACTAGACACTAATGAAAAATTT |
| AGAGATATCACCAAGTTCATTCCAGAGACCATTAGCGGCGCTAGTGATGCAACTTTAGTG |
| ATCAATACAGAACATATGCCATCAATGTTTGTCCCAGTGGGGGACGTCGTGCAGTATGGG |
| TTCTTGAACCTTAGTGGGAAGCCAACACATAGGACCATGATGTACAATTTCCCTACAAAA |
| GCAGGACAATGTGGAGGTGTGGTCACATCAGTCGGTAAGATTGTTGGCATTCACATTGGC |
| GGCAACGGGCGCCAAGGGTTCTGTGCTGGTTTGAAGAGGAGTTACTTCGCAAGTGTGCAG |
| GGTGAGATCCAATGGGTGAAGCCTAACAAAGAAACTGGTAGACTGAACATCAATGGACCA |
| ACTCGCACTAAGCTGGAGCCTAGTGTGTTTCATGATGTGTTTGAAGGCAATAAGGAACCA |
| GCAGTCTTAACAAGTAAGGACCCTAGATTGGAGGTCGACTTTGAGCAAGCCCTGTTTTCC |
| AAGTATGTGGGCAATGTTTTACATGAGCCCGATGAATACGTGACTCAAGCTGCCCTCCAC |
| TATGCGAATCAACTCAAACAGTTGGACATAAACACTAGCAAGATGAGCATGGAGGAAGCG |
| TGCTATGGCACTGAGAACCTGGAAGCAATAGATCTCTGTACTAGTGCCGGATATCCATAC |
| AGCGCCCTTGGCATCAAGAAAAGAGACATTCTCGACCCCGTAACCAGGGATGTGTCTAAG |
| ATGAAATTCTATATGGATAAATACGGGCTAGATCTGCCATACTCCACCTACGTGAAGGAT |
| GAGCTTAGATCCCTGGATAAAATCAAGAAAGGAAAATCACGCCTGATAGAGGCTAGTAGC |
| TTGAATGACTCTGTCTACCTCAGAATGACCTTTGGGCATCTTTACGAGGTATTTCATGCT |
| AACCCTGGCACTGTGACCGGTTCGGCAGTGGGTTGCAACCCAGACGTGTTTTGGAGTAAA |
| CTACCGATCCTACTGCCTGGGTCACTCTTTGCCTTTGACTACTCAGGATATGATGCTAGC |
| CTCAGCCCGGTATGGTTCAGGGCTCTAGAAGTTGTGTTACGGGAAATTGGGTATCCAGAG |
| GAGGCTGTGTCCCTAATAGAAGGAATCAACCACACTCACCACGTGTACCGGAACAAAACA |
| TATTGTGTACTTGGTGGGATGCCTTCAGGGTGTTCTGGTACTTCCATCTTTAACTCAATG |
| ATCAACAACATCATCATTAGAACCCTCTTAATCAAAACCTTTAAGGGAATAGACCTGGAT |
| GAGTTGAACATGGTGGCCTATGGGGACGATGTATTGGCTAGTTATCCCTTTCCTATCGAT |
| TGCCTTGAGCTGGCTAAGACTGGCAAAGAGTATGGTTTGACTATGACACCTGCAGACAAA |
| TCACCCTGTTTCAATGAAGTGACATGGGAAAATGCTACCTTCCTTAAGAGAGGGTTCTTG |
| CCAGACCACCAATTTCCATTCTTAATTCACCCTACGATGCCTATGAGAGAGATCCATGAG |
| TCCATTCGATGGACTAAAGACGCACGCAATACCCAAGATCACGTGCGCTCTCTGTGCCTG |
| TTGGCATGGCACAATGGTAAGGATGAATATGAAAAGTTTGTGAGTGCAATTAGATCAGTT |
| CCAGTTGGAAAAGCGTTGGCCATTCCTAATTTTGAGAATTTGAGAAGAAATTGGCTCGAA |
| TTATTTTAACATTACAGCTTAAAGCTGAACCCCACTAGAAATCTGGTCGTGTTAATGACT |
| AGTGGGGGTAAATTTGTTATAACCAGAATAGCAAAAAAAAAAAAAAAAAAAAAA |

TABLE 14

| Primer sets used in PCR (SEQ ID NOs: 14 to 21) [Table 14] | | |
|---|---|---|
| primer name | primer sequence(5'→3') | No. |
| Y90-3896-5' | CTTTCGTCTTCAAGAATTGCGGCCGCGTAATACGACTCA CTATAGGTTAAAACAGCCTGTGGGTTG | 14 |
| Y90-3896-3' | GAGAATTGTCGAATATGTTTAAACTTTTTTTTTTTTTTT TTTTTTTTTTGCTATTCTGG | 15 |
| N772-5' | CTAGGCGGCCGCGTAATACGACTCACTATAGGTTAAAAC AGCCTGTGGGTTG | 16 |
| N772-3' | CACAGTCGACTTTTTTTTTTTTTTTTTTTTTTTTTGCTA TTCTGG | 17 |
| C7/Osaka-5' | CTAGGCGGCCGCGTAATACGACTCACTATAGGTTAAAAC AGCCTGTGGGTTG | 18 |
| C7/Osaka-3' | CACACTCGAGTTTTTTTTTTTTTTTTTTTTTTTTTGCTA TTCTGG | 19 |
| 2716-Yarnagata-5' | CTTTCGTCTTCAAGAATTGCGGCCGCGTAATACGACTCA CTATAGGTTAAAACAGCCTGTGGGTTG | 20 |
| 2716-Yamagata-3' | GAGAATTGTCGAATATGTTTAAACTTTTTTTTTTTTTTT TTTTTTTTTTGCTATTCTGG | 21 |

EV71 with a passage number of P0 was prepared by the same procedures as in the above Item 3 except that RD-ΔEXT1-SCARB2 was used as a host cell instead of RD-SCARB2. RD-ΔEXT1-SCARB2 cells were infected with the obtained EV71 with a passage number of P0 to obtain EV71 with a passage number of P1. Each hSCARB2-Tg10 transgenic mouse immunized with an inactivated vaccine was challenged by the same procedures as in the above item 6 except that the obtained EV71 with a passage number of P1 was used as a challenge virus (amount of the virus inoculated: $1\times10^6$ $TCID_{50}$). The death rate and the rate of paralysis were calculated.

The results are shown in Table 15. All the EV71 viruses passage-culturing using RD-ΔEXT1-SCARB2 cells had high virulence, confirming that the virus can be used as a challenge virus. The inactivated vaccine prepared in the above Item 6 was found to be effective not only for the Isehara strain but for various virulent EV71 strains differing in subgenogroup.

TABLE 15

Protective effect of inactivated vaccine on challenge infection with virulent EV71 (RD-ΔEXT1-SCARB2(P1))

| Challenge virus strain (subgenogroup) | Amount of vaccination (μg/shot) | Neutralizing antibody titer (geometric mean) | Death rate (%) | Rate of paralysis (%) |
|---|---|---|---|---|
| Y90-3896 (C1) | 0 | <16 | 100 | 100 |
| | 0.3 | 1235.2 | 0 | 0 |
| Isehara (C2) | 0 | <16 | 100 | 100 |
| | 0.3 | 640 | 0 | 0 |
| N772 (C4) | 0 | <16 | 100 | 100 |
| | 0.3 | 1254.4 | 0 | 0 |
| C7/Osaka (B4) | 0 | <16 | 100 | 100 |
| | 0.3 | 1100.8 | 0 | 0 |
| 2716-Yamagata | 0 | <16 | 100 | 100 |
| (B5) | 0.3 | 3251.2 | 0 | 0 |

9. Vaccine Efficacy Test Using Virulent EV71—(4)

Each adult hSCARB2-Tg10 mouse was immunized and challenged by the same procedures as in the above Item 6 except that the N772 strain (RD-ΔEXT1-SCARB2(P1), $10^6$ $TCID_{50}$) prepared in the above Item 8 was used as a challenge virus. The neutralizing antibody titer in serum, the change in body weight, the death rate and the rate of paralysis were calculated, and the inactivated vaccine was evaluated for its efficacy.

Figure 4:
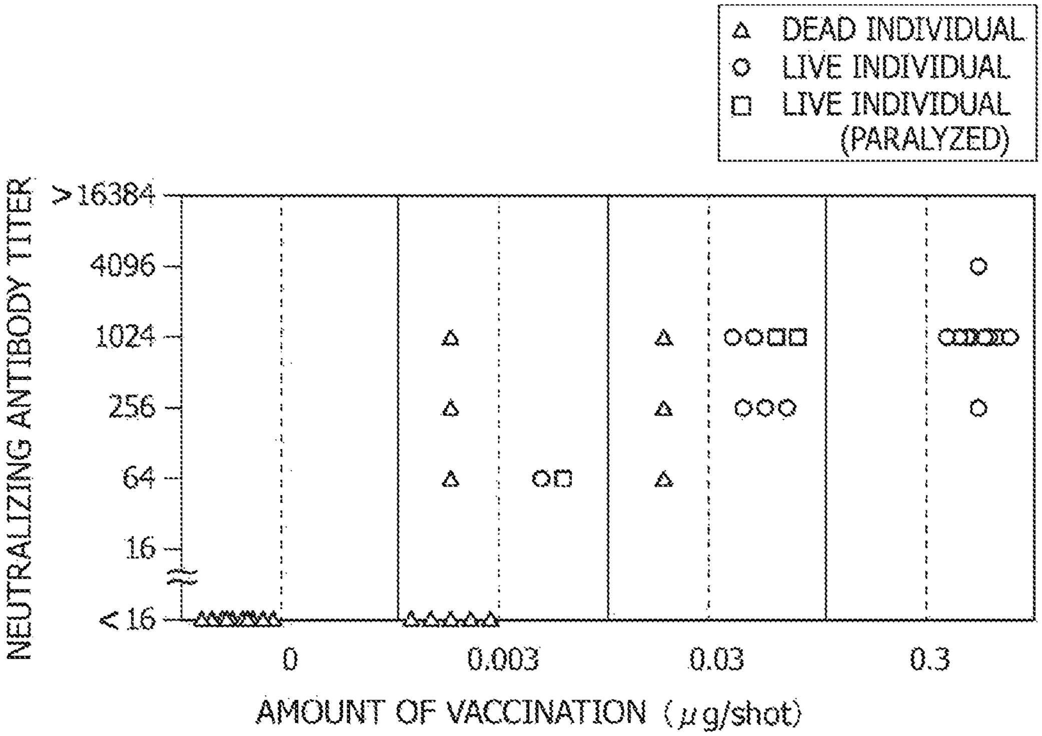
FIG. 4 is a graph showing the neutralizing antibody titers and live or dead status of mice (vaccination (−) or (+)) challenged with the virulent EV71 (N772 strain).

The results are shown in FIGS. 3 and 4 and Table 16. The hSCARB2-Tg10 mice not inoculated with the inactivated vaccine exhibited remarkable decrease in body weight, and both of their death rate and rate of paralysis were 100%. In contrast, elevation in neutralizing antibody titer and remarkable decrease in death rate and rate of paralysis were observed with increase in the amount of the inactivated vaccine inoculated, confirming protection against challenge with virulent EV71. These results demonstrated that an anti-EV71 vaccine can be evaluated for its efficacy and screened for by use of an adult hSCARB2-Tg10 mousse and an EV71 strain passage-culturing in a host cell deficient in HS and overexpressing SCARB2.

TABLE 16

Protective effect of inactivated vaccine on challenge infection with N772 strain (RD-ΔEXT1-SCARB2(P1))

| Amount of vaccination (μg/shot) | Death rate (%) | Rate of paralysis (%) |
|---|---|---|
| 0 | 100 | 100 |
| 0.003 | 80 | 90 |
| 0.03 | 30 | 50 |
| 0.3 | 0 | 0 |

Further, suppressive effects on the culturing of virulent EV71 by the inoculation of an inactivated vaccine were evaluated by calculating the titer of EV71 in the spinal cord. Each adult hSCARB2-Tg10 mouse was immunized with the inactivated vaccine and challenged with the N772 strain (RD-ΔEXT1-SCARB2(P), $10^6$ $TCID_{50}$) prepared in the above Item 8, by the same procedures as in the above Item 6. The spinal cord was excised (up to 0.1 g) from each mouse (6 mice for each group) 1 day, 2 days, and 3 days after the challenge and homogenized by the addition of a 10-fold amount of DMEM (Nissui Pharmaceutical Co., Ltd.). The obtained homogenate was centrifuged at 15000 rpm at 4° C. for 20 minutes, and the supernatant was collected. The virus titer ($TCID_{50}$) of the supernatant was measured using RD-SCARB2 cells.

Figure 5:
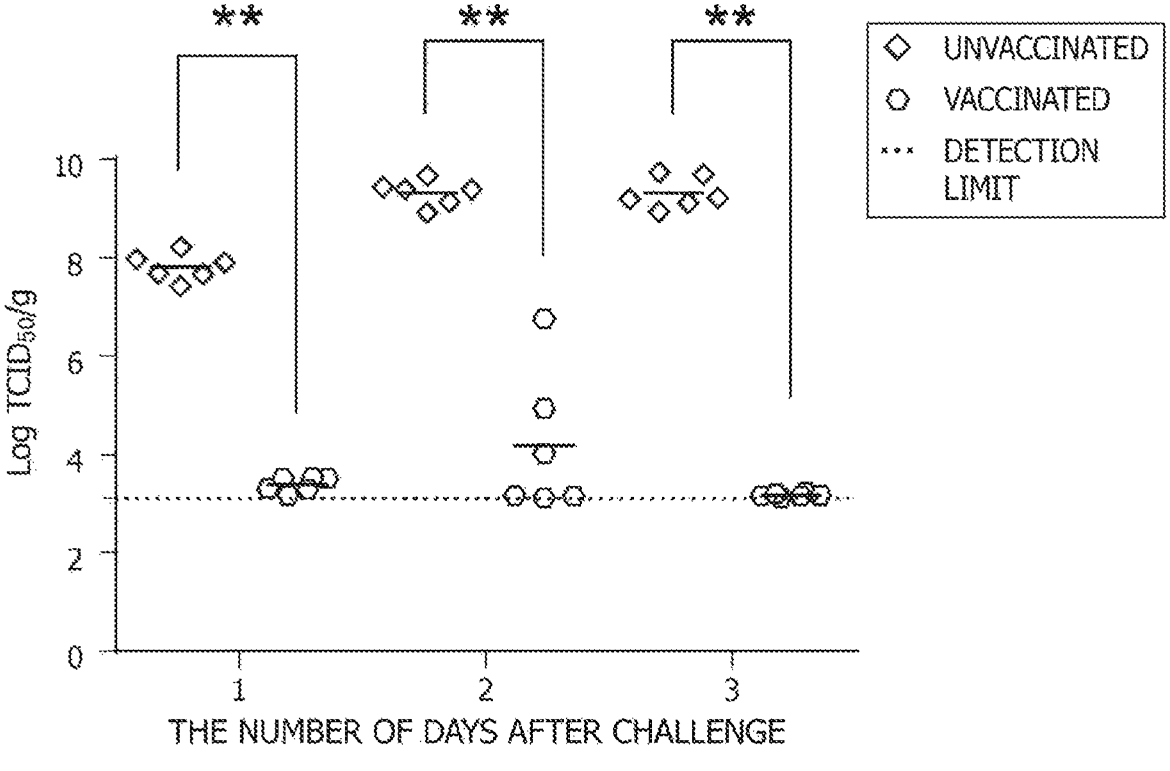
FIG. 5 is a graph showing virus titers ($TCID_{50}$) in the spinal cords of mice (vaccination (−) or (+)) challenged with the virulent EV71 (N772 strain).

The results are shown in FIG. 5. EV71 grew in the spinal cords of the hSCARB2-Tg10 mice not inoculated with the inactivated vaccine, whereas the culturing of EV71 was hardly seen in the spinal cords of the hSCARB2-Tg10 mice inoculated with the inactivated vaccine. These results also demonstrated that an anti-EV71 vaccine can be evaluated for its efficacy and screened for by use of an adult hSCARB2-Tg10 mouse and an EV71 strain passage-culturing in a host cell deficient in HS and overexpressing SCARB2.

The invention claimed is:

1. A host cell for stably propagating a virulent hand, foot and mouth disease virus, wherein the host cell is a mammalian cell, wherein the virus is enterovirus 71. Coxsackie virus A16, Coxsackie virus A14 or Coxsackie virus A7, the host cell expressing no heparan sulfate due to knock-out or knock-down of at least one gene encoding an enzyme involved in the biosynthesis of heparan sulfate in the host cell, and overexpressing primate scavenger receptor class B member 2 (SCARB2) beyond the expression level of a host cell harboring no exogenous SCARB2-encoding gene.

2. The host cell according to claim 1, wherein the host cell does not express EXT1 gene and/or EXT2 gene.

3. The host cell according to claim 1, wherein the primate SCARB2 is human SCARB2.

4. The host cell according to claim 1, wherein the cell is an RD cell.

5. A method for stably producing a virulent hand, foot and mouth disease virus, comprising the steps of (1) introducing genomic RNA of the virulent hand, foot and mouth disease virus into a host cell according to claim 1 so as to obtain a cell producing the virulent hand, foot and mouth disease virus;

(2) culturing the cell obtained by the step (1) so as to propagate the virulent hand, foot and mouth disease virus; and (3) harvesting the virulent hand, foot and mouth disease virus propagated by the step (2);

wherein the virus is enterovirus 71. Coxsackie virus A16, Coxsackie virus A14 or Coxsackie virus A7.

6. The method according to claim 5, wherein the host cell does not express EXT1 gene and/or EXT2 gene.

7. The method according to claim 5, wherein the primate SCARB2 is human SCARB2.

8. The method according to claim 5, wherein the cell is an RD cell.

* * * * *

UNITED STATES PATENT AND TRADEMARK OFFICE

CERTIFICATE OF CORRECTION

PATENT NO. : 11,339,376 B2
APPLICATION NO. : 16/496326
DATED : May 24, 2022
INVENTOR(S) : Koike et al.

It is certified that error appears in the above-identified patent and that said Letters Patent is hereby corrected as shown below:

In the Specification

Column 1, Line 17: Please correct "5576-361ST25.txt" to read --5576-361_ST25.txt--

Column 4, Line 58: Please correct "strains subgenogroup C1)" to read --strains (subgenogroup C1)--

Column 11, Line 14: Please correct "(13B)" to read --(BB)--

Column 20, Line 45: Please correct "RD-SCAR132" to read --RD-SCARB2--

Column 23, Line 31: Please correct "($LD_{50}=19^{3.5}$)" to read --($LD_{50}=10^{3.5}$)--

Column 51, SEQ ID NO. 20, Table 14: Please correct "2716-Yarnagata-5′" to read --2716-Yamagata-5′--

In the Claims

Column 91, Line 12, Claim 1: Please correct "enterovirus 71." to read --enterovirus 71,--

Column 91, Line 27, Claim 5: Please correct "steps of" to read --steps of:--

Column 92, Line 19, Claim 5: Please correct "enterovirus 71." to read --enterovirus 71,--

Signed and Sealed this
Eleventh Day of October, 2022

Katherine Kelly Vidal

Katherine Kelly Vidal
*Director of the United States Patent and Trademark Office*